United States Patent
Batt

(10) Patent No.: US 6,919,356 B2
(45) Date of Patent: Jul. 19, 2005

(54) N-SUBSTITUTED HETEROCYCLIC AMINES AS MODULATORS OF CHEMOKINE RECEPTOR ACTIVITY

(75) Inventor: Douglas G. Batt, Wilmington, DE (US)

(73) Assignee: Bristol Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/670,596

(22) Filed: Sep. 25, 2003

(65) Prior Publication Data

US 2004/0067935 A1 Apr. 8, 2004

Related U.S. Application Data

(60) Provisional application No. 60/413,895, filed on Sep. 26, 2002.

(51) Int. Cl.[7] ................. A61K 31/454; C07D 401/02
(52) U.S. Cl. .................. 514/326; 546/210; 546/209; 546/231; 514/331
(58) Field of Search ................. 514/326, 331; 546/210, 209, 231

(56) References Cited

U.S. PATENT DOCUMENTS

| | | | |
|---|---|---|---|
| 5,621,010 A | 4/1997 | Sueda et al. | |
| 5,668,151 A | 9/1997 | Poindexter et al. | |
| 5,753,654 A | 5/1998 | Kikuchi et al. | |
| 5,973,160 A | 10/1999 | Poss et al. | |
| 6,136,827 A | 10/2000 | Caldwell et al. | |
| 6,166,015 A | 12/2000 | Rogers et al. | |
| 6,339,087 B1 | 1/2002 | Gong et al. | |
| 6,441,001 B1 | 8/2002 | Watson et al. | |
| 6,515,151 B1 | 2/2003 | Poss et al. | |
| 6,521,592 B2 | 2/2003 | Ko et al. | |
| 2002/0094989 A1 | 7/2002 | Hale et al. | |

FOREIGN PATENT DOCUMENTS

| | | |
|---|---|---|
| EP | 625507 | 7/1997 |
| EP | 903349 | 3/1999 |
| ES | 2007808 | 7/1989 |
| JP | 4208267 | 7/1992 |
| JP | 2003155285 | 5/2003 |
| WO | WO 94/22846 | 10/1994 |
| WO | WO 95/13069 | 5/1995 |
| WO | WO 97/27752 | 8/1997 |
| WO | WO 97/38665 | 10/1997 |
| WO | WO 98/18761 | 5/1998 |
| WO | WO 98/25604 | 6/1998 |
| WO | WO 99/04794 | 2/1999 |
| WO | WO 00/35451 | 6/2000 |
| WO | WO 00/55143 | 9/2000 |
| WO | WO 00/59497 | 10/2000 |
| WO | WO 00/76512 | 12/2000 |
| WO | WO 00/76973 | 12/2000 |
| WO | WO 01/68604 | 9/2001 |
| WO | WO 01/98269 | 12/2001 |
| WO | WO 02/00676 | 1/2002 |
| WO | WO 02/18335 | 3/2002 |
| WO | WO 02/26723 | 4/2002 |
| WO | WO 02/083134 | 10/2002 |
| WO | WO 03/015717 | 2/2003 |
| WO | WO 03/070242 | 8/2003 |
| WO | WO 03/082291 | 10/2003 |
| WO | 03/086394 | * 10/2003 ....... A61K/31/4375 |

OTHER PUBLICATIONS

Shey et al., "Liquid Phase Combinatorial Synthesis of Benzylpiperazines", *Bioorganic & Medicinal Chemistry Letters*, vol. 9, 1999, pp. 519–522.

Mayer et al., "New Substituted 1-(2,3-Dihydrobenzo[1,4] dioxin-2-ylmethyl)piperidin-4-yl Derivatives with $\alpha_s$-Adrenoceptor Antagonist Activity", *J. Med. Chem.*, 2000, vol. 43, pp. 3653–3664.

Database CAPLUS on STN No. 136:37522, "Preparation of piperidines as orexin receptor antagonists", abstract, Branch et al., Feb. 2002.

* cited by examiner

*Primary Examiner*—Charanjit S. Aulakh
(74) *Attorney, Agent, or Firm*—Mary VanAtten

(57) ABSTRACT

The present application describes modulators of chemokine receptors of formula (I):

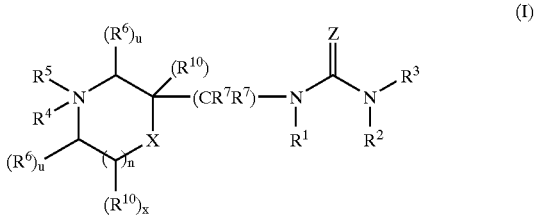

or pharmaceutically acceptable salt forms thereof, useful for the prevention of asthma and other allergic diseases.

21 Claims, No Drawings

N-SUBSTITUTED HETEROCYCLIC AMINES AS MODULATORS OF CHEMOKINE RECEPTOR ACTIVITY

CROSS-REFERENCE TO RELATED APPLICATIONS

The present application claims the priority benefit of U.S. Provisional Application No. 60/413,895, filed Sep. 26, 2002, which is expressly incorporated fully herein by reference.

FIELD OF THE INVENTION

This invention relates generally to modulators of chemokine receptor activity, pharmaceutical compositions containing the same, and methods of using the same as agents for treatment and prevention of inflammatory diseases such as asthma and allergic diseases, as well as autoimmune pathologies such as rheumatoid arthritis and atherosclerosis.

BACKGROUND OF THE INVENTION

Chemokines are chemotactic cytokines, of molecular weight 6–15 kDa, that are released by a wide variety of cells to attract and activate, among other cell types, macrophages, T and B lymphocytes, eosinophils, basophils and neutrophils (reviewed in Luster, New Eng. J Med., 338, 436–445 (1998) and Rollins, Blood, 90, 909–928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α MIP-1β, the monocyte chemotactic proteins (MCP-1, MCP-2, MCP-3, MCP-4, and MCP-5) and the eotaxins (-1, -2, and -3) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in Horuk, Trends Pharm. Sci., 15, 159–165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., Cell, 72, 415–425 (1993), Luster, New Eng. J. Med., 338, 436–445 (1998)); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., Proc. Natl. Acad. Sci. USA, 91, 2752–2756 (1994), Luster, New Eng. J. Med., 338, 436–445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491–16494 (1995), Luster, New Eng. J. Med., 338, 436–445 (1998)); CCR-4 (or "CKR-4" or "CC-CKR-4") [TARC, MIP-1α, RANTES, MCP-1] (Power et al., J. Biol. Chem., 270, 19495–19500 (1995), Luster, New Eng. J. Med., 338, 436–445 (1998)); CCR-5 (or "CKR-5" OR "CC-CKR-5") [MIP-1α, RANTES, MIP-1β] (Sanson, et al., Biochemistry, 35, 3362–3367 (1996)); CCR-6 (or "CKR-6" or "CC-CKR-6") [LARC] (Baba et al., J. Biol. Chem., 272, 14893–14898 (1997)); CCR-7 (or "CKR-7" or "CC-CKR-7") [ELC] (Yoshie et al., J. Leukoc. Biol. 62, 634–644 (1997)); CCR-8 (or "CKR-8" or "CC-CKR-8") [I-309, TARC, MIP-1β] (Napolitano et al., J. Immunol., 157, 2759–2763 (1996), Bernardini et al., Eur. J. Immunol., 28, 582–588 (1998)); and CCR-10 (or "CKR-10" or "CC-CKR-10") [MCP-1, MCP-3] (Bonini et al, DNA and Cell Biol., 16, 1249–1256 (1997)).

In addition to the mammalian chemokine receptors, mammalian cytomegaloviruses, herpesviruses and poxviruses have been shown to express, in infected cells, proteins with the binding properties of chemokine receptors (reviewed by Wells and Schwartz, Curr. Opin. Biotech., 8, 741–748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR3 expressing cells by HIV or in preventing the manipulation of immune cellular responses by viruses such as cytomegaloviruses.

A substantial body of art has accumulated over the past several decades with respect to substituted piperidines, piperizinones and pyrrolidines. These compounds have implicated in the treatment of a variety of disorders.

WO 98/25604 describes spiro-substituted azacycles which are useful as modulators of chemokine receptors:

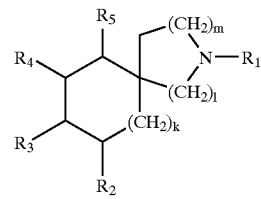

wherein $R_1$ is $C_{1-6}$ alkyl, optionally substituted with functional groups such as —$NR^6CONHR^7$, wherein $R^6$ and $R^7$ may be phenyl further substituted with hydroxy, alkyl, cyano, halo and haloalkyl. Such Spiro compounds are not considered part of the present invention.

WO 95/13069 is directed to certain piperidine, pyrrolidine, and hexahydro-1H-azepine compounds of general formula:

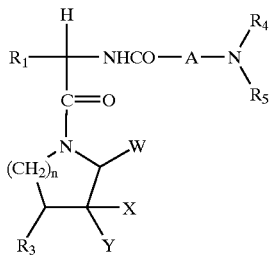

wherein A may be substituted alkyl or Z-substituted alkyl, with Z=NR$_{6a}$ or O. Compounds of this type are claimed to promote the release of growth hormone in humans and animals.

U.S. Pat. No. 5,753,654 discloses Gastrointestinal prokinetic agents for the treatment of digestive tract diseases directed toward compounds of the general formula:

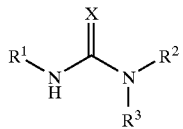

wherein R$^1$ is H, cycloalkyl, alkyl and others, R$^2$ is a group of several different heterocycles optionally linked via methylenes, and R$^3$ is H, alkyl, and others.

WO 01/68604 is directed to such cyclic ring systems including piperidines, pyrrolidine and morpholine compounds of general formula:

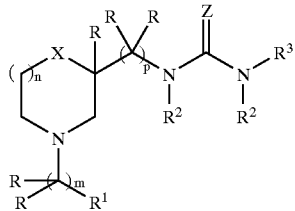

wherein R3 may be substituted alkyl, aryl, alkenyl, and others and R$^1$ may be substituted with H, alkenyl, (hetero) aryl, (hetero)aralkyl, and others. Compounds of this type are claimed as ligands for various cellular receptors including opioid receptors, other G-protein-coupled receptors and analgesics.

U.S. Pat. No. 5,668,151 discloses Neuropeptide Y (NPY) antagonists comprising 1,4-dihydropyridines with a piperidinyl or tetrahydropyridinyl-containing moiety attached to the 3-position of the 4-phenyl ring:

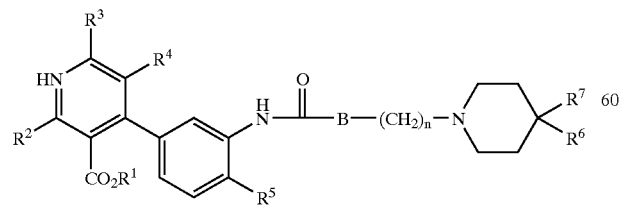

wherein B may be NH, NR$^1$, O, or a bond, and R$^7$ may be substituted phenyl, benzyl, phenethyl and the like.

Patent publication EP 0 903 349 A2 discloses CCR-3 receptor antagonists comprising cyclic amines of the following structure:

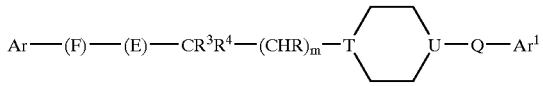

wherein T and U may be both nitrogen or one of T and U is nitrogen and the other is carbon and E may be —NR$^6$CONR$^5$— and others.

WO 97/27752 discloses compounds of the general formula:

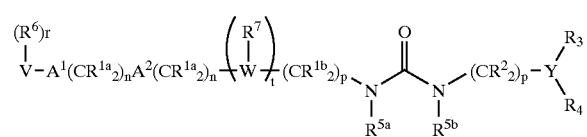

wherein W may be a pyrazole ring. These compounds are claimed to treat cancer as inhibitors of farnesyl-protein transferase.

WO 99/04794 is directed towards modulators of chemokine activity having the general formula:

wherein the claimed compounds are para-substituted piperidines.

WO 94/22846 discloses compounds having the general formula:

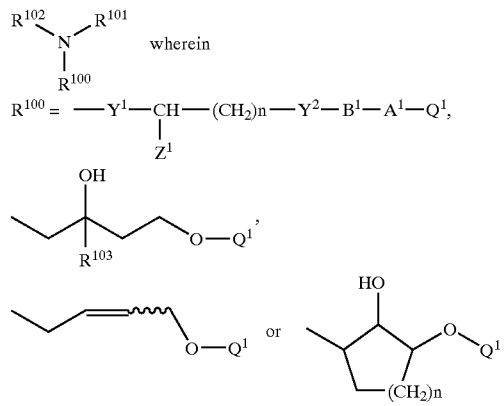

and optionally having the R$^{101}$ and R$^{102}$ connected to form a heterocycle ring. These compounds are disclosed as agents for sensitizing tumor cells or as anti cancer agents.

PCT publications WO 00/35451 and WO 01/98269 discloses compounds having the general formula

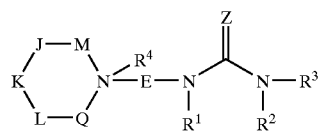

wherein the compounds are modulators of chemokine receptor activity.

These reference compounds are readily distinguished structurally by the present invention. The prior art does not disclose nor suggest the unique combination of structural fragments which embody these novel piperidines as having activity toward the chemokine receptors.

SUMMARY OF THE INVENTION

Accordingly, the present invention provides novel agonists or antagonists of CCR-3, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating inflammatory diseases and allergic disorders comprising administering to a host in need of such treatment a therapeutically effective amount of at least one of the compounds of the present invention or a pharmaceutically acceptable salt or prodrug form thereof.

The present invention provides novel N-substituted heterocyclic amines for use in therapy.

Further, the present invention provides the use of novel N-substituted heterocyclic amines for the manufacture of a medicament for the treatment of allergic disorders.

These and other aspects, which will become apparent during the following detailed description, have been achieved by the inventors' discovery that compounds of formula (I):

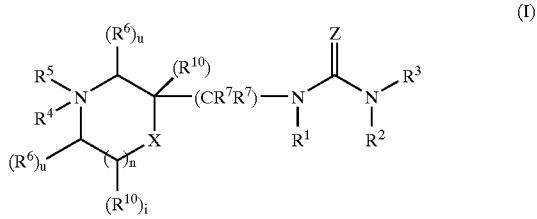

or stereoisomers or pharmaceutically acceptable salts thereof, wherein X, Z, $R^1$, $R^2$, $R^3$, $R^4$, $R^5$, $R^6$, $R^7$, $R^{10}$, i, n, and u are defined below, and are effective modulators of chemokine activity.

DETAILED DESCRIPTION OF PREFERRED EMBODIMENTS

[1] In one embodiment, the present invention provides novel compounds of formula (I):

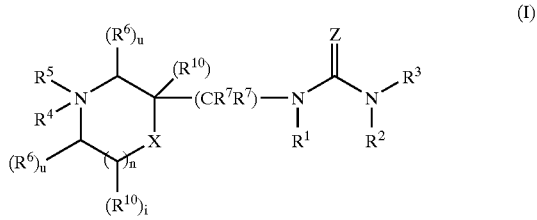

or stereoisomers or pharmaceutically acceptable salts thereof, wherein:

Z is selected from O, S, $N(R^d)$, $C(CN)_2$, $CH(NO_2)$, and CH(CN);

X is $C(R^8)(R^9)$;

$R^1$ and $R^2$ are independently selected from H, $C_{1-8}$ alkyl, $C_{2-8}$ alkenyl, and $C_{2-8}$ alkynyl;

$R^d$ is selected from H, $C_1-C_6$ alkyl, $C_3-C_6$ cycloalkyl, $CON(R^f)R^f$, $OR^e$, CN, $NO_2$, and $(CH_2)_r$-phenyl substituted with 0–3 $R^{18}$;

$R^e$, at each occurrence, is independently selected from H, $C_{1-6}$ alkyl, $C_{3-6}$ cycloalkyl, and phenyl substituted with 0–3 $R^{18}$;

$R^f$, at each occurrence, is independently selected from H, $C_{1-6}$ alkyl, $C_{3-6}$ cycloaklyl, and phenyl substituted with 0–3 $R^{18}$, or optionally, two $R^f$ may be taken together with the nitrogen to which both are attached to form a pyrrolidine, piperidine, piperazine or morpholine ring;

$R^3$ is selected from a $(CR^{3'}R^{3'})_r$—$C_{3-6}$ carbocyclic residue substituted with 0–5 $R^{15}$ and a $(CR^{3'}R^{3'})_r$-5–10 membered heterocyclic system containing 1–4 heteroatoms selected from N, O, and S, substituted with 0–3 $R^{15}$, with the proviso that the heterocyclic residue is not cyclopheptimidazolyl;

$R^{3'}$, at each occurrence, is independently selected from H, $C_{1-6}$ alkyl, $(CH_2)_rC_{3-6}$ cycloalkyl, and phenyl;

$R^4$ is absent, taken with the nitrogen to which it is attached to form an N-oxide, or selected from $C_{1-8}$ alkyl, $C_{2-8}$ alkenyl, $C_{2-8}$ alkynyl, $(CH_2)_rC_{3-6}$ cycloalkyl, $(CH_2)_qC(O)R^{4b}$, $(CH_2)_qC(O)NR^{4a}R^{4a}$, $(CH_2)_qC(O)OR^{4b}$, and a $(CH_2)_r$—$C_{3-6}$ carbocyclic residue substituted with 0–3 $R^{4c}$;

$R^{4a}$, at each occurrence, is independently selected from H, $C_{1-6}$ alkyl, $(CH_2)_rC_{3-6}$ cycloalkyl, and phenyl;

$R^{4b}$, at each occurrence, is independently selected from $C_{1-6}$ alkyl, $C_{2-8}$ alkenyl, $(CH_2)_rC_{3-6}$ cycloalkyl, $C_{2-8}$ alkynyl, and phenyl;

$R^{4c}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{4a}R^{4a}$, and $(CH_2)_r$phenyl;

$R^5$ is selected from

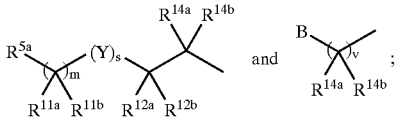

Y is selected from O, $N(R^{25})$, S, S(O), and $S(O)_2$;

ring B is a 5–7 membered cycloalkyl ring optionally containing a C=O, and being substituted with 0–2 $R^{11a}$, wherein the cycloalkyl is fused with a benzo group substituted with 0–3 $R^{16}$ or is fused with a 5–6 membered aromatic heterocyclic ring having 0–3 N, 0–1 O, or 0–1 S, the heterocyclic ring being substituted with 0–3 $R^{16}$;

alternatively, ring B is a fused 5–7 membered saturated heterocyclic ring containing 0–1 O, $N(R^{16})$, S, S(O), and $S(O)_2$, substituted with 0–2 $R^{11a}$, the heterocyclic ring being fused with a benzo group substituted with 0–3 $R^{16}$ or is fused with a 5–6 membered heterocyclic ring having 0–3 N, 0–1 O, or 0–1 S, the heterocyclic ring being substituted with 0–3 $R^{16}$;

provided that if ring B is a heterocyclic ring, then the number of carbon atoms separating the heteroatom of ring B and the nitrogen atom of structure (I) bonded to $R^5$ is at least 2;

$R^{5a}$ is selected from a $C_{3-10}$ carbocyclic residue substituted with 0–5 $R^{16}$, and a 5–10 membered heterocyclic residue containing 1–4 heteroatoms selected from N, O, and S, substituted with 0–3 $R^{16}$;

$R^6$, at each occurrence, is independently selected from $C_{1-6}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rNR^{6a}R^{6a}$, $(CH_2)_qOH$, $(CH_2)_q OR^{6b}$, $(CH_2)_qSH$, $(CH_2)_qSR^{6b}$, $(CH_2)_rC(O)OH$, $(CH_2)_r C(O)R^{6b}$, $(CH_2)_rC(O)NR^{6a}R^{6a}$, $(CH_2)_qNR^{6d}C(O)R^{6a}$, $(CH_2)_rC(O)OR^{6b}$, $(CH_2)_qOC(O)R^{6b}$, $(CH_2)_rS(O)_pR^{6b}$, $(CH_2)_rS(O)_2NR^{6a}R^{6a}$, $(CH_2)_rNR^{6d}S(O)_2R^{6b}$, and $(CH_2)_r$ phenyl substituted with 0–3 $R^{6c}$;

$R^{6a}$, at each occurrence, is independently selected from H, $C_{1-6}$ alkyl, $C_{3-6}$ cycloalkyl, and phenyl substituted with 0–3 $R^{6c}$;

$R^{6b}$, at each occurrence, is independently selected from $C_{1-6}$ alkyl, $C_{3-6}$ cycloalkyl, and phenyl substituted with 0–3 $R^{6c}$;

$R^{6c}$, at each occurrence, is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is independently selected from H, $C_{1-6}$ alkyl, and $C_{3-6}$ cycloalkyl;

$R^7$, at each occurrence, is independently selected from H, $C_{1-6}$ alkyl, $C_{2-8}$ alkenyl, $C_{2-8}$ alkynyl, $(CH_2)_qOH$, $(CH_2)_q SH$, $(CH_2)_qOR^{7d}$, $(CH_2)_qSR^{7d}$, $(CH_2)_qNR^{7a}R^{7a}$, $(CH_2)_r C(O)OH$, $(CH_2)_rC(O)R^{7b}$, $(CH_2)_rC(O)NR^{7a}R^{7a}$, $(CH_2)_q NR^{7a}C(O)R^{7a}$, $(CH_2)_qNR^{7a}C(O)H$, $(CH_2)_rC(O)OR^{7b}$, $(CH_2)_qOC(O)R^{7b}$, $(CH_2)_qS(O)_pR^{7b}$, $(CH_2)_qS(O)_2 NR^{7a}R^{7a}$, $(CH_2)_qNR^{7a}S(O)_2R^{7b}$, $C_{1-6}$ haloalkyl, a $(CH_2)_r$—$C_{3-6}$ carbocyclic residue substituted with 0–3 $R^{7c}$, and a $(CH_2)_r$-5–10 membered heterocyclic system containing 1–4 heteroatoms selected from N, O, and S, substituted with 0–2 $R^{7c}$;

$R^{7a}$, at each occurrence, is independently selected from H, $C_{1-6}$ alkyl, $C_{2-8}$ alkenyl, $C_{2-8}$ alkynyl, a $(CH_2)_r$—$C_{3-6}$ carbocyclic residue substituted with 0–5 $R^{7e}$, and a $(CH_2)_r$- 5–10 membered heterocyclic system containing 1–4 heteroatoms selected from N, O, and S, substituted with 0–3 $R^{7e}$;

$R^{7b}$, at each occurence, is independently selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{7e}$, and a $(CH_2)_r$-5–6 membered heterocyclic system containing 1–4 heteroatoms selected from N, O, and S, substituted with 0–3 $R^{7e}$;

$R^{7c}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{7f}R^{7f}$, $(CH_2)_r OH$, $(CH_2)_rOC_{1-4}$ alkyl, $(CH_2)_rSC_{1-4}$ alkyl, $(CH_2)_rC(O)OH$, $(CH_2)_rC(O)R^{7b}$, $(CH_2)_rC(O)NR^{7f}R^{7f}$, $(CH_2)_rNR^{7f}C(O)R^{7a}$, $(CH_2)_rC(O)OC_{1-4}$ alkyl, $(CH_2)_rOC(O)R^{7b}$, $(CH_2)_rC(=NR^{7f})NR^{7f}R^{7f}$, $(CH_2)_rS(O)_pR^{7b}$, $(CH_2)_rNHC(=NR^{7f})NR^{7f}R^{7f}$, $(CH_2)_rS(O)_2NR^{7f}R^{7f}$, $(CH_2)_rNR^{7f}S(O)_2 R^{7b}$, and $(CH_2)_r$phenyl substituted with 0–3 $R^{7e}$;

$R^{7d}$, at each occurrence, is independently selected from $C_{1-6}$ alkyl substituted with 0–3 $R^{7e}$, alkenyl, alkynyl, and a $C_{3-6}$ carbocyclic residue substituted with 0–3 $R^{7c}$;

$R^{7e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{7f}$, at each occurrence, is independently selected from H, $C_{1-6}$ alkyl, and $C_{3-6}$ cycloalkyl;

$R^8$ is selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_r C(O)OH$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_rOC(O) R^{19}$, $(CH_2)_rS(O)R^{19}$, $(CH_2)_rS(O)_2R^{19}$, $(CH_2)_rS(O)_2N (R^{18a})R^{18b}$, $(CH_2)_rN(R^{18c})S(O)_2R^{19}$, a $(C(R^{8a})(R^{8b}))_r$— $C_{3-10}$ carbocyclic residue substituted with 0–5 $R^{17}$, and a $(C(R^{8a})(R^{8b}))_r$-5–10 membered heterocyclic system containing 1–4 heteroatoms selected from N, O, and S, substituted with 0–3 $R^{17}$;

$R^{8a}$ and $R^{8b}$, at each occurrence, are independently selected from H, $C_{1-6}$ alkyl, $(CH_2)_rC_{3-6}$ cycloalkyl, and $(CH_2)_r$ phenyl substituted with 0–3 $R^{18}$;

$R^9$ is selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_qN(R^{18a})R^{18b}$, $(CH_2)_qOH$, $(CH_2)_qOR^{19}$, $(CH_2)_qSH$, $(CH_2)_qSR^{19}$, $(CH_2)_q C(O)OH$, $(CH_2)_qC(O)R^{19}$, $(CH_2)_qC(O)N(R^{18a})R^{18b}$, $(CH_2)_qN(R^{18c})C(O)R^{19}$, $(CH_2)_qC(O)OR^{19}$, $(CH_2)_qOC (O)R^{19}$, $(CH_2)_qS(O)R^{19}$, $(CH_2)_qS(O)_2R^{19}$, $(CH_2)_qS(O)_2N (R^{18a})R^{18b}$, $(CH_2)_qN(R^{18c})S(O)_2R^{19}$, a $(C(R^{8a})(R^{8b}))_r$— $C_{3-10}$ carbocyclic residue substituted with 0–5 $R^{17}$, and a $(C(R^{8a})(R^{8b}))_r$-5–10 membered heterocyclic system containing 1–4 heteroatoms selected from N, O, and S, substituted with 0–3 $R^{17}$;

alternatively, $R^8$ and $R^9$ taken together are selected from =O, =S, =$NR^{9a}$;

$R^{9a}$ is selected from H, $C_{1-6}$ alkyl, $C_{2-8}$ alkenyl, $C_{2-8}$ alkynyl, $(CH_2)_rC_{3-6}$ cycloalkyl, $(CH_2)_rOH$, $(CH_2)_rOC_{1-6}$ alkyl, $(CH_2)_rC(O)R^{19}$, $(CH_2)_rC(O)N(R^{18a})R^{18b}$, $(CH_2)_r C(O)OR^{19}$, $(CH_2)_rS(O)_2R^{19}$, $(CH_2)_rS(O)_2N(R^{18a})R^{18b}$, and $(CH_2)_r$phenyl substituted with 0–3 $R^{17}$;

$R^{9b}$, at each occurrence are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_rC(O)OH$, $(CH_2)_rC(O)R^{19}$, $(CH_2)_rC(O)N(R^{18a})R^{18b}$, $(CH_2)_rN(R^{18c}) C(O)R^{19}$, $(CH_2)_rC(O)OR^{19}$, $(CH_2)_rOC(O)R^{19}$, $(CH_2)_rS (O)R^{19}$, $(CH_2)_rS(O)_2R^{19}$, $(CH_2)_rS(O)_2N(R^{18a})R^{18b}$, $(CH_2)_rN(R^{18c})S(O)_2R^{19}$, and $(CH_2)_r$phenyl substituted with 0–3 $R^{17}$;

$R^{10}$, at each occurrence, is independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rNR^{10a}R^{10a}$, $(CH_2)_r OH$, $(CH_2)_rOR^{10b}$, $(CH_2)_rSH$, $(CH_2)_rSR^{10b}$, $(CH_2)_rC(O) OH$, $(CH_2)_rC(O)R^{10b}$, $(CH_2)_rC(O)NR^{10a}R^{10a}$, $(CH_2)_r NR^{10d}C(O)R^{10a}$, $(CH_2)_rC(O)OR^{10b}$, $(CH_2)_rOC(O)R^{10b}$, $(CH_2)_rS(O)_pR^{10b}$, $(CH_2)_rS(O)_2NR^{10a}R^{10a}$, $(CH_2)_r NR^{10d}S(O)_2R^{10b}$, and $(CH_2)_r$phenyl substituted with 0–3 $R^{10c}$;

$R^{10a}$, at each occurrence, is independently selected from H, $C_{1-6}$ alkyl, $C_{3-6}$ cycloalkyl, and phenyl substituted with 0–3 $R^{10c}$;

$R^{10b}$, at each occurrence, is independently selected from $C_{1-6}$ alkyl, $C_{3-6}$ cycloalkyl, and phenyl substituted with 0–3 $R^{10c}$;

$R^{10c}$, at each occurrence, is independently selected from $C_{1-6}$ alkyl, $C_{3-6}$ cycloalkyl, Cl, F, Br, I, CN, $NO_2$, $(CF_2)_r CF_3$, $(CH_2)_rOC_{1-5}$ alkyl, $(CH_2)_rOH$, $(CH_2)_rSC_{1-5}$ alkyl, and $(CH_2)_rNR^{10d}R^{10d}$;

$R^{10d}$, at each occurrence, is independently selected from H, $C_{1-6}$ alkyl, and $C_{3-10}$ cycloalkyl;

$R^{11a}$ and $R^{12a}$, at each occurrence are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_rC(O)OH$, $(CH_2)_rC(O)R^{19}$, $(CH_2)_rC(O)N(R^{18a})R^{18b}$, $(CH_2)_rN(R^{18c}) C(O)R^{19}$, $(CH_2)_rC(O)OR^{19}$, $(CH_2)_rOC(O)R^{19}$, $(CH_2)_rS (O)R^{19}$, $(CH_2)_rS(O)_2R^{19}$, $(CH_2)_rS(O)_2N(R^{18a})R^{18b}$, $(CH_2)_rN(R^{18c})S(O)_2R^{19}$, and $(CH_2)_r$phenyl substituted with 0–3 $R^{18}$;

$R^{11b}$, $R^{12b}$, $R^{14a}$ and $R^{14b}$ at each occurrence are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_qN$ $(R^{18a})R^{18b}$, $(CH_2)_qOH$, $(CH_2)_qOR^{19}$, $(CH_2)_qSH$, $(CH_2)_q$ $SR^{19}$, $(CH_2)_rC(O)OH$, $(CH_2)_rC(O)R^{19}$, $(CH_2)_rC(O)N(R^{18a})R^{18b}$, $(CH_2)_qN(R^{18c})C(O)R^{19}$, $(CH_2)_rC(O)OR^{19}$, $(CH_2)_qOC(O)R^{19}$, $(CH_2)_qS(O)R^{19}$, $(CH_2)_qS(O)_2R^{19}$, $(CH_2)_qS(O)_2N(R^{18a})R^{18b}$, $(CH_2)_qN(R^{18c})S(O)_2R^{19}$, and $(CH_2)_r$phenyl substituted with 0–3 $R^{18}$;

alternatively, $R^{11a}$ and $R^{11b}$ taken together are seleted form =O, or =NOH, or alternatively, $R^{12a}$ and $R^{12b}$ taken together are seleted form =O, or =NOH;

$R^{15}$, at each occurrence, is independently selected from $C_{1-8}$ alkyl, $(CH_2)_rC_{3-6}$ cycloalkyl, Cl, Br, I, F, $NO_2$, CN, $(CHR')_rNR^{15a}R^{15a}$, $(CHR')_rOH$, $(CHR')_rOH$, $(CHR')_rR^{15d}$, $(CHR')_rSH$, $(CHR')_rC(O)H$, $(CHR')_rS(CHR')_rR^{15d}$, $(CHR')_rC(O)OH$, $(CHR')_rC(O)(CHR')_rR^{15b}$, $(CHR')_rC(O)NR^{15a}R^{15a}$, $(CHR')_rNR^{15f}C(O)(CHR')_rR^{15b}$, $(CHR')_rNR^{15f}C(O)NR^{15f}R^{15f}$, $(CHR')_rC(O)O(CHR')_rR^{15d}$, $(CHR')_rOC(O)(CHR')_rR^{15b}$, $(CHR')_rC(=NR^{15f})NR^{15a}R^{15a}$, $(CHR')_rNHC(=NR^{15f})NR^{15f}R^{15f}$, $(CHR')_rS(O)p(CHR')_rR^{15b}$, $(CHR')_rS(O)_2NR^{15a}R^{15a}$, $(CHR')_rNR^{15f}S(O)_2(CHR')_rR^{15b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 $R^{15e}$, and a $(CH_2)_r$-5–10 membered heterocyclic system containing 1–4 heteroatoms selected from N, O, and S, substituted with 0–2 $R^{15e}$;

R', at each occurrence, is independently selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with $R^{15e}$;

$R^{15a}$, at each occurrence, are selected from H, $C_{1-6}$ alkyl, $C_{2-8}$ alkenyl, $C_{2-8}$ alkynyl, a $(CH_2)_r$—$C_{3-6}$ carbocyclic residue substituted with 0–5 $R^{15e}$, and a $(CH_2)_r$-5–10 membered heterocyclic system containing 1–4 heteroatoms selected from N, O, and S, substituted with 0–2 $R^{15e}$;

$R^{15b}$, at each occurrence, is independently selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{15e}$, and $(CH_2)_r$-5–6 membered heterocyclic system containing 1–4 heteroatoms selected from N, O, and S, substituted with 0–2 $R^{15e}$;

$R^{15d}$, at each occurrence, is independently selected from $C_{2-8}$ alkenyl, $C_{2-8}$ alkynyl, $C_{1-6}$ alkyl substituted with 0–3 $R^{15e}$, a $(CH_2)_r$—$C_{3-6}$ carbocyclic residue substituted with 0–3 $R^{15e}$, and a $(CH_2)_r$-5–6 membered heterocyclic system containing 1–4 heteroatoms selected from N, O, and S, substituted with 0–3 $R^{15e}$;

$R^{15e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{15f}R^{15f}$, and $(CH_2)_r$phenyl;

$R^{15f}$, at each occurrence, is independently selected from H, $C_{1-6}$ alkyl, $C_{3-6}$ cycloalkyl, and phenyl;

$R^{16}$, at each occurrence, is independently selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a}$, $(CHR')_rOH$, $(CHR')_rO(CHR')_rR^{16d}$, $(CHR')_rSH$, $(CHR')_rC(O)H$, $(CHR')_rS(CHR')_rR^{16d}$, $(CHR')_rC(O)OH$, $(CHR')_rC(O)(CHR')_rR^{16b}$, $(CHR')_rC(O)NR^{16a}R^{16a}$, $(CHR')_rNR^{16f}C(O)(CHR')_rR^{16b}$, $(CHR')_rC(O)O(CHR')_rR^{16d}$, $(CHR')_rOC(O)(CHR')_rR^{16b}$, $(CHR')_rC(=NR^{16f})NR^{16a}R^{16a}$, $(CHR')_rNHC(=NR^{16f})NR^{16f}R^{16f}$, $(CHR')_rS(O)_p(CHR')_rR^{16b}$, $(CHR')_rS(O)_2NR^{16a}R^{16a}$, $(CHR')_rNR^{16f}S(O)_2(CHR')_rR^{16b}$, $C_{1-6}$ haloalkyl, $C_{2-8}$ alkenyl substituted with 0–3 R', $C_{2-8}$ alkynyl substituted with 0–3 R', and $(CHR')_r$ phenyl substituted with 0–3 $R^{16e}$;

$R^{16a}$, at each occurrence, is independently selected from H, $C_{1-6}$ alkyl, $C_{2-8}$ alkenyl, $C_{2-8}$ alkynyl, a $(CH_2)_r$—$C_{3-6}$ carbocyclic residue substituted with 0–5 $R^{16e}$, and a $(CH_2)_r$-5–10 membered heterocyclic system containing 1–4 heteroatoms selected from N, O, and S, substituted with 0–2 $R^{16e}$;

$R^{16b}$, at each occurrence, is independently selected from $C_{1-6}$ alkyl, $C_{2-8}$ alkenyl, $C_{2-8}$ alkynyl, a $(CH_2)_rC_{3-6}$ carbocyclic residue substituted with 0–3 $R^{16e}$, and a $(CH_2)_r$-5–6 membered heterocyclic system containing 1–4 heteroatoms selected from N, O, and S, substituted with 0–2 $R^{16e}$;

$R^{16d}$, at each occurrence, is independently selected from $C_{2-8}$ alkenyl, $C_{2-8}$ alkynyl, $C_{1-6}$ alkyl substituted with 0–3 $R^{16e}$, a $(CH_2)_r$—$C_{3-6}$ carbocyclic residue substituted with 0–3 $R^{16e}$, and a $(CH_2)_r$-5–6 membered heterocyclic system containing 1–4 heteroatoms selected from N, O, and S, substituted with 0–3 $R^{16e}$;

$R^{16e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{16f}R^{16f}$, and $(CH_2)_r$phenyl;

$R^{16f}$, at each occurrence, is independently selected from H, $C_{1-5}$ alkyl, and $C_{3-6}$ cycloalkyl, and phenyl;

$R^{17}$ at each occurrence is independently selected from =O, $C_{1-6}$ alkyl, $(CH_2)_rC_{3-6}$ cycloalkyl, Cl, F, Br, I, CN, $NO_2$, $(CH_2)_rOR^{19}$, $(CH_2)_rOH$, $(CH_2)_rSR^{19}$, $(CH_2)_rS(O)R^{19}$, $(CH_2)_rS(O)_2R^{19}$, $(CH_2)_rS(O)_2N(R^{18a})R^{18b}$, $(CH_2)_rN(R^{18c})C(O)R^{19}$, $(CH_2)_rN(R^{18c})S(O)_2R^{19}$, $(CH_2)_rC(O)OH$, $(CH_2)_rC(O)OR^{19}$, $(CH_2)_rC(O)N(R^{18a})R^{18b}$, $(CH_2)_rN(R^{18c})C(O)N(R^{18a})R^{18b}$, $(CH_2)_rN(R^{18c})C(O)OR^{19}$, $(CH_2)_rOC(O)N(R^{18a})R^{18b}$, $(CH_2)_rN(R^{18a})R^{18b}$, $C_{1-6}$ haloalkyl, $C_{2-8}$ alkenyl substituted with 0–3 $R^{17a}$, $C_{2-8}$ alkynyl substituted with 0–3 $R^{17a}$, $(CH(R^{17a}))_r$phenyl substituted with 1–3 $R^{18}$, and $(CH(R^{17a}))_r$-5–10 membered heterocyclic system containing 1–4 heteroatoms selected from N, O, and S, substituted with 0–2 $R^{18}$;

$R^{17a}$ at each occurrence is independently selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with 0–3 $R^{18}$;

$R^{18}$ at each occurrence is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rS(O)C_{1-5}$ alkyl, $(CH_2)_rS(O)_2C_{1-5}$ alkyl, $(CH_2)_rS(O)_2N(R^{18a})R^{18b}$, $(CH_2)_rN(R^{18c})C(O)C_{1-5}$ alkyl $(CH_2)_rN(R^{18c})S(O)_2C_{1-5}$ alkyl, $(CH_2)_rC(O)N(R^{18a})R^{18b}$, $(CH_2)_rC(O)OC_{1-5}$ alkyl, $(CH_2)_rC(O)C_{1-5}$ alkyl, and $(CH_2)_rN(R^{18a})R^{18b}$;

$R^{18a}$, $R^{18b}$, and $R^{18c}$ at each occurrence are independently selected from H, $C_{1-6}$ alkyl, and $C_{3-6}$ cycloalkyl;

$R^{19}$ at each occurrence is independently selected from $C_{1-6}$ alkyl, $C_{3-6}$ cycloalkyl, and phenyl substituted with 0–3 $R^{18}$;

alternatively, $R^{18a}$ and $R^{18b}$ along with the nitrogen to which both are attached form a pyrrolidine, piperidine, piperazine or morpholine ring;

$R^{25}$ at each occurrence is independently selected from H, $C_{1-6}$ alkyl, $C_{2-8}$ alkenyl, $C_{2-8}$ alkynyl, $(CH_2)_rC_{3-6}$ cycloalkyl, $(CH_2)_rC(O)R^{19}$, $(CH_2)_rC(O)N(R^{18a})R^{18b}$, $(CH_2)_rC(O)OR^{19}$, $(CH_2)_rS(O)_2R^{19}$, $(CH_2)_rS(O)_2N(R^{18a})R^{18b}$, and $(CH_2)_r$phenyl substituted with 0–3 $R^{17}$;

i is selected from 0, 1, and 2;

m is selected from 0, 1, and 2;

s is selected from 0 and 1;

with the proviso: m+s is selected from 0, 1, and 2;

n is selected from 1 and 2;

v is selected from 0, 1, 2, and 3;

with the proviso: that the total number of atoms between the nitrogen of which R' is attached and the fused ring B is less than or equal to 4;

r is selected from 0, 1, 2, 3, 4, and 5;
t is selected from 0, 1, 2, 3, 4, and 5;
q is selected from 1, 2, 3, 4, and 5;
p is selected from 1, 2, and 3;
u is selected from 0, 1 and, 2.

[2] In another embodiment, the present invention provides compounds of formula (I):

$R^{11a}$ and $R^{12a}$, at each occurrence are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_rC(O)OH$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_rOC(O)R^{19}$, $(CH_2)_rS(O)R^{19}$, $(CH_2)_rS(O)_2R^{19}$, $(CH_2)_rS(O)_2N(R^{18a})R^{18b}$, $(CH_2)_rN(R^{18c})S(O)_2R^{19}$ and $(CH_2)_r$phenyl substituted with 0–3 $R^{18}$; and $R^{11b}$, $R^{12b}$, $R^{14a}$ and $R^{14b}$ at each occurrence are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_qN(R^{18a})R^{18b}$, $(CH_2)_qOH$, $(CH_2)_qOR^{19}$, $(CH_2)_qSH$, $(CH_2)_qSR^{19}$, $(CH_2)_rC(O)OH$, $(CH_2)_rC(O)R^{19}$, $(CH_2)_rC(O)N(R^{18a})R^{18b}$, $(CH_2)_qN(R^{18c})C(O)R^{19}$, $(CH_2)_rC(O)OR^{19}$, $(CH_2)_qOC(O)R^{19}$, $(CH_2)_qS(O)R^{19}$, $(CH_2)_qS(O)_2R^{19}$, $(CH_2)_qS(O)_2N(R^{18a})R^{18b}$, $(CH_2)_qN(R^{18c})S(O)_2R^{19}$, and $(CH_2)_r$phenyl substituted with 0–3 $R^{18}$.

[3] In another embodiment, the present invention provides novel compounds of formula (I):
$R^1$ and $R^2$ are independently selected from H, and $C_{1-8}$ alkyl;
$R^4$ is absent, taken with the nitrogen to which it is attached to form an N-oxide, or selected from $C_{1-8}$ alkyl, $(CH_2)_r$ $C_{3-6}$ cycloalkyl, and a $(CH_2)_r$—$C_{3-6}$ carbocyclic residue substituted with 0–3 $R^{4c}$; and $R^{4c}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_r$ OH, $(CH_2)_rSC_{1-5}$ alkyl, $(CH_2)_rNR^{4a}R^{4a}$, and $(CH_2)_r$ phenyl.

[4] In another embodiment, the present invention provides novel compounds of formula (I):
Z is selected from O and S;
$R^6$, at each occurrence, is independently selected from $C_{1-4}$ alkyl, $(CH_2)_rC_{3-6}$ cycloalkyl, $(CH_2)_qNR^{6a}R^{6a}$, $(CH_2)_q$ OH, $(CH_2)_qOR^{6b}$, $(CH_2)_rC(O)OH$, $(CH_2)_rC(O)R^{6b}$, $(CH_2)_rC(O)NR^{6a}R^{6a}$, $(CH_2)_qNR^{6d}C(O)R^{6a}$; $(CH_2)_rS(O)_2$ $NR^{6a}R^{6a}$, $(CH_2)_rNR^{6d}S(O)_2R^{6b}$, and $(CH_2)_r$phenyl substituted with 0–3 $R^{6c}$;

$R^{6a}$ and $R^{6a}$, at each occurrence, are selected from H, methyl, ethyl, propyl, i-propyl, butyl, cyclopropyl, cyclopentyl, cyclohexyl, and phenyl;

$R^{6b}$, at each occurrence, is independently selected from methyl, ethyl, propyl, i-propyl, butyl, cyclopropyl, cyclopentyl, cyclohexyl, and phenyl;

$R^{6c}$, at each occurrence, is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is independently selected from H, methyl, ethyl, propyl, i-propyl, butyl, cyclopropyl, cyclopentyl, and cyclohexyl;

$R^7$, is selected from H, $C_{1-6}$ alkyl, $C_{2-8}$ alkenyl, $C_{2-8}$ alkynyl, $(CH_2)_qOH$, $(CH_2)_qOR^{7d}$, $(CH_2)_qNR^{7a}R^{7a}$, $(CH_2)_qC(O)$ $R^{7b}$, $(CH_2)_rC(O)NR^{7a}R^{7a}$, $(CH_2)_qNR^{7a}C(O)R^{7a}$, $(CH_2)_q$ $NR^{7a}C(O)H$, $(CH_2)_rC(O)OR^{7b}$, $(CH_2)_qOC(O)R^{7b}$, $C_{1-6}$ haloalkyl, a $(CH_2)_r$—$C_{3-6}$ carbocyclic residue substituted with 0–3 $R^{7c}$, and a $(CH_2)_r$-5–10 membered heterocyclic system containing 1–4 heteroatoms selected from N, O, and S, substituted with 0–2 $R^{7c}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, indazolyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^{7a}$, at each occurrence, is independently selected from H, $C_{1-6}$ alkyl, and a $(CH_2)_r$—$C_{3-6}$ carbocyclic residue substituted with 0–5 $R^{7e}$;

$R^{7b}$, at each occurrence, is independently selected from $C_{1-6}$ alkyl, a $(CH_2)_r$—$C_{3-6}$ carbocyclic residue substituted with 0–2 $R^{7e}$;

$R^{7c}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{7f}R^{7f}$, $(CH_2)_r$ OH, $(CH_2)_rOC_{1-4}$ alkyl, $(CH_2)_rSC_{1-4}$ alkyl, $(CH_2)_rC(O)$ OH, $(CH_2)_rC(O)R^{7b}$, $(CH_2)_rC(O)NR^{7f}R^{7f}$, $(CH_2)_rNR^{7f}C$ $(O)R^{7a}$, $(CH_2)_rC(O)OC_{1-4}$ alkyl, $(CH_2)_rOC(O)R^{7b}$, $(CH_2)_rC(=NR^{7f})NR^{7f}R^{7f}$, $(CH_2)_rS(O)_pR^{7b}$, $(CH_2)_rNHC$ $(=NR^{7f})NR^{7f}R^{7f}$, $(CH_2)_rS(O)_2NR^{7f}R^{7f}$, $(CH_2)_rNR^{7f}S$ $(O)_2$ $R^{7b}$, and $(CH_2)_r$phenyl substituted with 0–3 $R^{7e}$;

$R^{7d}$, at each occurrence, is independently selected from $C_{1-6}$ alkyl substituted with 0–3 $R^{7e}$, and a $C_{3-6}$ carbocyclic residue substituted with 0–3 $R^{7c}$;

$R^{7e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{7f}$, at each occurrence, is independently selected from H, methyl, ethyl, propyl, i-propyl, butyl, cyclopropyl, cyclopentyl and cyclohexyl;

$R^{10}$, at each occurrence, is independently selected from H, $C_{1-4}$ alkyl, $(CH_2)_rC_{3-6}$ cycloalkyl, $(CH_2)_rNR^{10a}R^{10a}$, $(CH_2)_rOH$, $(CH_2)_rOR^{10b}$, $(CH_2)_rC(O)OH$, $(CH_2)_rC(O)$ $R^{10b}$, $(CH_2)_rC(O)NR^{10a}R^{10a}$, $(CH_2)_rNR^{10d}C(O)R^{10a}$, $(CH_2)_rS(O)_2NR^{10a}R^{10a}$, $(CH_2)_rNR^{10d}S(O)_2R^{10b}$, and $(CH_2)_r$phenyl substituted with 0–3 $R^{10c}$;

$R^{10a}$ and $R^{10a}$, at each occurrence, are selected from H, methyl, ethyl, propyl, i-propyl, butyl, cyclopropyl, cyclopentyl, cyclohexyl, and phenyl;

$R^{10b}$, at each occurrence, is independently selected from methyl, ethyl, propyl, i-propyl, butyl, cyclopropyl, cyclopentyl, cyclohexyl, and phenyl;

$R^{10c}$, at each occurrence, is independently selected from $C_{1-10}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{10d}R^{10d}$; and $R^{10d}$, at each occurrence, is independently selected from H, methyl, ethyl, propyl, i-propyl, butyl, cyclopropyl, cyclopentyl, and cyclohexyl.

[5] In another embodiment, the present invention provides novel compounds of formula (I):
$R^3$ is selected from a $(CR^{3'}H)_r$—$C_{3-8}$ carbocyclic residue substituted with 0–5 $R^{15}$, wherein the carbocyclic residue is selected from phenyl, naphthyl, and adamantyl; and a $(CR^{3'}H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, indazolyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{5a}$ is selected from phenyl substituted with 0–5 $R^{16}$; and a heterocyclic residue substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^8$ is selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_rC(O)OH$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_rOC(O)R^{19}$, $(CH_2)_rS(O)R^{19}$, $(CH_2)_rS(O)_2R^{19}$, $(CH_2)_rS(O)_2N(R^{18a})R^{18b}$, $(CH_2)_rN(R^{18c})S(O)_2R^{19}$, a $(C(R^{8a})(R^{8b}))_r$—$C_{3-10}$ carbocyclic residue substituted with 0–5 $R^{17}$, and a $(C(R^{8a})(R^{8b}))_r$-5–10 membered heterocyclic system containing 1–4 heteroatoms selected from N, O, and S, substituted with 0–3 $R^{17}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^{8a}$ and $R^{8b}$, at each occurrence, are independently selected from H, methyl, ethyl, propyl, i-propyl, butyl, cyclopropyl, cyclopentyl, cyclohexyl, and $(CH_2)_r$phenyl substituted with 0–3 $R^{18}$;

$R^9$ is selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_qN(R^{18a})R^{18b}$, $(CH_2)_qOH$, $(CH_2)_qOR^{19}$, $(CH_2)_qSH$, $(CH_2)_qSR^{19}$, $(CH_2)_qC(O)OH$, $(CH_2)_qC(O)R^{19}$, $(CH_2)_qC(O)N(R^{18a})R^{18b}$, $(CH_2)_qN(R^{18c})C(O)R^{19}$, $(CH_2)_qC(O)OR^{19}$, $(CH_2)_qOC(O)R^{19}$, $(CH_2)_qS(O)R^{19}$, $(CH_2)_qS(O)_2R^{19}$, $(CH_2)_qS(O)_2N(R^{18a})R^{18b}$, $(CH_2)_qN(R^{18c})S(O)_2R^{19}$, a $(C(R^{8a})(R^{8b}))_r$—$C_{3-10}$ carbocyclic residue substituted with 0–5 $R^{17}$, and a $(C(R^{8a})(R^{8b}))_r$-5–10 membered heterocyclic system containing 1–4 heteroatoms selected from N, O, and S, substituted with 0–3 $R^{17}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

alternatively, $R^8$ and $R^9$ taken together are selected from =O, =S, =$NR^{9a}$;

$R^{9a}$ is selected from H, $C_{1-6}$ alkyl, $C_{2-8}$ alkenyl, $C_{2-8}$ alkynyl, $(CH_2)_rC_{3-6}$ cycloalkyl, $(CH_2)_rOH$, $(CH_2)_rOC_{1-6}$ alkyl, $(CH_2)_rC(O)R^{19}$, $(CH_2)_rC(O)N(R^{18a})R^{18b}$, $(CH_2)_rC(O)OR^{19}$, and $(CH_2)_r$phenyl substituted with 0–3 $R^{17}$; and $R^{9b}$, at each occurrence are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_rC(O)OH$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_rOC(O)R^{19}$, $(CH_2)_rS(O)R^{19}$, $(CH_2)_rS(O)_2R^{19}$, $(CH_2)_rS(O)_2N(R^{18a})R^{18b}$, $(CH_2)_rN(R^{18c})S(O)_2R^{19}$, and $(CH_2)_r$phenyl substituted with 0–3 $R^{17}$.

[6] In another embodiment, the present invention provides novel compounds of formula (I):
$R^1$ and $R^2$ are H;
$R^{5a}$ is phenyl substituted with 1–3 $R^{16}$;

$R^{16}$, at each occurrence, is independently selected from $C_{1-8}$ alkyl, $(CH_2)_rC_{3-6}$ cycloalkyl, $CF_3$, Cl, Br, I, F, $NR^{16a}R^{16a}$, $NO_2$, CN, OH, $OR^{16d}$, $C(O)R^{16b}$, $C(O)NR^{16a}R^{16a}$, and $NR^{16f}C(O)R^{16b}$;

$R^{16a}$, at each occurrence, is independently selected from H, methyl, ethyl, propyl, i-propyl, butyl, cyclopropyl, cyclopentyl, cyclohexyl, and $(CH_2)_r$phenyl substituted with 0–3 $R^{16e}$;

$R^{16b}$, at each occurrence, is independently selected from methyl, ethyl, propyl, i-propyl, butyl, cyclopropyl, cyclopentyl, cyclohexyl, and $(CH_2)_r$phenyl substituted with 0–3 $R^{16e}$;

$R^{16d}$, at each occurrence, is independently selected from methyl, ethyl, propyl, i-propyl, butyl, and phenyl;

$R^{16e}$, at each occurrence, is independently selected from methyl, ethyl, propyl, i-propyl, butyl, Cl, F, Br, I, CN, $NO_2$, $(CF_2)_rCF_3$, OH, and $(CH_2)_rOC_{1-5}$ alkyl; and $R^{16f}$, at each occurrence, is independently selected from H, methyl, ethyl, propyl, i-propyl, and butyl.

[7] In another embodiment, the present invention provides novel compounds of formula (I-i):

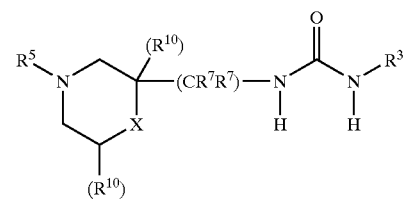

$R^{10}$ is selected from H, methyl, ethyl, propyl, i-propyl, butyl, OH, and $OR^{10b}$; and $R^{10b}$ is selected from methyl, ethyl, propyl, i-propyl, and butyl.

[8] In another embodiment, the present invention provides novel compounds of formula (I) or formula (I-i):
$R^5$ is

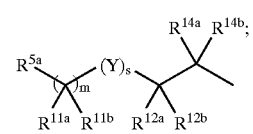

$R^{11a}$ and $R^{12a}$, at each occurrence are independently selected from H, methyl, ethyl, propyl, i-propyl, butyl, pentyl, hexyl, cyclopropyl, cyclopentyl, cylohexyl, $CF_3$, $(CH_2)_rN(R^{18a})R^{18b}$, $(CH_2)_rOH$;

$R^{11b}$, $R^{12b}$, $R^{14a}$ and $R^{14b}$ at each occurrence are independently selected from H, methyl, ethyl, propyl, i-propyl, butyl, pentyl, hexyl, cyclopropyl, cyclopentyl, cylohexyl, $CF_3$, $(CH_2)_{rq}N(R^{18a})R^{18b}$, $(CH_2)_{rq}OH$;

$R^{25}$ at each occurrence is independently selected from H, methyl, ethyl, propyl, i-propyl, butyl, cyclopropyl, cyclopentyl, cyclohexyl, $(CH_2)_rC(O)R^{19}$, $(CH_2)_rC(O)N(R^{18a})R^{18b}$, $(CH_2)_rC(O)OR^{19}$, and $(CH_2)_r$phenyl substituted with 0–3 $R^{17}$.

[9] In another embodiment, the present invention provides novel compounds of formula (I) or formula (I-i):

$R^5$ is

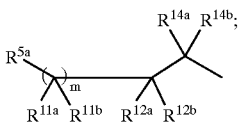

$R^7$, at each occurrence, is selected from H, methyl, ethyl, propyl, i-propyl, butyl, $(CH_2)_qOH$;

$R^{11a}$ and $R^{12a}$, at each occurrence, are independently selected from H, methyl, and ethyl;

$R^{11b}$, $R^{12b}$, $R^{14a}$, and $R^{14b}$, at each occurrence, are independently selected from H, methyl, ethyl and OH; and $R^{16}$, at each occurrence, is independently selected from methyl, Cl, F, $CF_3$, and CN.

[10] In another embodiment, the present invention provides novel compounds of formula (I) or formula (I-i):
$R^5$ is

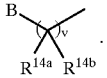

[10] In another embodiment, the present invention provides novel compounds of formula (I) or formula (I-i):
$R^8$ and $R^9$ do not both equal H.

[11] In another embodiment, the present invention provides novel compounds of formula (I), wherein the compound is selected form the compounds of Table 1 or:

1-{1-[3-(4-fluorophenyl)-2,2-dimethylpropyl]-piperidin-3-ylmethyl}-3-[3-(1-methyl-1H-tetrazol-5-yl)-phenyl]-urea;

1-{1-[3-(4-fluorophenyl)-propyl]-piperidin-3-ylmethyl}-3-[3-(1-methyl-1H-tetrazol-5-yl)-phenyl]-urea;

1-[3-(1-methyl-1H-tetrazol-5-yl)-phenyl]-3-{1-[2-(4-trifluoromethylphenyl)-ethyl]-piperidin-3-ylmethyl}-urea;

1-(5-acetyl-4-methylthiazol-2-yl)-3-{1-[2-(4-fluorophenyl)ethyl]-piperidin-3-ylmethyl}urea;

1-[3-ethyl-5-(1-methyl-1H-tetrazol-5-yl)phenyl]-3-{trans-1-[2-(4-fluorophenyl)-ethyl]-4-methylpiperidin-3-ylmethyl}-urea;

1-[3-(1-methyl-1H-tetrazol-5-yl)phenyl]-3-{cis-1-[2-(4-fluorophenyl)-ethyl]-4-methylpiperidin-3-ylmethyl}-urea;

trans-1-{4-(benzyl-methylamino)-1-[2-(4-fluorophenyl)-ethyl]-piperidin-3-ylmethyl}-3-[3-ethyl-5-(1-methyl-1H-tetrazol-5-yl)-phenyl]-urea;

trans-1-{4-methylamino-1-[2-(4-fluorophenyl)-ethyl]-piperidin-3-ylmethyl}-3-[3-ethyl-5-(1-methyl-1H-tetrazol-5-yl)-phenyl]-urea;

trans-N-{3-{3-[3-ethyl-5-(1-methyl-1H-tetrazol-5-yl)-phenyl]-ureidomethyl}-1-[3-(4-fluoro-phenyl)-propyl]-piperidin-4-yl}-N-methyl-acetamide;

trans-N-{3-{3-[3-ethyl-5-(1-methyl-1H-tetrazol-5-yl)-phenyl]-ureidomethyl}-1-[3-(4-fluoro-phenyl)-propyl]-piperidin-4-yl}-N-methyl-methanesulfonamide;

(S)-1-[3-ethyl-5-(1-methyl-1H-tetrazol-5-yl)-phenyl]-3-{1-[2-(4-fluorophenyl)-2-oxo-ethyl]-piperidin-3-ylmethyl}-urea;

(S)-1-[3-ethyl-5-(1-methyl-1H-tetrazol-5-yl)-phenyl]-3-{1-[2-(4-fluorophenyl)-2-hydroxyimino-ethyl]-piperidin-3-ylmethyl}-urea;

1-[3-ethyl-5-(1-methyl-1H-tetrazol-5-yl)-phenyl]-3-{1-[2-(4-fluorophenyl)-2-(RS)-hydroxyethyl]-(S)-piperidin-3-ylmethyl}-urea;

(S)-1-[3-ethyl-5-(1-methyl-1H-tetrazol-5-yl)-phenyl]-3-{1-[2-(4-fluorophenyl)-ethyl]-piperidin-3-ylmethyl}-urea;

1-[3-ethyl-5-(1-methyl-1H-tetrazol-5-yl)phenyl]-3-{1-[2-(4-fluorophenyl)-ethyl]-4-ethylpiperidin-3-ylmethyl}-urea; and 1-[3-ethyl-5-(1-methyl-1H-tetrazol-5-yl)phenyl]-3-{1-[2-(4-fluorophenyl)-ethyl]-4,4-dimethylpiperidin-3-ylmethyl}-urea.

In another embodiment, the present invention provides a pharmaceutical composition, comprising a pharmaceutically acceptable carrier and a therapeutically effective amount of a compound of the present invention.

In another embodiment, the present invention provides a method for modulation of chemokine receptor activity comprising administering to a patient in need thereof a therapeutically effective amount of a compound of the present invention.

In another embodiment, the present invention provides a method for treating or preventing asthma, comprising administering to a patient in need thereof a therapeutically effective amount of a compound of the present invention.

In another embodiment, the modulation of chemokine receptor activity comprises contacting a CCR3 receptor with an effective inhibitory amount of the compound.

In another embodiment, the present invention provides a method for treating or preventing inflammatory disorders comprising administering to a patient in need thereof a therapeutically effective amount of a compound of the present invention, or a pharmaceutically acceptable salt thereof.

In another embodiment, the present invention provides a method for treating or preventing disorders selected from asthma, allergic rhinitis, atopic dermatitis, inflammatory bowel diseases, idiopathic pulmonary fibrosis, bullous pemphigoid, helminthic parasitic infections, allergic colitiLs, eczema, conjunctivitis, transplantation, familial eosinophilia, eosinophilic cellulitis, eosinophilic pneumaonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

In another embodiment, the present invention provides a method for treating or preventing disorders selected from asthma, allergic rhinitis, atopic dermatitis, and inflammatory bowel diseases.

In another embodiment, the present invention provides a method for treating or preventing asthma.

In another embodiment, the present invention provides a method for treating or preventing allergic rhinitis.

In another embodiment, the present invention provides a method for treating or preventing atopic dermatitis.

In another embodiment, the present invention provides a method for treating or preventing inflammatory bowel disease.

In another embodiment, the present invention provides novel compounds of formula (I) for use in therapy.

In another embodiment- the present invention provides the use of novel compounds of formula (I) for the manufacture of a medicament for the treatment of allergic disorders.

In another embodiment, $R^1$ and $R^2$ are independently selected from H, and $C_{1-8}$ alkyl.

In another embodiment, $R^1$ and $R^2$ are H.

In another embodiment, $R^4$ is absent, taken with the nitrogen to which it is attached to form an N-oxide, or selected from $C_{1-8}$ alkyl, $(CH_2)_rC_{3-6}$ cycloalkyl, and a $(CH_2)_r$—$C_{3-6}$ carbocyclic residue substituted with 0–3 $R^{4c}$;

and $R^{4c}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rNR^{4a}R^{4a}$, and $(CH_2)_r$phenyl.

In another embodiment, $R^4$ is absent.

In another embodiment, Z is selected from O and S.

In another embodiment, $R^3$ is selected from a $(CR^3{}'H)_r$—$C_{3-8}$ carbocyclic residue substituted with 0–5 $R^{15}$, wherein the carbocyclic residue is selected from phenyl, naphthyl, and adamantyl; and a $(CR^3{}'H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, indazolyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, $R^3$ is selected from a $(CH_2)_r$—$C_{3-8}$ carbocyclic residue substituted with 0–5 $R^{15}$, wherein the carbocyclic residue is selected from phenyl; and a $(CH_2)_r$-heterocyclic system substituted with 0–3 $R^{15}$, wherein the heterocyclic system is selected from thiazolyl and indazolyl.

In another embodiment, $R^5$ is

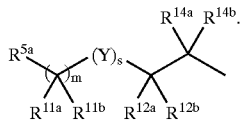

In another embodiment, $R^5$ is

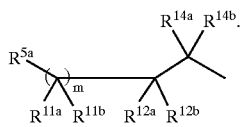

In another embodiment, $R^{5a}$ is selected from phenyl substituted with 0–5 $R^{16}$; and a heterocyclic residue substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, $R^{5a}$ is phenyl substituted with 0–3 $R^{16}$.

In another embodiment, $R^{5a}$ is phenyl substituted with 0–2 $R^{16}$.

In another embodiment, $R^8$ is selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_rC(O)OH$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_rOC(O)R^{19}$, $(CH_2)_rS(O)R^{19}$, $(CH_2)_rS(O)_2R^{19}$, $(CH_2)_rS(O)_2N(R^{18a})R^{18b}$, $(CH_2)_rN(R^{18C})S(O)_2R^{19}$, a $(C(R^{8a})(R^{8b}))_r$—$C_{3-10}$ carbocyclic residue substituted with 0–5 $R^{17}$, and a $(C(R^{8a})(R^{8b}))_r$-5–10 membered heterocyclic system containing 1–4 heteroatoms selected from N, O and S, substituted with 0–3 $R^{17}$ wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; $R^{8a}$ and $R^{8b}$, at each occurrence, are independently selected from H, methyl, ethyl, propyl, i-propyl, butyl, cyclopropyl, cyclopentyl, cyclohexyl, and $(CH_2)_r$phenyl substituted with 0–3 $R^{18}$.

In another embodiment, $R^8$ is selected from H, methyl, ethyl, propyl, i-propyl, butyl, pentyl, hexyl, $C_{2-8}$ alkenyl, $C_{2-8}$ alkynyl, $(CH_2)_r$cyclopropyl, $(CH_2)_r$-cyclopropyl, $(CH_2)_r$-cyclopentyl, $(CH_2)_r$-cyclohexyl, $(CF_2)_rCF_3$, $(CH_2)_rN(R^{18a})R^{18b}$, $(CH_2)_rOH$, $(CH_2)_rOR^{19}$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_rOC(O)R^{19}$, a $(C(R^{8a})(R^{8b}))_r$—$C_{3-10}$ carbocyclic residue substituted with 0–5 $R^{17}$, wherein the carbocyclic residue is selected from cyclohexyl and phenyl, and a $(C(R^{8a})(R^{8b}))_r$-5–10 membered heterocyclic system containing 1–4 heteroatoms selected from N, O, and S, substituted with 0–3 $R^{17}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; $R^{8a}$ and $R^{8b}$, at each occurrence, are independently selected from H, methyl, ethyl, propyl, i-propyl, butyl, cyclopropyl, cyclopentyl, cyclohexyl, and $(CH_2)_r$phenyl substituted with 0–3 $R^{18}$.

In another embodiment, $R^8$ is selected from H, $C_{1-6}$ alkyl, $(CH_2)_rC_{3-6}$ cycloalkyl, $(CH_2)_rN(R^{18a})R^{18b}$, $(CH_2)_rN(R^{18c})C(O)R^{19}$, a $(C(R^{8a})(R^{8b}))_r$—$C_3$-$^{10}$ carbocyclic residue substituted with 0–5 $R^{17}$, wherein the carbocyclic residue is selected from cyclohexyl and phenyl, and a $(C(R^{8a})(R^{8b}))_r$-5–10 membered heterocyclic system containing 1–4 heteroatoms selected from N, O, and S, substituted with 0–3 $R^{17}$, wherein the heterocyclic system is selected from pyridinyl; $R^{8a}$ and $R^{8b}$, at each occurrence, are independently selected from H, methyl, ethyl, propyl, i-propyl, butyl, cyclopropyl, cyclopentyl, cyclohexyl, and $(CH_2)_r$phenyl substituted with 0–3 $R^{18}$.

In another embodiment, $R^8$ is selected from H, methyl, ethyl, propyl, i-propyl, butyl, pentyl, hexyl, $(CH_2)_rN(R^{18a})R^{18b}$, $(CH_2)_rN(R^{18c})C(O)R^{19}$, a $(C(R^{8a})(R^{8b}))_r$—$C_{3-10}$ carbocyclic residue substituted with 0–5 $R^{17}$ wherein the carbocyclic residue is phenyl, and a $(C(R^{8a})(R^{8b}))_r$-5–10 membered heterocyclic system containing 1–4 heteroatoms selected from N, O, and S, substituted with 0–3 $R^{17}$, wherein the heterocyclic system is selected from pyridinyl.

In another embodiment, $R^9$ is selected from H, methyl, ethyl, propyl, i-propyl, butyl, i-butyl, t-butyl, pentyl, $C_{2-8}$ alkenyl, $C_{2-8}$ alkynyl, $(CH_2)_r$-cyclopropyl, $(CH_2)_r$-cyclopentyl, $(CH_2)_r$-cyclohexyl, $(CF_2)_rCF_3$, $(CH_2)_qN(R^{18a})R^{18b}$, $(CH_2)_qOH$, $(CH_2)_qOR^{19}$, $(CH_2)_qC(O)R^{19}$, $(CH_2)_qC(O)N(R^{18a})R^{18b}$, $(CH_2)_qN(R^{18c})C(O)R^{19}$, $(CH_2)_qC(O)OR^{19}$, $(CH_2)_qOC(O)R^{19}$, a $(C(R^{8a})(R^{8b}))_r$—$C_3$(carbocyclic residue substituted with 0–5 $R^{17}$, and a $(C(R^{8a})(R^{8b}))_r$-5–10 membered heterocyclic system containing 1–4 heteroatoms selected from N, O, and S, substituted with 0–3 $R^{17}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3- triazolyl, tetrazolyl, thiadiazolyl, thiazolyl, oxazolyl, pyrazinyl, and pyrimidinyl.

In another embodiment, $R^9$ is selected from H, methyl, ethyl, propyl, i-propyl, butyl, i-butyl, t-butyl, pentyl, $C_{2-8}$ alkenyl, $C_{2-8}$ alkynyl, $(CH_2)_r$-cyclopropyl, $(CH_2)_r$-cyclopentyl, $(CH_2)_r$-cyclohexyl, $(CF_2)_rCF_3$, $(CH_2)_qN(R^{18a})R^{18b}$, $(CH_2)_qOH$, $(CH_2)_qOR^{19}$, $(CH_2)_qC(O)R^{19}$, $(CH_2)_qC(O)N(R^{18a})R^{18b}$, $(CH_2)_qN(R^{18c})C(O)R^{19}$, $(CH_2)_qC(O)OR^{19}$, $(CH_2)_qOC(O)R^{19}$, a $(C(R^{8a})(R^{8b}))_r$—$C_{3-10}$ carbocyclic residue substituted with 0–5 $R^{17}$, and a $(C(R^{8a})(R^{8b}))_r$-5–10 membered heterocyclic system containing 1–4 heteroatoms selected from N, O, and S, substituted with 0–3 $R^{17}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, $R^9$ is selected from H, methyl, ethyl, propyl, i-propyl, butyl, pentyl, hexyl, $(CH_2)_rN(R^{18a})R^{18b}$, $(CH_2)_rN(R^{18c})C(O)R^{19}$, a $(C(R^{8a})(R^{8b}))_r$—$C_{3-10}$ carbocyclic residue substituted with 0–5 $R^{17}$ wherein the carbocyclic residue is phenyl, and a $(C(R^{8a})(R^{8b}))_r$-5–10 membered heterocyclic system containing 1–4 heteroatoms selected from N, O, and S, substituted with 0–3 $R^{17}$, wherein the heterocyclic system is selected from pyridinyl.

In another embodiment, $R^9$ is selected from H, methyl, ethyl, propyl, i-propyl, butyl, i-butyl, t-butyl, pentyl, $N(R^{18a})R^{18b}$, a $C_{3-10}$ carbocyclic residue substituted with 0–1 $R^{17}$, wherein the carbocyclic residue is phenyl, and a 5–10 membered heterocyclic system containing 1–4 heteroatoms selected from N, O, and S, substituted with 0–1 $R^{17}$, wherein the heterocyclic system is pyridinyl.

In anther embodiment, $R^{11a}$ and $R^{12a}$, at each occurrence are
  independently selected from H, methyl, ethyl, propyl, i-propyl, butyl, $(CF_2)_rCF_3$, $N(R^{18a})R^{18b}$, $(CH_2)_rOH$, $(CH_2)_rOR^{19}$, $(CH_2)_rN(R^{18c})C(O)R^{19}$; and
$R^{11b}$, $R^{12b}$, $R^{14a}$ and $R^{14b}$ at each occurrence are independently selected from H, methyl, ethyl, propyl, i-propyl, butyl, $(CF_2)_rCF_3$, $N(R^{18a})R^{18b}$, $(CH_2)_rOH$, $(CH_2)_rOR^{19}$, $(CH_2)_rN(R^{18c})C(O)R^{19}$;
  alternatively, $R^{11a}$ and $R^{11b}$ taken together are seleted form $=O$, or $=NOH$, or $R^{12a}$ and $R^{12b}$ taken together are seleted form $=O$, or $=NOH$.

In another embodiment, $R^{16}$, at each occurrence, is independently selected from $C_{1-8}$ alkyl, $(CH_2)_rC_{3-6}$ cycloalkyl, $CF_3$, Cl, Br, I, F, $NR^{16a}R^{16a}$, $NO_2$, CN, OH, $OR^{16d}$, $C(O)R^{16b}$, $C(O)NR^{16a}R^{16a}$, and $NR^{16f}C(O)R^{16b}$; $R^{16a}$, at each occurrence, is independently selected from H, methyl, ethyl, propyl, i-propyl, butyl, cyclopropyl, cyclopentyl, cyclohexyl, and $(CH_2)_r$phenyl substituted with 0–3 $R^{16e}$; and $R^{16b}$, at each occurrence, is independently selected from methyl, ethyl, propyl, i-propyl, butyl, cyclopropyl, cyclopentyl, cyclohexyl, and $(CH_2)_r$phenyl substituted with 0–3 $R^{16e}$; and $R^{16d}$, at each occurrence, is independently selected from methyl, ethyl, propyl, i-propyl, butyl, and phenyl; and $R^{16e}$, at each occurrence, is independently selected from methyl, ethyl, propyl, i-propyl, butyl, Cl, F, Br, I, CN, $NO_2$, $(CF_2)_rCF_3$, OH, and $(CH_2)_rOC_{1-5}$ alkyl; and $R^{16f}$, at each occurrence, is independently selected from H, methyl, ethyl, propyl, i-propyl, and butyl.

In another embodiment, the compound of formula (I) is

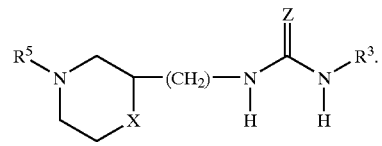

It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom or ring is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0–2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups "Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, the term "5-6-membered cyclic ketal" or "acetal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5- to 7- membered monocyclic or bicyclic or 7- to 10-membered bicyclic heterocyclic aromatic ring which consists of carbon atoms and from 1 to 4 heterotams independently selected from the group consisting of N, O and S.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, xanthenyl. Heterocycles include, but are not limited to, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

The compounds herein described may have asymmetric centers. While all enantiomers/diasteriomers are intended to be covered by the instant application, ne enantiomer of a compound of Formula (I) may display superior biological activity over the opposite enantiomer. When required, separation of the racemic material can be achieved by methods known in the art. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. Only stable compounds are envisioned for this invention.

"Therapeutically effective amount" is intended to include an amount of a compound of the present invention alone or an amount of the combination of compounds claimed or an amount of a compound of the present invention in combination with other active ingredients effective to treat the inflammatory diseases described herein.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is T. W. Greene and P. G. M. Wuts, *Protective Groups In Organic Synthesis*, Wiley and Sons, 1999. Some protecting groups are also discussed in M. Bodanszky and A. Bodanszky, *The Practice of Peptide Synthesis*, 2nd ed., Springer-Verlag, 1994; and M. Bodanszky, *Peptide Chemistry*, 2nd ed., Springer-Verlag, 1993.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula I into another compound of formula I. Examples of such manipulations are conversion of an ester or a ketone to an alcohol; conversion of an ester to a ketone; interconversions of esters, acids, and amides; alkylation, acylation, and sulfonylation of alcohols and amines; and many others. Substituents can also be added using common reactions such as alkylation, acylation, halogenation, or oxidation. Such manipulations are well known in the art, and many reference works summarize procedures and methods for such manipulations. Some reference works which gives examples and references to the primary literature of organic synthesis for many functional group manipulations as well as other transformations commonly used in the art of organic synthesis are R. C. Larock, *Comprehensive Organic Transformations*, VCH, 1989; A. Katritzky et al. (series editors), *Comprehensive Organic Functional Group Transformations*, Pergamon, 1995; and B. Trost and I. Fleming (series editors), *Comprehensive Organic Synthesis*, Pergamon, 1991.

Generally, compounds described in the scope of this patent application can be synthesized by the routes described in Schemes 1, 2, or 3. In all schemes, P and P' are suitable protecting groups such as those described in T. W. Greene and P. G. M. Wuts, *Protective Groups In Organic Synthesis*, John Wiley and Sons, 1999; M. Bodanszky and A. Bodanszky, *The Practice of Peptide Synthesis*, 2nd ed., Springer-Verlag, 1994; or M. Bodanszky, *Peptide Chemistry*, 2nd ed., Springer-Verlag, 1993.

In the attached schemes, $R^6$ may be either $R^6$ or $R^{10}$ as defined in the claims depending on the location of the substituent.

In Scheme 1, an appropriately substituted protected aminomethylpiperidine 1 can be alkylated by reaction with an appropriate alkyl halide (X=Cl, Br, I) or activated alkyl alcohol (for example, X=methanesulfonate, p-toluenesulfonate, trifluoromethanesulfonate, or other leaving group capable of reacting with a nucleophilic amine) 2 to provide the protected aminomethylpiperidine 3. The alkylation reaction can be performed with or without the addition of an acid scavenger or base such as carbonate and bicarbonate salts, triethylamine, 1,8-diazabicyclo[5.4.0]undec-7-ene (DBU), diisopropylethylamine (Hünig's base), 4-(N,N-dimethylamino)pyridine (DMAP), and the like. If the alkylating agent 2 is not an alkyl iodide, then potassium iodide can be added to facilitate the alkylation reaction if the solvent and reactant are compatible with such an additive. The reaction can be performed in a suitable solvent such as an alcohol, acetonitrile, acetone, 2-butanone, N,N- dimethylformamide (DMF), N,N-dimethylacetamide, N-methylpyrrolidinone, or dimethyl sulfoxide (DMSO), among others, and can be performed at a temperature in the range of room temperature to the reflux temperature of the solvent. The amine protecting group P can subsequently be removed to provide the amine 4. Protecting groups include phthalimide which can be removed by treatment with hydrazine; tert-butyloxycarbonyl (Boc) or bis-Boc which can be removed by treatment with an appropriate acid such as trifluoroacetic acid or hydrochloric acid in a suitable solvent; benzyloxycarbonyl (carbobenzyloxy or Cbz) which can be removed by a variety of catalytic reduction methods familiar to one skilled in the art; benzyl, diphenylmethyl or triphenylmethyl (trityl) or substituted variants of these groups which can also be removed by reduction methods; 2,4-dimethylpyrrole (S. P. Breukelman et al., J. Chem. Soc. Perkin Trans. I, 1984, 2801); N-1,1,4,4-tetramethyldisilylazacyclopentane (STABASE) (S. Djuric, J. Venit and P. Magnus, Tetrahedron Lett. 1981, 22, 1787); and other protecting groups.

Reaction of the amine 4 with an isocyanate or isothiocyanate 5 (Z=O or S) or with a carbamoyl chloride 6 (X'=Cl), phenyl carbamate 6 (X'=phenoxy) or 2- or 4-nitrophenyl carbamate 6 (X'=2- or 4-nitrophenoxy), or their thiocarbonyl equivalents, yields urea or thiourea 7. Reaction of 4 with a chloroformate or chlorothioformate 8 (Z=O or S) such as 2- or 4-nitrophenyl chloroformate or phenyl chloroformate (X''=2- or 4-nitro or H) or their thiocarbonyl equivalents, followed by treatment of the intermediate 9 with an amine 10, also yields the corresponding urea or thiourea 7. Likewise, reaction of carbamate 9 (X''=H, or 2- or 4-nitro) with disubstituted amine 11 yields trisubstiuted urea or thiourea 12. Reaction of the amine 4 with an N,N-disubstituted carbamoyl chloride 13 (X'=Cl), phenyl carbamate 13 (X'=phenoxy) or 2- or 4-nitrophenyl carbamate 13 (X'=2- or 4-nitrophenoxy), or their thiocarbonyl equivalents, also provides the corresponding N,N-disubstituted urea or thiourea 12.

Amine 4 can also be reductively alkylated with an aldehyde 14 to yield 15 by conditions familiar to one skilled in the art such as those reported in A. F. Abdel-Magid et al., Tetrahedron Lett. 1990, 31, 5595. This secondary amine can subsequently be reacted as described for reactions of 4 with isocyanates or isothiocyanates or carbamoyl chlorides or carbamates to provide trisubstituted ureas 16 or with carbamoyl chlorides or carbamates to yield tetrasubstituted ureas 17.

Amine 4 can also be converted into an isocyanate, isothiocyanate, carbamoyl chloride or thiocarbamoyl chloride (these reactions are not shown in Scheme 1). Examples of methods for such conversions can be found in J. Nowakowski, J. Prakt. Chem. 196, 338, 667; H.-J. Knoelker et al., Angew. Chem. 1995, 107, 2746; J. S. Nowick et al., J. Org. Chem. 1996, 61, 3929; H. A. Staab and W. Benz, Angew. Chem. 1961, 73 (for isocyanates); L. Strekowski et al., J. Heterocyclic Chem. 1996, 33, 1685; P. Kutschy et al., Synlett 1997, 289 (for isothiocyanates); F. Hintze and D. Hoppe, Synthesis 1992, 1216 (for carbamoyl chlorides); and W. Ried, H. Hillenbrand and G. Oertel, Justus Liebigs Ann. Chem. 1954, 590 (for thiocarbamoyl chlorides). These isocyanates, isothiocyanates, carbamoyl chlorides or thiocarbamoyl chlorides can then be reacted with $R^2R^3NH$ to provide di- or trisubstituted ureas or thioureas 13. An additional urea forming reaction involves the reaction of carbonyldiimidazole (CDI; J. L. Romine et al., Synthesis 1994, 846) with 4, followed by reaction of the intermediate imidazolide with 10 or in the reversed sequence (reaction of 10 with CDI, followed by treatment of the intermediate with 4). Activation of imidazolide intermediates facilitates urea formation (R. A. Bailey et al., Tetrahedron Lett. 1998, 39, 6267). One can also use 15 and 11 with CDI.

The reactions leading to formation of the ureas or thioureas can be done in aprotic inert solvents such as tetrahydrofuran, toluene, N,N-dimethylformamide, and the like, at a temperature in the range of room temperature to the reflux temperature of the solvent, and can employ the use of an acid scavenger or base such as carbonate and bicarbonate salts, triethylamine, DBU, diisopropylethylamine, 4-(N,N-dimethylamino)pyridine, and the like.

Scheme 1

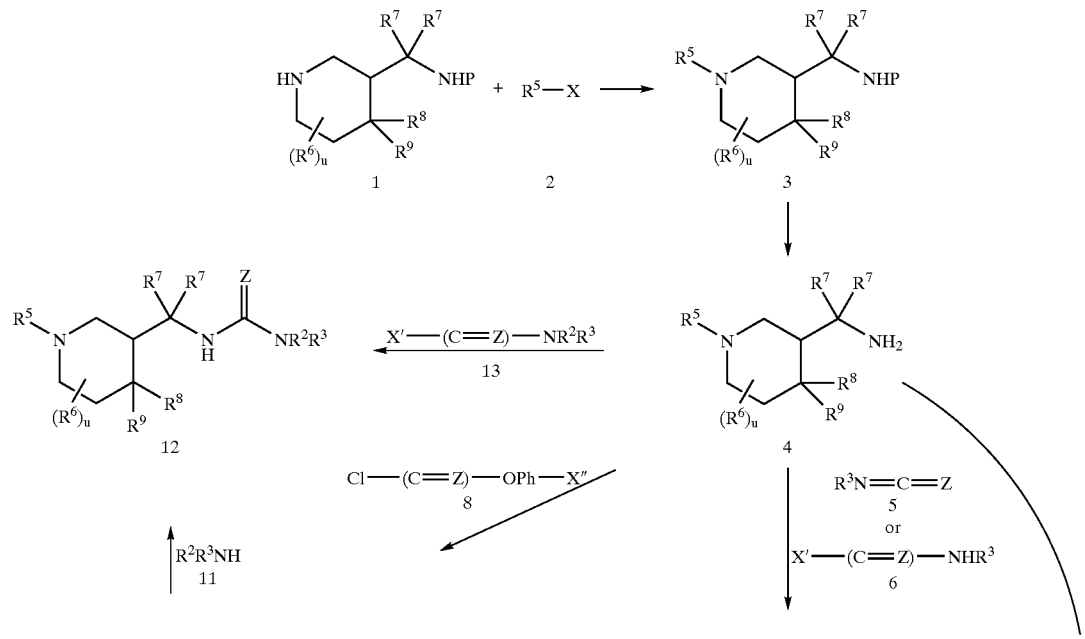

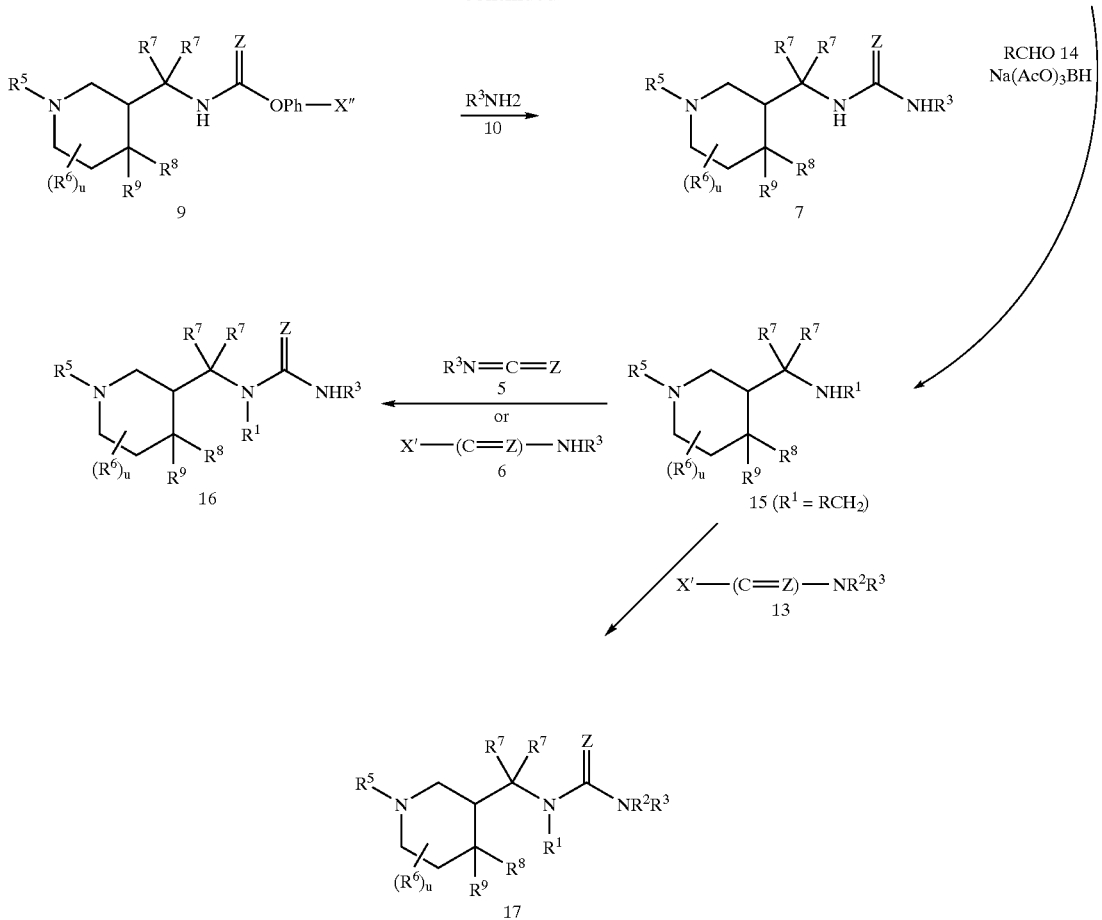

Scheme 2 describes alternative methods for attachment of certain selections of $R^5$. Reaction of amine 1 with an aldehyde 18 (R=H) or ketone 18 (R=$R^{14a}$ or $R^{13b}$ in the compounds of Formula I, or R and R' taken together form a ring as shown for certain selections of $R^5$ in the compounds of Formula I) in the presence of a reducing agent such as sodium triacetoxyborohydride, sodium cyanoborohydride, or a polymer-supported form of the cyanoborohydride anion, provides 19, where R(R')CH is certain of the selections of $R^5$ in the compounds of Formula (I); that is, the point of attachment of $R^5$ to the piperidine nitrogen must bear at least one hydrogen. Such reductive alkylation of amines is well known in the art of organic synthesis, and can be achieved using reagents, solvents and reaction conditions described in, for example, R. O. Hutchins and M. K. Hutchins in B. N. Trost and I. Fleming, *Comprehensive Organic Chemistry*, Pergamon Press: New York, 1991, vol. 8; A. F. Abdel-Magid et al., J. Org. Chem. 1996, 61, 3849; or R. O. Hutchins et al., J. Chem. Soc. Chem. Commun. 1978, 1088. The protecting group of 19 can then be removed and the urea or thiourea can be prepared from the resulting amine 20 using the procedures outlined in Scheme 1.

Scheme 2 also demonstrates another method for the preparation of amines 19 where R=H and $RR^{14a}$CH is certain of the selections of $R^5$ in the compounds of Formula (I); that is, the point of attachment of $R^5$ to the piperidine nitrogen must bear two hydrogens. This method involves the acylation of amine 1 with a carboxylic acid 21 (X=OH) or the derived carboxylic acid chloride 21 (X=Cl) or a derived mixed anhydride 21 (X=OC(=O)OR', where R' is an alkyl group) to provide the amide 22. Such amide-forming reactions can be achieved using a wide variety of reagents and conditions known to one skilled in the art, such as for example the methods described in M. Bodanszky and A. Bodanszky, *The Practice of Peptide Synthesis*, 2nd ed., Springer-Verlag: New York, 1994; and M. Bodanszky, *Peptide Chemistry*, 2nd ed., Springer-Verlag: New York, 1993. Conversion of a carboxylic acid to the derived carboxylic acid chloride or mixed anhydride (21, X=Cl or OC(=O)OR') can be achieved using a variety of conditions and reagents well known to one skilled in the art, such as for example using thionyl chloride, phosphorus pentachloride, oxalyl chloride, or an alkyl chloroformate such as isobutyl chloroformate. (See, for example, the above-cited references by Bodanszky, as well as Ansell in S. Patai, *The Chemistry of Carboxyllc Acids and Esters*, Wiley Interscience: New York, 1969, 35–68.) The amide 22 can be converted to the amine 19 (R=H) using a reducing agent such as borane or lithium aluminum hydride, a reaction well known to one skilled in the art. Such reductions can be carried out in a solvent such as a dialkyl ether or tetrahydrofuran, at a temperature in the range 0° C. to the boiling point of the solvent. The resulting amine 19 can then be deprotected to provide 20 (R=H), which can be converted to the urea or thiourea using the procedures outlined in Scheme 1.

Scheme 2

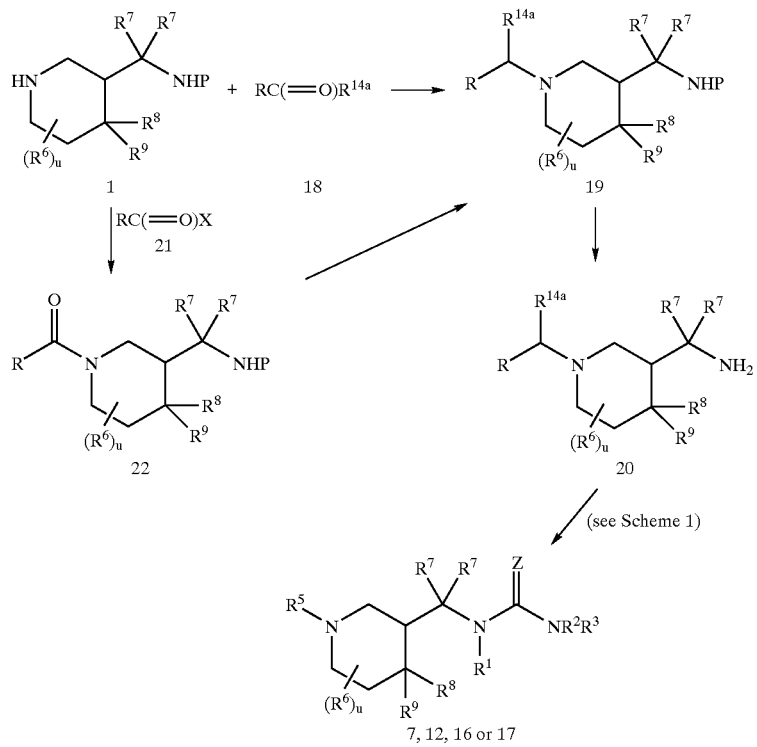

Compounds of Formula (I) can also be prepared using the sequence of reactions shown in Scheme 3. A protected piperidine 23 can be converted to the urea or thiourea 24 using one of the methods depicted in Scheme 1 for the conversion of 4 to 7, 12, 16 or 17. The protecting group can be removed, and the resulting amine 25 can be alkylated using one of the methods depicted in Schemes 1 and 2 to provide the desired compound.

guanidines 28 (as reported by H. King and I. M. Tonkin, J. Chem. Soc. 1946, 1063; and references cited therein). Alternatively, reaction of thiourea 26 with amines in the presence of triethanolamine and lac sulfur which facilitates the removal of hydrogen sulfide can provide substituted guanidines 28 (as reported by K. Ramadas, Tetrahedron Lett. 1996, 37, 5161 and references cited therein). The use of carbonimidoyldichloride 29 or 30 followed by sequential

Scheme 3

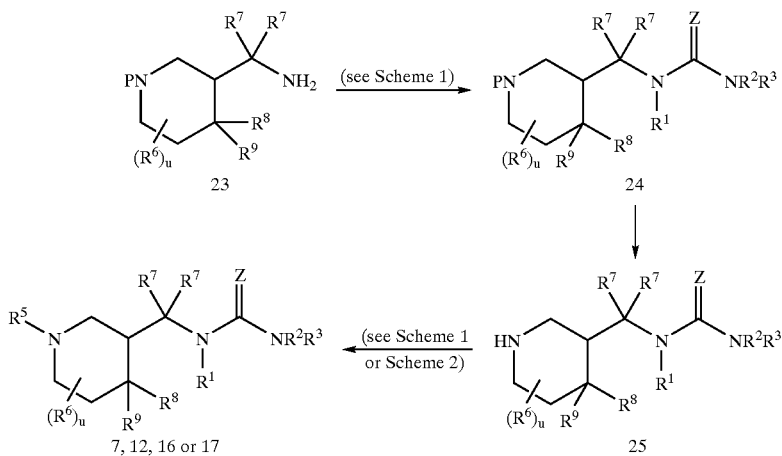

Guanidines of Formula I (Z=NR$^d$) can be synthesized by the methods outlined in Scheme 4. Compound 26 can be methylated to yield the methylisothiourea 27. Displacement of the thiomethyl group with amines can provide substituted displacements by amines provides the coresponding substituted guanidine 28 (as reported by S. Nagarajan et al., Synth. Commun. 1992, 22, 1191, and references cited therein). In a similar manner, carbonimidoyldichlorides $R^2$—N═C(Cl)$_2$ and R³—N=C(Cl)₂ (not shown in Scheme 4) can also be reacted sequentially with amines to yield di- and trisubstituted guanidine 28.

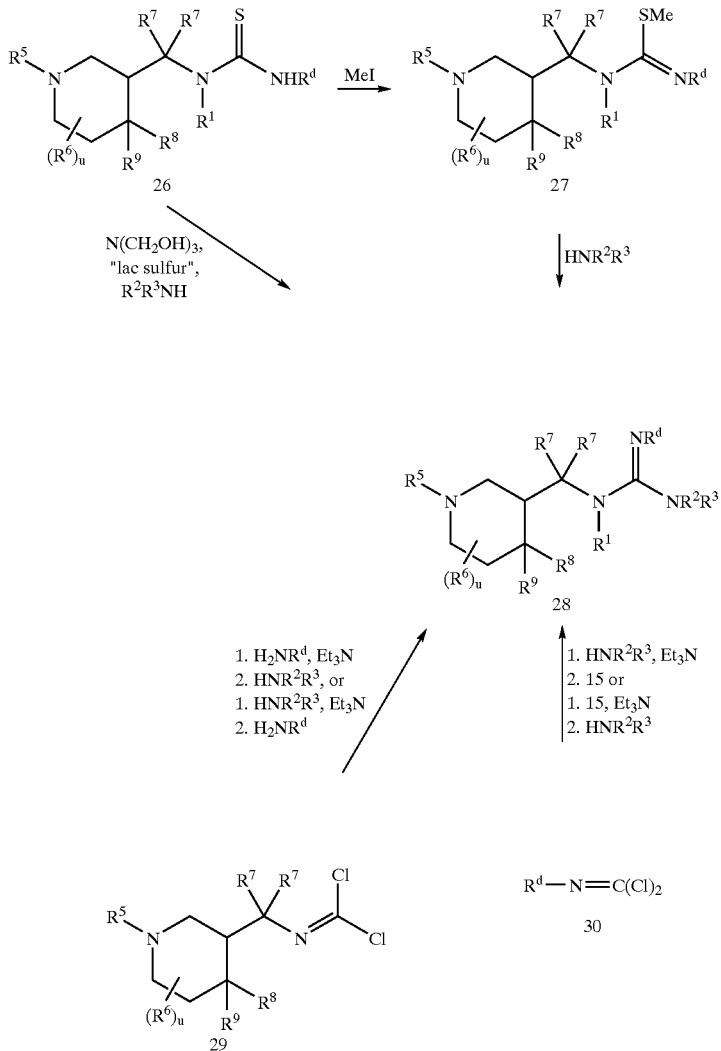

Scheme 4

Compounds of Formula I where Z=N—CN, CHNO₂, and C(CN)₂ can be synthesized by the methods shown in Scheme 5. For example, following the method reported by P. Traxler et al., J. Med. Chem. 1997, 40, 3601, amine 31 can react with malononitrile 32 in an inert solvent or neat, at a temperature in the range of room temperature to the boiling point of the solvent, or at the melting point of the solid/solid mixture, to provide the malononitrile 33. This in turn can undergo reaction with amine 15 under similar conditions to those given above to give malononitrile 34. Likewise, a similar reaction sequence can be used to prepare 37 (see, for example, J. Hoffman et al., J. Med. Chem. 1983, 26, 140) and 40 (see, for example, K. Atwal, J. Med. Chem. 1998, 41, 271).

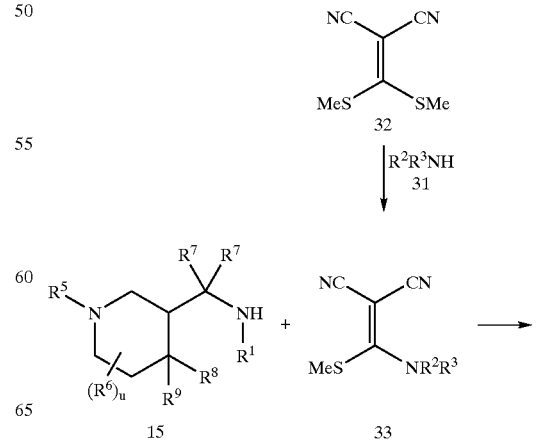

Scheme 5

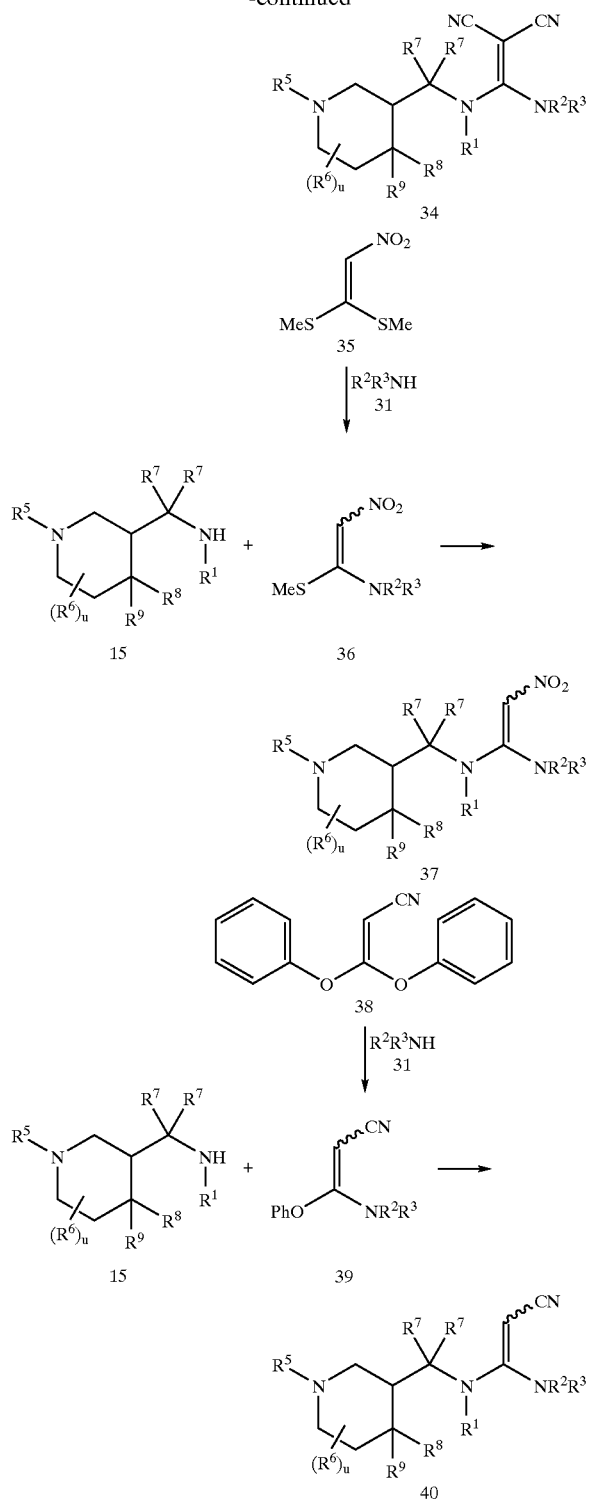

num hydride to provide amines (S. Yamazaki et al., Bull. Chem. Soc. Japan 1986, 59, 525). Ketones and trifluoromethyl ketones undergo reductive amination in the presence of titanium (IV) chloride followed by sodium cyanoborohydride to yield amines (C. Barnet et al., Tetrahedron Lett. 1990, 31, 5547). Aldehydes and ketones undergo reductive amination with sodium triacetoxyborohydride and amines to yield other amines (A. Abdel-Magid et al., J. Org. Chem. 1996, 61, 3849). Aryl amines can be synthesized from aromatic and heterocyclic hydroxyl groups (for example, phenols) using the Smiles rearrangement (J. Weidner and N. Peet, J. Heterocyclic Chem. 1997, 34, 1857). Displacement of halides, p-toluenesulfonates, methanesulfonates, trifluoromethanesulfonates, and the like with azide or cyanide followed by reduction with lithium aluminum hydride or catalytic hydrogenation or other reduction methods yields amines. Sodium diformyl amide (H. Yinglin and H. Hongwen, Synthesis 1989, 122), potassium phthalimide and bis-Boc-amine anion can all displace halides and other leaving groups, followed by standard deprotection methods to yield amines. Other methods to synthesize more elaborate amines involve the Pictet-Spengler reaction, imine/immonium ion Diels-Alder reactions (S. Larsen and P. Grieco, J. Amer. Chem. Soc. 1985, 107, 1768; P. Grieco et al., J. Org. Chem. 1988, 53, 3658; J. Cabral and P. Laszlo, Tetrahedron Lett. 1989, 30, 7237), amide reduction for example with lithium aluminum hydride or borane, organometalic addition to imines (A. Bocoum et al., J. Chem. Soc. Chem. Commun. 1993, 1542), and others which are familiar to one skilled in the art. (Additional methods for amine preparation are described further in the discussion of Scheme 9 below.)

Various aromatic amines can be synthesized using the methods shown in Scheme 6. For example, nitrobenzeneboronic acids 41 can undergo Suzuki-type coupling reactions with a wide variety of substituted iodo-, bromo-, chloro-, or trifluoromethanesulfonyloxy-substituted arenes (arene representing phenyl, naphthyl, and the like), aromatic heterocycles, alkanes, alkenes, or alkynes 42 (X=I, Br, Cl, or $CF_3SO_3$; R=optionally substituted aryl, heteroaryl, alkyl, alkenyl, or alkynyl) (see, for example, A. Suzuki, Pure Appl. Chem. 1991, 63, 419; J.-M. Fu and V. Snieckus, Tetrahedron Lett. 1990, 31, 1665; and M. Moreno-Manas et al., J. Org. Chem. 1995, 60, 2396) to provide 43. The above reactions can also undergo carbonyl insertion in the presence of an atmosphere of carbon monoxide (Ishiyama et al., Tetrahedron Lett. 1993, 34, 7595) to provide 45. Arylboronic acids 41 can also be coupled with amines 47 (R=alkyl, aryl, heteroalkyl; X'=NH), amides 47 (R=alkylcarbonyl, arylcarbonyl, and the like; X'=N-alkyl or N-aryl), sulfonamides 47 (R=alkylsulfonyl, arylsulfonyl and the like; X'=N-alkyl), phenols 47 (R=aryl, X'=O) or NH-containing heteroarenes 47 (X'=N, with R representing the remainder of a heteroarene such as pyrazole, imidazole, triazole, indazole and the like) to provide the correspondng coupled products 48 (D. Chan et al., Tetrahedron Lett. 1998, 39, 2933; P. Lam et al., Tetrahedron Lett. 1998, 39, 2941; P. Lam et al., Synlett 2000, 674).

The resulting nitro-containing compounds of Scheme 6 (43, 45 and 48) can then be reduced to the corresponding amines 44, 46 and 49 either using catalytic hydrogenation, or using a number of chemical methods well known in the art, for example with tin (II) chloride, iron or tin whit an acid, titanium (III) chloride, or ammonium sulfide. The carbonyl insertion compounds 45 and 46 can also undergo reduction of the carbonyl group to either CH(OH) or $CH_2$ linkages using methods well known in the art, for example with sodium borohydride or triethylsilane with trifluoroacetic acid.

Many amines are commercially available and can be used as 10, 11, and the amines which are precursors to isocyanates or isothiocyanates 5 or carbamoyl chlorides, phenyl carbamates or 2- or 4-nitrophenylcarbamates 6 and 13. There are numerous methods for the synthesis of non-commercially available amines familiar to one skilled in the art. For example, aldehydes and ketones can be converted to their o-benzyl oximes and then reduced with lithium alumi- Scheme 6

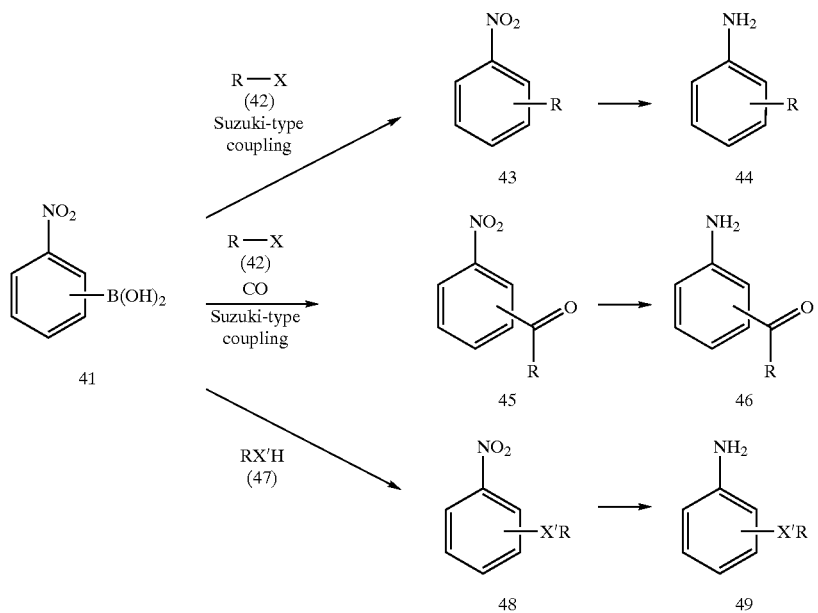

Aromatic amines can also be prepared as shown in Scheme 7. Protected aminobromobenzenes or protected aminophenyl trifluoromethanesulfonates 50, or heterocyclic analogs of 50, can undergo Suzuki-type couplings with arylboronic acids or heteroarylboronic acids 51 (R=aryl or heteroaryl). These same bromides or trifluoromethanesulfonates 50 can also undergo Stille-type couplings (A. Echavarren and J. Stille, J. Amer. Chem. Soc. 1987, 109, 5478) with aryl, alkenyl, or heteroaryl stannanes 52 (R=aryl, heteroaryl, or alkenyl). Bromides or trifluoromethanesulfonates 50 can also undergo Negishi-type couplings (E. Negishi, Accts. Chem. Res. 1982, 15, 340; M. Sletzinger et al., Tetrahedron Lett. 1985, 26, 2951) with aryl, heteroaryl, alkyl or alkenyl zinc bromides or iodides 53 (R=aryl, heteroaryl, alkyl or alkenyl; X'=Br or I). Bromides, chlorides or trifluoromethanesulfonates 50 can also undergo couplings with amines 56 (R=alkyl or aryl, X"=NH, N-alkyl, and the like), carbamates 56 (R=alkoxycarbonyl, X"=NH), alcohols 56 (R=alkyl, X"=O) or phenols 56 (R=aryl, X"=O) to provide the corresponding amines, carbamates, or ethers 57 (see, for example, J. Hartwig, Angew. Chem. 1998, 37, 2046; J. Hartwig et al., J. Org. Chem. 1999, 64, 5575; J. Wolfe et al., J. Org. Chem. 2000, 65, 1158; and J. Wolfe and S. Buchwald, J. Org. Chem. 2000, 65, 1144). The protected amines 54 or 57 resulting from these various coupling reactions can be deprotected to provide amines 55 or 58, respectively.

Scheme 7

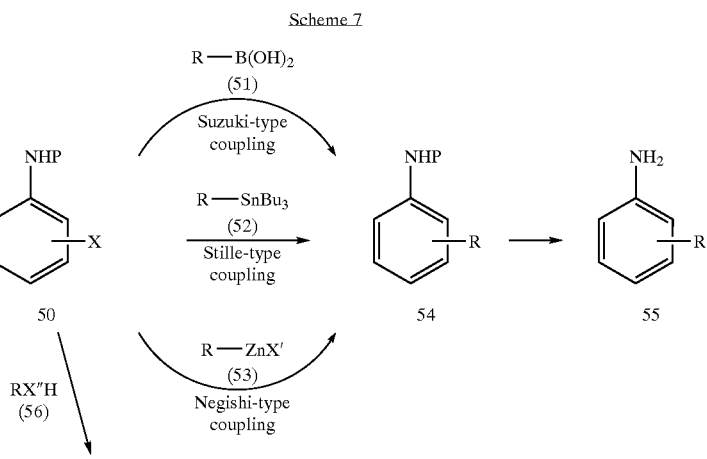

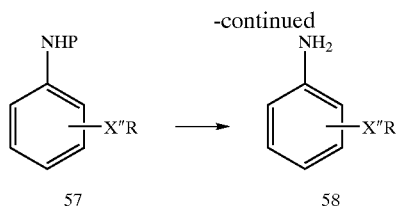

Aromatic amines bearing certain heteroaryl substituents linked through a carbon atom can also be prepared as shown in Scheme 8. Benzoic acid derivatives 59 (X'=nitro or protected amine) can be reacted with a variety of reagents to prepare a variety of five-membered ring heteroaryl-substituted compounds 60. A few examples known in the literature are described, but are not to be considered limitations on the method shown in Scheme 8. Reaction of amide 59 (X=NH$_2$) with triazidochlorosilane can provide tetrazole 60 (Y$^1$=NH, Y$^2$ and Y$^3$=N) (A. El-Ahl et al., Tetrahedron Lett. 1997, 38, 1257). Reaction of amide 59 (X=NH-alkyl) with azidotrimethylsilane can provide tetrazole 60 (Y$^1$=N-alkyl, Y$^2$ and Y$^3$=N) (J. Duncia et al., J. Org. Chem. 1991, 56, 2395). Reaction of hydrazide 59 (X=NHNH$_2$) with an acylating agent, followed by dehydration, can provide oxadiazole 60 (Y$^1$=O, Y$^2$=C-alkyl or C-aryl, Y$^3$=N); further reaction of this oxadiazole with an amine can provide triazol 60 (Y$^1$=N-alkyl, Y$^2$=C-alkyl or C-aryl, Y$^3$=N) (P. Carlsen and K. Joergensen, J. Heterocyclic Chem. 1994, 31, 805). Reaction of an acid chloride 59 (X=Cl) with an imidate ester iminophosphorane derived from azidoacetonitrile can provide imidazole 60 (Y$^1$=NH, Y$^2$ and Y$^3$=CH or C-alkyl) (P. Molina et al., Synthesis 1995, 449). Reaction of a acylated glycine 59 (X=N(alkyl)CH$_2$COOH) with a carboxylic acid anhydride, followed by treatment with a guanidine or ammonium acetate, can provide imidazole 60 (Y$^1$=NH, Y$^2$=C-alkyl or C-aryl, Y$^3$=C-alkyl, C-aryl or CH) (M. Kawase et al., Heterocycles 1995, 41, 1617). Reaction of an acid or acid chloride 59 (X=OH or Cl) with an ortho-phenylenediamine or an ortho-aminophenol can provide benzimidazole 60 (Y$^1$=NH, Y$^2$ and Y$^3$ are carbon with a benzene ring fused to the Y$^2$—Y$^3$ bond) or benzoxazole 60 (Y$^1$=O, Y$^2$ and Y$^3$ are carbon with a benzene ring fused to the Y$^2$—Y$^3$ bond) (M. DeLuca and S. Kerwin, Tetrahedron 1997, 53, 457). Reaction of an acid chloride 59 (X=Cl) with an aziridine-2-carboxylic acid ester, followed by rearrangement of the amide and oxidation, can provide oxazole 60 (Y$^1$=O, Y$^2$=CH, Y$^3$=C-COO-alkyl) (F. Eastwood et al., J. Chem. Soc. Perkin Trans. I 1997, 35). The thioamide corresponding to 59 (X=NH$_2$, with the carbonyl oxygen replaced by sulfur) can react with an alpha-bromoketone to provide thiazole 60 (Y$^1$=S, Y$^2$ and Y$^3$=CH, C-alkyl or C-aryl) (O. Uchikawa et al., Chem. Pharm. Bull. 1996, 44, 2070). Reaction of acid chloride 59 (X=Cl) with a beta-hydroxyamine, followed by treatment with phosphorus pentasulfide and oxidation, can also provide thiazole 60 (Y$^1$=S, Y$^2$ and Y$^3$ are CH, C-alkyl or C-aryl) (R. Aitken et al., J. Chem. Soc. Perkin Trans. I 1997, 935). The protected amines 60 (X'=NHP) or nitrobenzenes 60 (X'=NO$_2$) resulting from these various reactions and others like them can be deprotected or reduced, respectively, as described for Schemes 6 and 7, to provide amines 61.

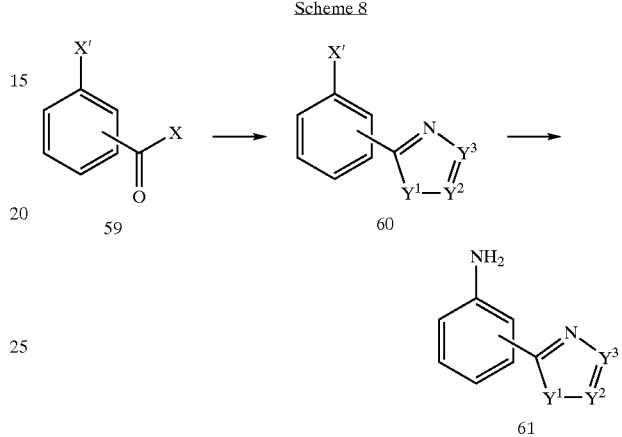

Scheme 8

The amines described above (commercially available, or prepared as described in Schemes 6, 7 and 8, and other amines) can be converted to isocyanates 5 (Z=O) using methods such as those reported by J. Nowakowski, J. Prakt. Chem. 1996, 338, 667; H.-J. Knoelker et al., Angew. Chem. 1995, 107, 2746; J. Nowick et al., J. Org. Chem. 1996, 61, 3929; and H. Staab and W. Benz, Angew. Chem. 1961, 73. They can also be converted to isothiocyanates 5 (Z=S) using methods such as those reported by L. Strekowski et al., J. Heterocyclic Chem. 1996, 33, 1685; and P. Kutschy et al., Synlett 1997, 289. They can also be converted (after optional reductive alkylation with an R$^2$ group) to carbamoyl chlorides 6 or 13 (X'=Cl, Z=O), for example as reported by F. Hintze and D. Hoppe, Synthesis 1992, 1216; to thiocarbamoyl chlorides 6 or 13 (X'=Cl, Z=S), for example as reported by W. Ried et al., Justus Liebigs Ann. Chem. 1954, 590; or to phenyl or 2- or 4-nitrophenylcarbamates 6 or 13 (X'= phenoxy, 2-nitrophenoxy or 4-nitrophenoxy; Z=O) by treatment with the corresponding phenyl, 2-nitrophenyl or 4-nitrophenyl chloroformate under suitable conditions known to one skilled in the art.

The aminomethylpiperidines and protected forms thereof (1 in Schemes 1 and 2, and 23 in Scheme 3) can be prepared using a variety of methods, as described in Schemes 9 through 12. Compounds 4 of Scheme 1 and 20 of Scheme 3 can also be prepared by the methods in Schemes 9 through 12. If the piperidine nitrogen is protected with an amine protecting group, this protecting group can be removed at any step of the reaction sequences shown and replaced by a group R$^5$ of Formula I, using one of the alkylation methods described in Schemes 1, 2, or 3 or another method, as long as the deprotection and alkylation reactions are compatible with the structure of the intermediate upon which the reactions are performed, and as long as the resulting R$^5$-substituted piperidine is compatible with the remaining reactions in the sequence. Likewise, in some of the reaction sequences shown in Schemes 9 through 12, it may be possible to substitute a group $R^5$ of Formula I for the protecting group on the piperidine nitrogen, providing direct access to 4 or 20. Such cases will be apparent to one skilled in the art.

In Scheme 9, a protected nipecotic acid 61 (R=H) or ester thereof (R=alkyl) can be reduced to the primary alcohol 62 using, for example, reagents such as lithium aluminum hydride or borane. The alcohol 62 can be converted to the amine 63 using several methods, for instance by conversion of the hydroxyl group to a leaving group such as methanesulfonate, trifluoromethanesulfonate or p-toluenesulfonate; displacement of the leaving group with an appropriate nucleophile such as azide anion; and reduction of the resulting azide to an amine using, for example, a method such as catalytic hydrogenation or reduction with triphenylphosphine followed by hydrolysis of the intermediate iminophosphorane with water. Examples of these transformations can be found in K. Hilpert et al., J. Med. Chem. 1994, 37, 3889; C. Lebarbier et al., Synthesis 1996, 1371; and M. Rubiralta et al., Synth. Commun. 1992, 22, 359. The alcohol 62 can also be converted directly to the azide with reagents such as hydrazoic acid or diphenylphosphoryl azide in the presence of a dialkyl azodicarboxylate and triphenylphosphine, for example as described in B. Lal et al., Tetrahedron Lett. 1977, 1977; or J. Hiebl et al., J. Med. Chem. 1991, 34, 1426.

An alternative method for conversion of the ester or acid 61 to the amine 63, also shown in Scheme 9, involves first conversion of the ester or acid to an amide 64 using methods well known in the art, followed by reduction of the amide to the amine 63 using any of a variety of methods well known in the art, such as reduction with lithium aluminum hydride or borane (see, for example, S. Choi et al, J. Med. Chem. 2000, 43, 205).

Amines 67 bearing a single substituent $R^7$ can be prepared as shown in Scheme 9. The ester or acid 61 can be converted to a ketone 65 using a variety of methods, for example via the N,O-dimethylhydroxamide prepared from the acid 61 (R=H) or via the derived acid chloride by treatment with an organometallic reagent such as an organomagnesium halide or an organolithium (see, for example, S. Nahm and S. Weinreb, Tetrahedron Lett. 1981, 22, 3815; R. Tillyer et al., Synlett 1996, 225; and C. Yang and N. Yasuda, Bioorganic Med. Chem. Lett. 1998, 8, 255). This ketone can be converted to an oxime or substituted oxime 66 (X'=OH or O-benzyl) or other imine derivative, followed by reduction to the amine 67 (S. Yamazaki et al., Bull. Chem. Soc. Japan 1986, 59, 525; Y. Kimura, Chem. Pharm. Bull. 1994, 42, 1442), or can be converted to an amine by reductive amination (see, for example, A. Johansson et al., Acta Chem. Scand. 1997, 51, 351; C. Szantay et al., Tetrahedron 1996, 52, 11053; and G. Hammond and R. Plevey, Org. Prep. Proc. Int. 1991, 23, 735). Alternatively, imine derivatives 66 (X'=H, benzyl, S(=O)Ar) can be treated with organometallic reagents such as diorganoaluminum halides, organocerium dichlorides, organozinc halides or organomagnesium halides to provide the amine substituted with two $R^7$ groups 68 (see, for example, F. Barbot and L. Miginiac, Synth. Commun. 1997, 27, 2601; E. Ciganek, J. Org. Chem. 1992, 57, 4521; M. Aidene et al., J. Organomet. Chem. 1997, 534, 117; and D. Hua et al., Tetrahedron Asymm. 1995, 6, 349).

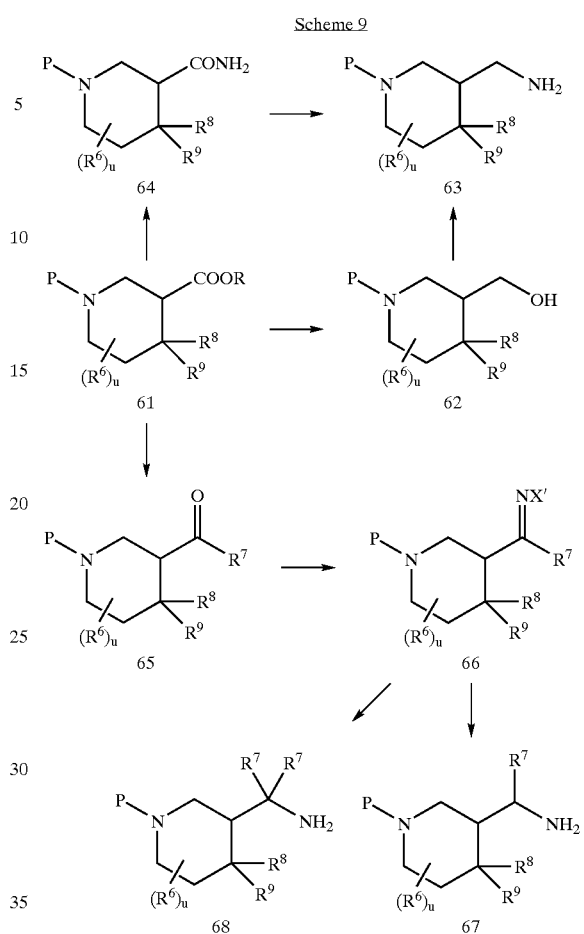

Scheme 9

An alternative route to the preparation of certain aminomethylpiperidines which can be used to prepare compounds of Formula (I) is shown in Scheme 10. An amine 69 (where $R^5$ is either the $R^5$ group of Formula (I), or a suitable protecting group such as benzyl or diphenylmethyl which can be removed and replaced with a substituent $R^5$ of Formula (I) as described in Schemes 1 or 2) can be treated with an alpha, beta-unsaturated ester 70 to provide a substituted diester 71 (where R is, for example, an alkyl group such as methyl, ethyl or benzyl). This reaction can also be performed stepwise, with two different unsaturated esters 70 (for example, one of which bears certain substituents on the olefinic carbons and the other of which bears different substituents or no substituents), or an unsaturated ester and an unsaturated nitrile (not shown in Scheme 10). The intermediate 71 can be treated with a base or other catalyst to provide, in a reaction commonly known as the Dieckmann condensation, a beta-ketoester 72. (If one ester and one nitrile are present in the intermediate, then a beta-ketonitrile will be produced, corresponding to 72 wherein the ester group is replaced by a nitrile.) These reactions are well known in the art, and are demonstrated in, for example, D. R. Howton, J. Org. Chem. 1945, 10, 277; M. N. Deshmukh et al., Syn. Commun. 1995, 25, 177; and PCT Patent Application WO 01/85728. The ketone carbonyl of 72 can be removed by methods known in the literature, for example as reported by R. M. Coates and J. E. Shaw, J. Org. Chem. 1970, 35, 2597; or by P. F. Donovan et al., J. Org. Chem. 1963, 28, 2451; to provide 73 ($R^{17}$ and $R^{18}$=H).

Alternatively, the ketone of 72 can be protected, for example as a ketal 73 ($R^{17}$ and $R^{18}$=alkoxy, or $R^{17}$ and $R^{18}$ taken together with the carbon to which they are attached make a 1,3-dioxolane or 1,3-dioxane ring), for later deprotection to restore the ketone. Examples of this protection are reported in K. C. Nicolaou and W. M. Dai, J. Am. Chem. Soc. 1992, 114, 8908; S. R. Hitchcock et al., Synthesis 1990, 1059; and J.-P. Nallet et al., Bull. Soc. Chim. Fr. 1989, 856. Other manipulations of the ketone can be performed, either at this stage or at a later stage of the synthesis, to introduce other substituents $R^{17}$ and $R^{18}$, as described below in Schemes 13 through 16. The ester of 73 can be converted to an amine as described in the discussion of Scheme 9.

Scheme 10

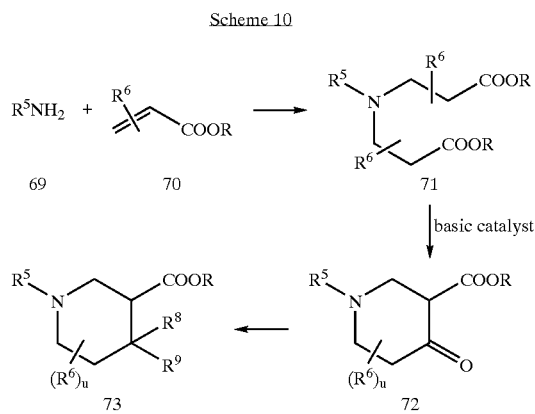

An alternative route to the preparation of certain aminomethylpiperidines which can be used to prepare compounds of Formula (I) is shown in Scheme 11. An amine 69 (where $R^5$ is either the $R^5$ group of Formula (I), or a suitable protecting group such as benzyl or diphenylmethyl which can be removed and replaced with a substituent $R^5$ of Formula (I) as described in Schemes 1 or 2) can be reacted with an unsaturated acid, acid chloride or mixed anhydride 74 (X'= OH, Cl, or OC(=O)OR, where R is an alkyl group) using conditions and reagents well known in the art as discussed with respect to Scheme 2, to provide the amide 75. This amide can be reacted with the anion derived from an activated methylene compound such as a dialkyl malonate ester 76 (X"=COOR) or an alkyl cyanoacetate 76 (X"=CN) in the presence of a suitable base and solvent to provide, after cyclization of the intermediate formed by conjugate addition, the corresponding piperidine-2,6-dione 77. Such piperidine-2,6-dione forming reactions are known in the art, and examples are described in PCT patent application WO 92/01672 (for X"=COOR) and C. Barat, J. Indian Chem. Soc. 1931, 8, 43 (for X"=CN). The anion of the activated methylene compound 76 can be prepared by treatment of 76 with a suitable base such as an alkali metal or alkaline earth alkoxide such as sodium ethoxide or potassium tert-butoxide or an alkali metal hydride such as sodium or potassium hydride or an alkali metal amide such as sodium amide, lithium diisopropylamide or potassium bis-(trimetylsilyl) amide. Suitable solvents include alcohols such as ethanol and tert-butanol; ethers such as diethyl ether, tetrahydrofuran, 1,2-dimethoxyethane (glyme), and bis(2-methoxyethyl)ether (diglyme); and hydrocarbon solvents such as benzene, toluene, and xylenes; and mixtures of these solvents. The anion of 76 can be prepared prior to solution with 75, such as treatment of 76 with sodium hydride followed by treatment with 75, or a mixture of 75 and 76 in an appropriate solvent can be treated with a base, such as treatment of such a mixture with sodium ethoxide in ethanol or with potassium tert-butoxide in tert-butanol. The reaction can be performed at a temperature in the range from room temperature to the boiling point of the solvent or solvent mixture.

Alternatively, the amine can be converted to an alpha-cyanoamide 78 (X"=CN) or a malonate half-ester half-amide 78 (X"=COOR), for example as reported by P. Benovsky and J. Stille, Tetrahedron Lett. 1997, 38, 8475; S. Hosoi et al., J. Chem. Soc. Perkin Trans I 2000, 1505; E. Awad et al., Helv. Chim. Acta 2001, 84, 1172; or A. Gazit et al., J. Med. Chem. 1991, 34, 1896. The resulting amide can be treated with an alpha, beta-unsaturated ester 79 and a base, as described above for the reaction of 75 and 76, to provide the piperidine-2,6-dione 77.

The piperidine-2,6-dione 77 can be converted to the corresponding piperidine 80 or 81 by treatment with a reducing agent appropriate to such transformations, known to one skilled in the art. Examples of such reagents are lithium aluminum hydride and borane. The reductions can be performed in a suitable solvent such as diethyl ether or tetrahydrofuran, or mixtures of such solvents with other solvents such as toluene or benzene, at a temperature in the range of about 0° C. to the boiling point of the solvent. In the case where X" is an ester, an alcohol 80 can be produced. Examples of this transformation are reported in PCT patent application WO 97/44320. This alcohol can be converted to a corresponding amine 81 as discussed in Scheme 9. In the case where X" is a nitrile, the amine 81 can be obtained directly by reduction of 77 as described.

Scheme 11

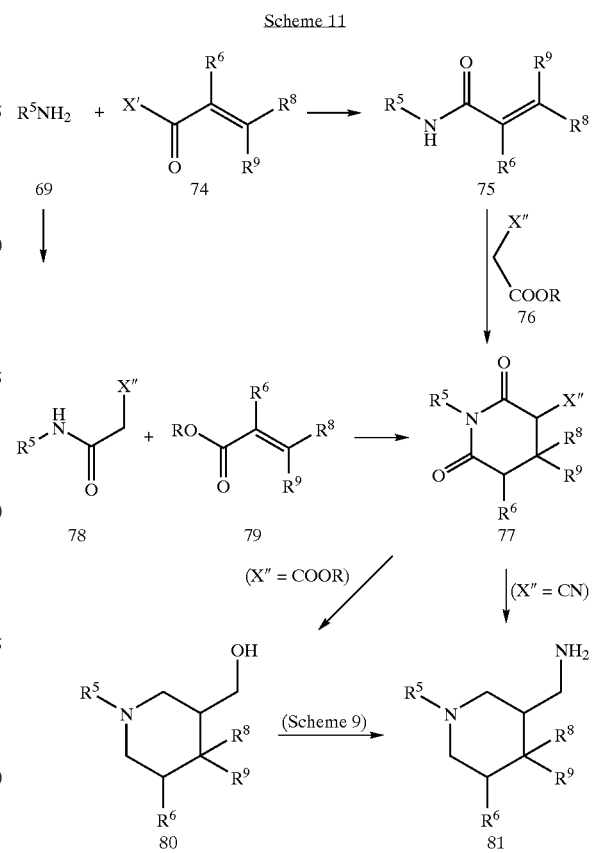

An alternative approach to nipecotic acids and esters 61, nipecotamides 64, hydroxymethylpiperidines 62, and aminomethylpiperidines 4, 15, 63, 67, 68, and similar substituted piperidines useful in the preparation of compounds of Formula (I) is shown in Scheme 12. An appropriate substituted pyridine 82 (where R can be an ester or other group which can be converted to an ester, amide, hydroxymethyl or aminomethyl using methods described in Scheme 9 or other methods) can be reduced to the piperidine 83 by treatment with hydrogen in the presence of a catalyst such as platinum, platinum oxide, palladium, palladium hydroxide, rhodium, nickel, or ruthenium, optionally in the presence of an acid such as hydrochloric acid or acetic acid, in an appropriate solvent such as methanol, ethanol, water, or a mixture of such solvents. The catalyst can optionally be supported on an inert material such as powdered carbon. The reaction can be conducted at a temperature in the range of room temperature to the boiling point of the solvent, and under a pressure of about one to 100 atmospheres of hydrogen gas. Examples of such reductions are given by M. Freifelder et al., J. Med. Chem. 1964, 7, 664; M. Freifelder et al., J. Org. Chem. 1962, 27, 284; E. et al., Tetrahedron Lett. 1996, 37, 459; F. Jurban et al., Tetrahedron Ar. 1995, 6, 321 C. Sonesson and J. Lindborg, Tetrahedron Lett. 1994, 35, 9063; and M. Uskokovic et al, J. Amer. Chem. Soc. 1978, 100, 571. Alternatively, the pyridine can first be converted to a pyridinium salt 84 by treatment with an alkylating agent R5-X, where X is halogen, p-toluenesulfonate, methanesulfonate, trifluoromethanesulfonate, or the like, followed by reduction as above, to provide the N-substituted piperidine 85. Examples of this method are given by R. Snow et al., J. Chem. Soc. Perkin Trans. I 1991, 409; M. Freifelder, J. Pharm. Sci. 1966, 55, 535; K. Kanematsu et al., J. Amer. Chem. Soc. 1968, 90, 1064; S. Dykstra et al., J. Med. Chem. 1973, 16, 1015; and L. Sternbach and S. Kaiser, J. Amer. Chem. Soc. 1952, 74, 2215. Substituted pyridines are well known in the art, and many reviews describe the preparation and reactions of pyridines, for example G. Jones in A. Boulton and A. McKillop, *Comprehensive Heterocyclic Chemistry*, Pergamon, 1984, volume 2, chapter 8.

Scheme 12

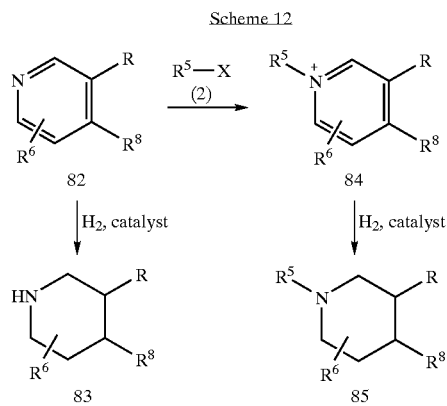

Many of the alkylating agents $R^5$—X (2), aldehydes and ketones RC(=O)R' (9) and acylating agents RC(=O)X (21) used to install the $R^5$ substituent into the compounds of Formula (I) as shown in Schemes 1, 2 and 12, and amines $R^5$—$NH_2$ (69) which can be used for this purpose as shown in Schemes 10 and 11, are commercially available or are well known in the art of organic chemistry, and methods for their preparation are well known and well exemplified. Such alkylating agents, aldehydes and ketones, acylating agents, and amines which have not been previously reported can be prepared using methods reported for the preparation of closely analogous compounds, and many other methods well known in the art. Such methods are reviewed in many well-known reference works, for example R. C. Larock, *Comprehensive Organic Transformations*, VCH, 1989; A. Katritzky et al. (series editors), *Comprehensive Organic Functional Group Transformations*, Pergamon, 1995; and B. Trost and I. Fleming (series editors), *Comprehensive Organic Synthesis*, Pergamon, 1991. Methods for producing these compounds using such known methods will be obvious to one skilled in the art.

The ketoesters 72, which can be prepared as described in Scheme 10, are versatile intermediates which can be used to prepare a variety of compounds of Formula (I) with different substituents $R^{17}$ and $R^{18}$ at the 4-position of the piperidine ring. The chemistry of such ketoesters is very widely described in the literature of organic synthesis and will be known to one skilled in the art. Some examples of methods useful for the conversion of a ketoester 72 into other piperidine derivatives suitable for the preparation of certain compounds of Formula (I) are described in Schemes 13 through 16. These examples are not meant to be exhaustive but only representative of the types of transformations that can be accomplished. Many of these methods can also be used in cases where the ester of 72 is replaced by a different group such as a hydroxymethyl or protected hydroxymethyl group or an aminomethyl or protected aminomethyl group. In these Schemes, $R^5$ can either represent the $R^5$ substituent in the compounds of Formula (I), or a nitrogen protecting group which can be removed at any desired point in the synthetic sequence and replaced with an $R^5$ substituent as found in the compounds of Formula (I) using methods described in Schemes 1 or 2.

In Scheme 13, the ketoester 72 can be allowed to react with an amine $HN(R^{17a})_2$, where the two $R^{17a}$ groups are the same or different, with removal of water, to provide the enamine 86. Although not shown in Scheme 13, such a reaction can also be performed using a monosubstituted amine $H_2NR^{17a}$ to provide the subsequent products bearing only a single substituent on the amine. Reduction of the olefinic bond using a method such as catalytic hydrogenation or reduction with a reagent such as sodium triacetoxyborohydride can provide the amine 87. A mixture of cis- and trans-isomers will sometimes result, although the cis-isomer shown will usually predominate. The corresponding trans-isomer 88 can be obtained by base-catalyzed epimerization of 87. Examples of this method can be found in PCT Patent Application WO 02/002525; L. Kudzma, Bioorg. Med. Chem. Lett. 1995, 5, 1177; R. Borne et al., J. Med. Chem. 1984, 27, 1271; J. Thomas et al., Dioorg. Med. Chem. Lett. 1999, 9, 3053; D. DeSmaele et al., J. Org. Chem. 1997, 62, 3890; and Y. Hayashi et al., J. Am. Chem. Soc. 1996, 118, 5502. The substituent or substituents $R^{17a}$ on the amine can be further manipulated at any appropriate stage of the synthetic sequence. Examples of such manipulations are removal of a benzyl substituent by hydrogenolysis and addition of a substituent by reductive alkylation, acylation, sulfonylation, and similar reactions. The ester group of 87 or 88 can be converted to an aminomethyl or substituted aminomethyl as discussed in Scheme 9.

Another method outlined in Scheme 13 involves conversion of the ketone of 72 to the enol trifluoromethanesulfonate (enol triflate) 89 using a reagent such as N-phenyltriflimide. This intermediate can be coupled with an organometallic reagent such as a boronic acid to provide the olefinic compound 90. Examples of this method can be found in D. Wustrow and L. Wise, Synthesis 1991, 993; F. Bellina et al., Tetrahedron 1999, 55, 2103; S. Jiang et al., Bioorg. Med. Chem. Lett. 1998, 8, 3689. As described above for the case of the amine substituent, the intermediate 90 can be reduced to 91, usually yielding predominantly the cis-isomer which can be isomerized to the trans-isomer 92 by treatment with base. Another possible transformation of the unsaturated ester 90 is reaction with an organocuprate reagent such as $(R^{18})_2CuLi$ or $R^{18}Cu(CN)Li$ to provide the disubstituted analog 93. The ester group of 91, 92 or 93 can be converted to an aminomethyl or substituted aminomethyl group as discussed in Scheme 9.

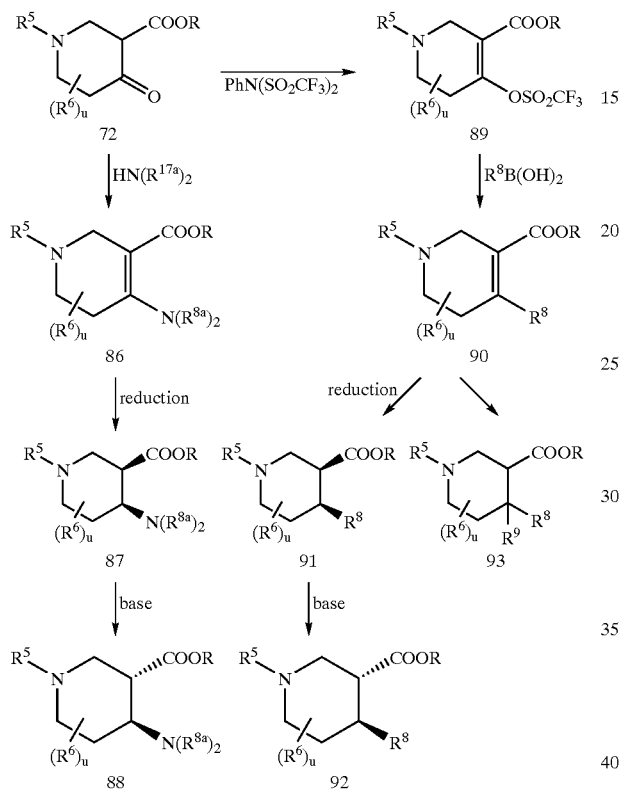

Scheme 13

Additional examples of manipulations of the ketoester 72 are illustrated in Scheme 14. The ketone of 72 can be reduced to the alcohol 94, for example by treatment with hydrogen in the presence of a catalyst such as palladium or platinum. This reduction will generally yield predominantly the cis isomer of 94, as reported by H. Jensen et al., J. Chem. Soc. Perkin Trans. I 2000, 667. (A stereospecific reduction to the 3(R), 4(S) enantiomer using yeast has been reported by D. W. Knight et al., J. Chem. Soc. Perkin Trans. I, 1998, 3673.) The alcohol of 94 can be converted to 95 bearing any of a variety of substituents $R^{17}$ using methods well known in the art, such as alkylation to provide an ether, acylation to provide an ester, or conversion to a leaving group such as chloride or a sulfonate ester, followed by displacement of the leaving group using an $R^{17}$ nucleophile such as an amine, ammonia, azide, or a carboxylic acid to provide amines, azides or esters (see, for example, U.S. Pat. No. 4,957,928 and D. W. Knight et al., op. cit.). Alternatively, a leaving group such as chloride or a sulfonate ester can undergo elimination to the olefin 96, which can undergo conjugate addition with an appropriate reagent to provide 95. Such reagents can include amines, mercaptans, organocuprates, and others known in the art to undergo such reactions. The ester group of 95 can be converted to an amine as described in Scheme 9.

The ester alcohol 94 can be further reduced using a reagent such as lithium aluminum hydride or lithium borohydride to provide the diol 97, for example as described by H. Jensen et al., op. cit., and D. W. Knight et al., op. cit. Alternatively, both the ester and ketone of 72 can be reduced in the same reaction to provide 97, for example as described by M. Sorensen et al., Synthesis 1999, 1937; or T. Ueda et al., J. Labelled Comp. Radiopharm. 2000, 43, 753. The primary alcohol can be selectively protected, for example as described by D. W. Knight et al., op. cit. The secondary alcohol of 98 can then be manipulated as described above for 94, or can be oxidized to the ketone 100 for further manipulation as described below for Schemes 15 and 16.

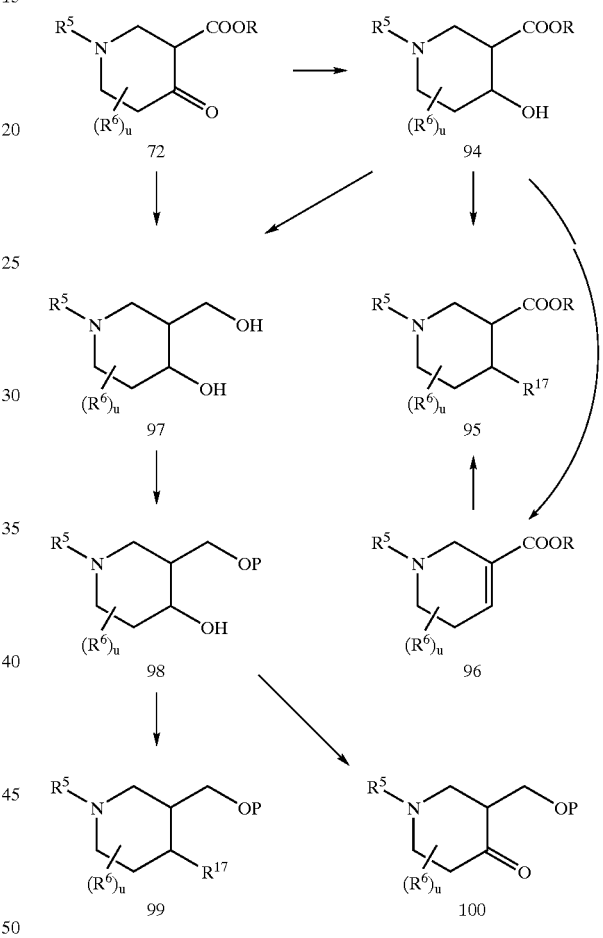

Scheme 14

The ketone of 100 can be converted to other substituents using a variety of common methods known in the art. Some examples of such transformations are shown in Scheme 15. The ketone of 100 can react with an organometallic reagent such as an organolithium or an organomagnesium halide to provide a tertiary alcohol 101 (see, for example, T. Kitazome and H. Shibano, J. Fluorine Chem. 1997, 82, 185; Z. Sui et al., Synthesis 1993, 803; C Barnett et al., J. Org. Chem. 1989, 54, 4795; and T. Govindachari et al., Tetrahedron 1970, 26, 3829). The alcohol of 101 can be further manipulated to provide 102, for example by alkylation to provide an ether (102, $R^{17}=OR^{17b}$) or acylation to provide an ester (102, $R^{17}=OC(=O)R^{17b}$).

The ketone of 100 can also react with a nucleophilic organophosphorus reagent, commonly called the Wittig reaction or a variant of the Wittig reaction, to provide an olefin 103, wherein R and R' can be a variety of substituents such as an alkyl, aryl, acyl, cyano or alkoxycarbonyl group (see, for example, A. Dutta et al., J. Med. Chem. 1996, 39, 749; M. Martinelli and B. Peterson, Tetrahedron Lett. 1990, 31, 5401; and Z. Zhou and J. Keana, J. Org. Chem. 1999, 64, 3763). Such olefins can also be prepared by reaction with another ketone RC(=O)R' in the presence of a titanium catalyst, for example as described by M. Cid et al., Tetrahedron 1988, 44, 6197. The olefin of 103 can be reduced to provide 104 ($R^{18}$=H) using, for example, catalytic hydrogenation. Alternatively, if at least one of R and R' is an electron-withdrawing group such as a ketone, ester, amide or nitrile, a substituent $R^{18}$ such as an amine, alkylthio, alkyl, alkenyl, alkynyl, aryl or cyano can be introduced by conjugate addition of an appropriate nucleophilic reagent to the olefin.

The ketone of 100 can also react with a nitrogen nucleophile such as hydroxylamine, O-alkylhydroxylamine, or alkylamine to provide 105 (R"=OH, O-alkyl, or alkyl, respectively) (see, for example, A. Diez et al., Tetrahedron 1995, 51, 5143). Such oximes and imines 105 can be reduced to the corresponding amine 106 (R"=H or alkyl; $R^{18}$=H), or an imine 105 (R"=alkyl) can be treated with organometallic reagents such as diorganoaluminum halides, organocerium dichlorides, organozinc halides or organomagnesium halides to provide the amine 106 (R"=alkyl, $R^{18}$=alkyl) (see, for example, F. Barbot and L. Miginiac, Synth. Commun. 1997, 27, 2601; E. Ciganek, J. Org. Chem. 1992, 57, 4521; M. Aidene et al., J. Organomet. Chem. 1997, 534, 117; and D. Hua et al., Tetrahedron Asymm. 1995, 6, 349). The ketone of 100 can also undergo reductive amination as described previously to provide the amine 107.

Scheme 15

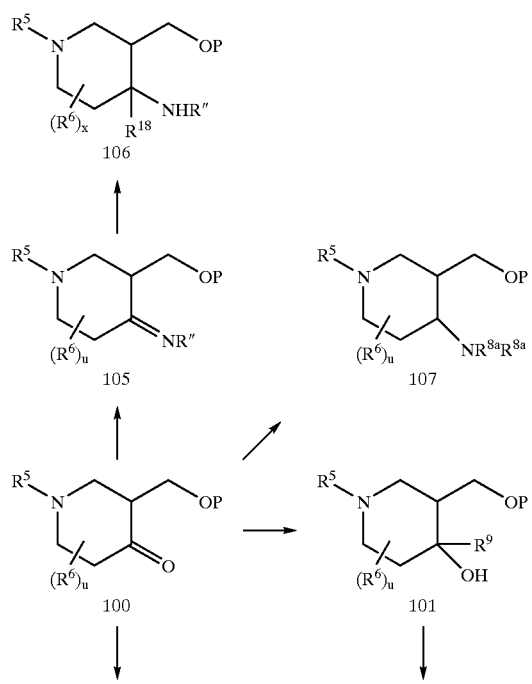

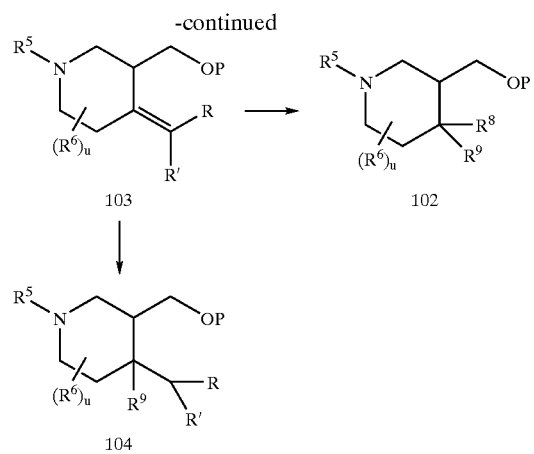

The protected alcohol group of the intermediates and in Schemes 14 and 15 can be deprotected to an amine as described in Scheme 9.

EXAMPLES

Example 1

Part A: Preparation of 3-hydroxymethylpiperidine-1-carboxylic acid tert-butyl ester A solution of piperidin-3-ylmethanol (25.0 g, 217 mmol) in 1,4-dioxane (500 mL) was stirred at room temperature and treated sequentially with triethylamine (30.3 mL, 217 mmol) and a solution of di-tert-butyl dicarbonate (47.3 g, 217 mmol) in 1,4-dioxane (60 mL). The reaction was stirred at room temperature for 18.5 hours, then was concentrated under vacuum to provide the title product as a white solid containing traces of 1,4-dioxane (47.08 g, quantitative), which was used without purification. $^1$H NMR (300 MHz, $CDCl_3$) δ3.76 (m, 2H), 3.65 (m, 2H), 3.52 (d, J=7 Hz, 2H), 2.00 (b, 1H), 1.78 (m, 2H), 1.66 (m, 1H), 1.47 (s, 9H), 1.29 (m, 1H).

Part B: Preparation of 3-methanesulfonyloxymethyl-piperidine-1-carboxylic acid tert-butyl ester A solution of 3-hydroxymethylpiperidine-1-carboxylic acid tert-butyl ester (15.0 g, 69.7 mmol) and triethylamine (14.6 mL, 104.5 mmol) in dichloromethane (270 mL) was stirred on a bath of ice and acetone. A solution of methanesulfonyl chloride (5.5 mL, 71.1 mmol) in dichloromethane (25 mL) was added dropwise at a rate which kept the internal temperature remained below 0° C. (the addition required about 20 minutes). The mixture was stirred on an ice bath for 2.5 hours, then was concentrated under vacuum. The residue was dissolved in ethyl acetate, and the mixture was filtered to remove a white crystalline solid. The filtrate was concentrated under vacuum to provide an orange gum. Purification by flash chromatography (50% ethyl acetate in hexane) provided a white solid (19.12 g, 93%). $^1$H NMR (300 MHz, $CDCl_3$) δ4.10 (m, 2H), 3.95 (bd, J=13 Hz, 1H), 3.81 (dt, J=14, 4 Hz, 1H), 3.03 (s, 3H), 2.92 (ddd, J=14, 10, 3 Hz, 1H), 2.79 (dd, J=13, 10 Hz, 1H), 1.97 (m, 1H), 1.83 (m, 1H), 1.68 (m, 1H), 1.49 (m, 1H), 1.46 (s, 9H), 1.30 (m, 1H).

Part C: Preparation of 3-azidomethylpiperidine-1-carboxylic acid tert-butyl ester A solution of 3-methanesulfonyloxymethylpiperidine-1-carboxylic acid tert-butyl ester (19.11 g, 65.1 mmol) in N,N-dimethylformamide (125 mL) was treated with sodium azide (12.70 g, 195 mmol) and the mixture was stirred at 50° C. for 22 hours. The mixture was cooled and filtered, and the filtrate was concentrated under vacuum. The residue was dissolved in ethyl acetate, washed with water, dried over sodium sulfate, and concentrated under vacuum to provide a colorless liquid (15.34 g, 98%) which was used without further purification. $^1$H NMR (300 MHz, CDCl$_3$) δ3.95 (bd, J=12 Hz, 1H), 3.86 (dt, J=13, 4 Hz, 1H), 3.22 (d, J=7 Hz, 2H), 2.87 (ddd, J=14, 11, 3 Hz, 1H), 2.68 (m, 1H), 1.9–1.6 (3H), 1.49 (m, 1H), 1.47 (s, 9H), 1.26 (m, 1H).

Part D: Preparation of 3-aminomethylpiperidine-1-carboxylic acid tert-butyl ester A mixture of 3-azidomethylpiperidine-1-carboxylic acid tert-butyl ester (5.0 g, 20.8 mmol), ethanol (125 mL) and 10% palladium on charcoal (1.5 g) was shaken under a hydrogen atmosphere (60 psig) for 5 hours. The mixture was filtered. The filtrate was concentrated to provide a colorless oil (4.27 g, 96%) which was used without further purification. $^1$H NMR (300 MHz, CDCl$_3$) δ3.91 (b, 1H), 3.82 (dt, J=13, 4 Hz, 1H), 2.90 (m, 1H), 2.8–2.5 (m, 3H), 1.85 (m, 1H), 1.75 (s, 2H), 1.66 (m, 1H), 1.6–1.4 (m, 2H), 1.47 (s, 9H), 1.20 (m, 1H). Mass spec (AP+) m/z 215.2 (M+H$^+$, 100%).

Part E: Preparation of N-methyl-3-nitrobenzamide

3-Nitrobenzoyl chloride (7.00 g, 37.7 mmol) was dissolved in tetrahydrofuran (300 mL) and methylamine (41.5 mL of a 2.0 M solution in tetrahydrofuran, 82.9 mmol) was added. The reaction mixture was stirred for 2 hours. The reaction mixture was diluted with ethyl acetate and washed three times with water. The organic layer was dried over sodium sulfate and concentrated to provide a solid (6.38 g, 94%) which was used without further purification. $^1$H NMR (300 MHz, CDCl$_3$), δ8.84 (bs, 1H), 8.67 (m, 1H), 8.37 (dd, J=8, 2 Hz, 1H), 8.28 (d, J=7 Hz, 1H), 7.78 (dd, J=8, 7 Hz, 1H), 2.83 (m, 3H). Mass spec (ES+) m$^+$/z 181 (M+H$^+$).

Part F: Preparation of 1-methyl-5-(3-nitrophenyl)-tetrazole

N-Methyl-3-nitro-benzamide (30.0 g, 167 mmol) was dissolved in acetonitrile (835 mL), sodium azide (10.9 g, 167 mmol) was added and the mixture was cooled in an ice bath. Trifluoromethanesulfonic anhydride (29 mL, 172 mmol) was added dropwise at a rate which maintained the internal temperature below 3° C. The reaction mixture was stirred for 3.5 hours at 0° C. and then was poured into 1N aqueous sodium hydroxide (100 mL). The organic layer was separated, dried over sodium sulfate and concentrated under vacuum to 50 mL. The solution was diluted with dichloromethane and water was added to precipitate a yellow solid (18.46 g, 54%). A second crop of crystals was obtained by concentrated the filtrate in vacuo and adding it to boiling ethyl acetate. Upon cooling to 0° C., additional material (6.07 g, 18%) was isolated by filtration. $^1$H NMR (300 MHz, CDCl$_3$), δ8.67 (m, 1H), 8.49 (dd, J=8, 2 Hz, 1H), 8.31 (d, J=8 Hz, 1H), 7.94 (dd, J=8, 8 Hz, 1H), 4.22 (s, 3H).

Part G: Preparation of 1-methyl-5-(3-aminophenyl)-tetrazole

1-Methyl-5-(3-nitrophenyl)-tetrazole (28.8 g, 140 mmol) was dissolved in ethyl acetate (430 mL) and methanol (1270 mL). Palladium on carbon (2.7 g, 10 wt %) was added and the mixture was shaken under a hydrogen atmosphere (60 psig) for 1.5 hours. The mixture was filtered, and the filtrate was concentrated under vacuum to give a white solid (24.0 g, 98%) which was used without further purification. $^1$H NMR (300 MHz, CDCl$_3$), δ7.21 (dd, J=8, 7 Hz, 1H), 6.99 (s, 1H), 6.90 (d, J=7 Hz, 1H), 6.76 (d, J=8 Hz, 1H), 5.44 (bs, 2H), 4.10 (s, 3H).

Part H: Preparation of [3-(1-methyl-1H-tetrazol-5-yl)-phenyl]-carbamic acid phenyl ester 1-Methyl-5-(3-aminophenyl)-tetrazole (24.0 g, 137 mmol) was dissolved in dichloromethane (1.4 L) and 2,6-lutidine (44.1 g, 411 mmol) was added. Phenyl chloroformate (21.2 g, 136 mmol) was added in 4 portions over 15 minutes, and the mixture was stirred for 1.5 hours. The mixture was poured into 1N aqueous hydrochloric acid (200 mL) and the mixture was extracted three times with dichloromethane (200 mL). The combined organic layers were washed with saturated aqueous sodium chloride, dried over sodium sulfate, and concentrated under vacuum. The crude brown material was dissolved in hot toluene, filtered, and allowed to precipitate at 0° C. to give a white solid (34.1 g). The filtrate was concentrated and recrystallized again from toluene to give an additional crop of off-white crystals (3.44 g, 93% total). $^1$H NMR (300 MHz, CDCl$_3$), δ10.51 (bs, 1H), 8.01 (s, 1H), 7.71 (dt, J=7, 2 Hz, 1H), 7.55 (m, 2H), 7.41 (m, 2H), 7.24 (m, 2H), 4.14 (s, 3H).

Part I: Preparation of 3-{3-[3-(1-methyl-1H-tetrazol-5-yl)-phenyl]-ureidomethyl}-piperidine-1-carboxylic acid tert-butyl ester A mixture of 3-aminomethylpiperidine-1-carboxylic acid tert-butyl ester (1.81 g, 8.47 mmol), [3-(1-methyl-1H-tetrazol-5-yl)-phenyl]-carbamic acid phenyl ester (2.50 g, 8.47 mmol), triethylamine (2.4 mL, 16.9 mmol) and N,N-dimethylformamide (30 mL) was stirred at room temperature for 68 hours. The mixture was concentrated under vacuum and the residue was dissolved in ethyl acetate. The solution was washed with 1.0 N aqueous sodium hydroxide, then with water, then with saturated aqueous sodium chloride, and the organic phase was dried (sodium sulfate) and concentrated under vacuum. The residue was purified by flash chromatography, eluting with 30% hexane in ethyl acetate, then with 25% hexane in ethyl acetate, to provide a white amorphous solid (3.19 g, 90%). $^1$H NMR (300 MHz, CDCl$_3$) δ7.84 (s, 1H), 7.65 (d, J=8 Hz, 1H), 7.40 (t, J=8 Hz, 1H), 7.29 (d, J=7 Hz, 1H), 4.20 (s, 3H), 3.85 (m, 1H), 3.75 (m, 1H), 3.28 (dd, J=14, 5 Hz, 1H), 3.05 (m, 2H), 2.81 (dd, J=13, 9 Hz, 1H), 1.9–1.6 (m, 3H), 1.45 (s+m, 10H), 1.27 (m, 1H). Mass spec (AP+) m/z 416.2 (M+H$^+$, 100%).

Part J: Preparation of 1-[3-(1-methyl-1H-tetrazol-5-yl)-phenyl]-3-piperidin-3-ylmethylurea hydrochloride A solution of 3-{3-[3-(1-methyl-1H-tetrazol-5-yl)-phenyl]-ureidomethyl}-piperidine-1-carboxylic acid tert-butyl ester (2.67 g, 6.43 mmol) in ethyl acetate (300 mL) was stirred on an ice bath and bubbled with hydrogen chloride gas for 20 minutes. The resulting cloudy mixture was concentrated under vacuum to provide a white powder (2.55 g, quantitative). $^1$H NMR (300 MHz, DMSO-d$_6$) δ9.28 (bs, 1H), 7.98 (t, J=2 Hz, 1H), 7.56 (dm, J=8 Hz, 1H), 7.45 (t, J=8 Hz, 1H), 7.36 (dt, J=8, 1 Hz, 1H), 6.77 (t, J=6 Hz, 1H), 4.14 (s, 3H), 3.20 (m, 2H), 3.05 (m, 2H), 2.74 (m, 1H), 2.55 (m, 1H), 1.9–1.5 (m, 4H), 1.2 (m, 1H).

Part K: Preparation of 3-(4-fluorophenyl)-2,2-dimethyl-propionic acid ethyl ester A solution of ethyl isobutyrate (11.03 g, 95 mmol) in tetrahydrofuran (75 mL) was added dropwise to a mixture of a solution of lithium bis(trimethylsilyl)amide in tetrahydrofuran (1.0 M, 100 mL, 100 mmol) and tetrahydrofuran (100 mL) at −78° C. over 15 minutes. The resulting solution was stirred at −78° C. for 45 minutes, and then treated with a solution of 1-bromomethyl-4-fluorobenzene (11.5 mL, 92 mmol) in tetrahydrofuran (25 mL) over 5 minutes. The cooling bath was removed, and the reaction mixture was stirred for 18 hours at room temperature. 1.0 N aqueous hydrochloric acid was added, and the layers were separated. The aqueous phase was extracted with ethyl acetate, and the combined organic phases were washed with 1.0 N aqueous hydrochloric acid, dried over sodium sulfate, and concentrated under vacuum to provide a brown liquid (20.7 g, quantitative) used without further purification. $^1$H NMR (300 MHz, CDCl$_3$) δ7.07 (m, 2H), 6.94 (t, J=9 Hz, 2H), 4.10 (q, J=7 Hz, 2H), 2.82 (s, 2H), 1.23 (t, J=7 Hz, 3H), 1.16 (s, 6H).

Part L: Preparation of 3-(4-fluorophenyl)-2,2-dimethyl-propionic acid

A mixture of 3-(4-fluorophenyl)-2,2-dimethyl-propionic acid ethyl ester (10.0 g, 44.6 mmol) and a solution of sodium hydroxide (25 g) in water (110 mL) was heated to reflux for 18 hours. The resulting solution was cooled to room temperature, then was stirred on ice and acidified to about pH 1 with concentrated aqueous hydrochloric acid. The resulting precipitate was collected by filtration, washed thoroughly with water, and dried under vacuum. The solid was stirred in dichloromethane, and the mixture was filtered to remove a residual gelatinous solid. The filtrate was concentrated to provide a pale yellowish solid (7.60 g, 87%) which was used without further purification. $^1$H NMR (300 MHz, CDCl$_3$) δ7.14 (m, 2H), 6.98 (t, J=8 Hz, 2H), 2.88 (s, 2H), 1.22 (s, 6H). Mass spec (ES−) m/z 195.2 (M−H$^-$, 100%).

Part M: Preparation of 1-{1-[3-(4-fluorophenyl)-2,2-dimethylpropionyl]-piperidin-3-ylmethyl}-3-[3-(1-methyl-1H-tetrazol-5-yl)-phenyl]-urea A solution of 1-[3-(1-methyl-1H-tetrazol-5-yl)-phenyl]-3-piperidin-3-ylmethylurea hydrochloride (100 mg, 284 μmol), 3-(4-fluorophenyl)-2,2-dimethylpropionic acid (56 mg, 284 μmol) and triethylamine (158 μL, 1.14 mmol) in dichloromethane (2 mL) was treated with benzotriazol-1-yloxy-tripyrrolidinophosphonium hexafluorophosphate (177 mg, 341 μmol) and the mixture was stirred at room temperature for 17 hours. The mixture was diluted with dichloromethane, washed with saturated aqueous sodium hydrogen carbonate and then with 1.0 N aqueous hydrochloric acid, dried (sodium sulfate) and concentrated under vacuum. The residue was purified by flash chromatography, eluting with 25% hexane in ethyl acetate, to provide an amorphous white solid. $^1$H NMR (300 MHz, CDCl$_3$) δ7.83 (s, 1H), 7.58 (d, J=7 Hz, 1H), 7.38 (t, J=8 Hz, 1H), 7.28 (m, 1H), 7.05 (m, 2H), 6.90 (t, J=9 Hz, 2H), 4.18 (s, 3H), 4.10 (m, 2H), 3.31 (m, 2H), 3.00 (m, 2H), 2.90 (s, 2H), 1.90 (m, 1H), 1.77 (m, 2H), 1.56 (m, 1H), 1.40 (m, 1H), 1.23 (s, 6H). Mass spec (AP+) m/z 494.2 (M+H$^+$).

Part N: Preparation of 1-{1-[3-(4-fluorophenyl)-2,2-dimethylpropyl]-piperidin-3-ylmethyl}-3-[3-(1-methyl-1H-tetrazol-5-yl)-phenyl]-urea A solution of borane in tetrahydrofuran (1.0 M, 5.3 mL, 5.3 mmol) was added to 1-{1-[3-(4-fluorophenyl)-2,2-dimethylpropionyl]-piperidin-3-ylmethyl}-3-[3-(1-methyl-1H-tetrazol-5-yl)-phenyl]-urea (66 mg, 134 μmol) and the resulting solution was stirred at room temperature for 18 hours. A mixture of 1.0 N hydrochloric acid (5 mL) and methanol (5 mL) was added very slowly until the resulting vigorous reaction subsided, then the remainder was added quickly and the resulting solution was stirred at room temperature for 5 hours. The solution was concentrated under vacuum. The residue was dissolved in 1.0 N aqueous sodium hydroxide and dichloromethane, and the phases were separated. The aqueous phase was extracted twice with dichloromethane, and the combined organic phases were dried over sodium sulfate and concentrated under vacuum. The residue was purified twice by flash chromatography, eluting with 4% methanol in dichloromethane containing 0.4% aqueous ammonium hydroxide, to provide a white amorphous solid (24 mg, 38%). $^1$H NMR (300 MHz, CDCl$_3$) δ7.81 (s, 1H), 7.68 (d, J=8 Hz, 1H), 7.34 (t, J=8 Hz, 1H), 7.18 (m, 1H), 7.01 (m, 2H), 6.84 (t, J=9 Hz, 2H), 4.09 (s, 3H), 3.09 (m, 2H), 2.95 (m, 1H), 2.55 (s, 2H), 2.40 (m, 3H), 2.10 (m, 1H), 1.9–1.5 (m, 5H), 1.0 (m, 1H), 0.85 (s, 6H). Mass spec (ES+) m/z 480.5 (M+H$^+$).

Example 2

Part A: Preparation of 3-(4-fluorophenyl)-propan-1-ol

A solution of 3-(4-fluorophenyl)-propionic acid (4.20 g, 25 mmol) in tetrahydrofuran (10 mL) was stirred on an ice bath and treated with a solution of borane in tetrahydrofuran (1.0 M, 33 mL, 33 mmol) over 15 minutes. The resulting solution was stirred at room temperature for one hour. A mixture of tetrahydrofuran (5 mL) and water (5 mL) was added over 2 minutes. After 5 minutes of additional stirring, 4 mL of additional water was added, and solid potassium carbonate was added until the aqueous phase was saturated. The layers were separated and the aqueous phase was extracted three times with ethyl acetate. The combined organic phases were dried over sodium sulfate and concentrated to provide a colorless liquid (3.70 g, 96%) which was used without further purification. $^1$H NMR (300 MHz, CDCl$_3$) δ7.16 (m, 2H), 6.99 (t, J=9 Hz, 2H), 3.69 (t, J=6 Hz, 2H), 2.70 (t, J=8 Hz, 2H), 1.87 (m, 2H), 1.50 (bs, 1H). Mass spec (CH$_4$-CI) m/z 137.0 (M+H$_+$-H$_2$O).

Part B: Preparation of 3-(4-fluorophenyl)-propionaldehyde

A solution of oxalyl chloride (1.32 mL, 15.1 mmol) in dichloromethane (40 mL) was stirred at −78° C. and treated dropwise with dimethyl sulfoxide (2.21 mL, 31.1 mL) over 5 minutes. The resulting solution was stirred for 35 minutes at −78° C. A solution of 3-(4-fluorophenyl)-propan-1-ol (1.50 g, 9.73 mmol) in dichloromethane (12 mL) was added over 5 minutes, and stirring continued at the same temperature for 50 minutes. Triethylamine (4.41 mL, 31.6 mmol) was added, and the cooling bath was replaced by an ice-water bath. The resulting slurry was stirred for one hour, then was diluted with dichloromethane. The resulting mixture was washed with half-saturated aqueous ammonium chloride, then with saturated sodium chloride, dried over sodium sulfate, and concentrated under vacuum. The resulting orange oil was distilled in a short-path apparatus at 50° C. and 0.2 Torr pressure to provide a colorless liquid (764 mg, 50%). $^1$H NMR (300 MHz, CDCl$_3$) δ9.83 (t, J=1 Hz, 1H), 7.17 (m, 2H), 6.99 (t, J=9 Hz, 2H), 2.95 (t, J=7 Hz, 2H), 2.79 (tt, J=7, 1 Hz, 2H).

Part C: Preparation of 1-{1-[3-(4-fluorophenyl)-propyl]-piperidin-3-ylmethyl}-3-[3-(1-methyl-1H-tetrazol-5-yl)-phenyl]-urea A mixture of 1-[3-(1-methyl-1H-tetrazol-5-yl)-phenyl]-3-piperidin-3-ylmethylurea hydrochloride (35 mg, 100 μmol), 3-(4-fluorophenyl)-propionaldehyde (15 mg, 100 μmol), triethylamine (15 μL, 110 μmol), resin-bound cyanoborohydride (prepared according to Ley, S. V., et al., J. Chem. Soc. Perkin Trans. 1, 1998, 2239; 100 mg), toluene (1 mL) and methanol (1 mL) was agitated gently at room temperature for 65 hours. The mixture was filtered, the resin was washed with dichloromethane, and the filtrates were concentrated. The residue was purified by flash chromatography, eluting with 4% methanol in dichloromethane containing 0.4% aqueous ammonium hydroxide, to provide an amorphous white solid (29 mg, 64%). $^1$H NMR (300 MHz, CDCl$_3$) δ7.88 (s, 1H), 7.79 (d, J=8 Hz, 1H), 7.44 (t, J=8 Hz, 1H), 7.27 (m, 1H), 7.11 (m, 2H), 6.93 (t, J=9 Hz, 2H), 4.18 (s, 3H), 3.2–3.0 (m, 4H), 2.59 (m, 4H), 2.3–1.8 (m, 8H), 1.10 (m, 1H). Mass Spec (ES+) m/z 452.4 (M+H$^+$, 100%).

Example 3

Part A: Preparation of 2-(4-trifluoromethylphenyl)-ethanol

A solution of 4-trifluoromethylphenylacetic acid (784 mg, 3.84 mmol) in tetrahydrofuran (3 mL) was cooled to 0° C. and treated dropwise with a solution of borane in tetrahydrofuran (1.0 M, 5.4 mL, 5.4 mmol). The mixture was stirred at room temperature for 2.75 hours, then was treated slowly with 50% water in tetrahydrofuran (2 mL), followed by water (2 mL). The mixture was stirred for 5 minutes, and solid potassium carbonate was added to saturate the aqueous phase. The layers were separated and the aqueous phase was extracted with ethyl acetate. The combined organic phases were dried over sodium sulfate and concentrated under vacuum to provide a colorless liquid (585 mg, 80%) which was used without further purification. $^1$H NMR (300 MHz, CDCl$_3$) δ7.59 (d, J=8 Hz, 2H), 7.38 (d, J=8 Hz, 2H), 3.92 (t, J=7 Hz, 2H), 2.95 (t, J=7 Hz, 2H), 1.53 (s, 1H).

Part B. Preparation of toluene-4-sulfonic acid 2-(4-trifluoromethylphenyl)-ethyl ester A solution of 2-(4-trifluoromethylphenyl)-ethanol (570 mg, 3.0 mmol) in pyridine (6 mL) was stirred on an ice/acetone bath and treated with p-toluenesulfonyl chloride (630 mg, 3.3 mmol). The cooling bath was replaced with an ice/water bath and the mixture was stirred for 3.5 hours. Ice-cold water (12 mL) was added slowly, and the mixture was extracted three times with chloroform. The combined organic phases were washed with water, then with cold 1.0 N aqueous sulfuric acid until the wash phase was acidic. The organic phase was dried over sodium sulfate and concentrated to provide a white solid (826 mg) which contained about 10% by weight of residual alcohol. This was used without further purification. $^1$H NMR (300 MHz, CDCl$_3$) for toluenesulfonate: δ7.65 (d, J=8 Hz, 2H), 7.50 (d, J=8 Hz, 2H), 7.26 (d, J=8 Hz, 2H), 7.23 (d, J=8 Hz, 2H), 4.26 (t, J=7 Hz, 2H), 3.02 (t, J=7 Hz, 2H), 2.44 (s, 3H).

Part C. Preparation of 1-[3-(1-methyl-1H-tetrazol-5-yl)-phenyl]-3-{1-[2-(4-trifluoromethylphenyl)-ethyl]-piperidin-3-ylmethyl}-urea A mixture of 1-[3-(1-methyl-1H-tetrazol-5-yl)-phenyl]-3-piperidin-3-ylmethylurea hydrochloride (50 mg, 142 μmol), toluene-4-sulfonic acid 2-(4-trifluoromethyl-phenyl)-ethyl ester (90% pure, 55 mg, 142 μmol), triethylamine (60 μL, 426 μmol) and acetonitrile (1.5 mL) was heated at reflux for 16.5 hours and cooled to room temperature. The mixture was concentrated, and the residue was purified by flash chromatography, eluting with 3% methanol in dichloromethane containing 0.3% aqueous ammonium hydroxide, to provide a white amorphous solid (30 mg, 45%). $^1$H NMR (300 MHz, CDCl$_3$) δ8.26 (s, !H), 7.87 (d, J=8 Hz, 1H), 7.76 (s, 1H), 7.51 (d, J=8 Hz, 1H), 7.39 (t, J=8 Hz, 1H), 7.28 (d, J=8 Hz, 2H), 7.20 (d, J=8 Hz, 1H), 6.06 (bm, 1H), 4.15 (s, 3H), 3.23 (t, J=6 Hz, 2H), 3.03 (m, 1H), 2.86 (m, 2H), 2.61 (m, 2H), 2.1–1.5 (m, 7H), 1.05 (m, 1H). Mass spec (ES+) m/z 488.5 (M+H$^+$, 100%).

Example 4

Part A: Preparation of 3-(benzyloxycarbonylaminomethyl)-piperidine-1-carboxylic acid tert-butyl ester A solution of 3-aminomethylpiperidine-1-carboxylic acid tert-butyl ester (2.20 g, 10.3 mmol) in dichloromethane (40 mL) was treated with triethylamine (1.90 mL, 13.3 mmol) and stirred on an ice bath. A solution of benzyl chloroformate (1.90 mL, 13.3 mmol) in dichloromethane (10 mL) was added over 5 minutes. The mixture was stirred at room temperature for 70 hours. It was washed with 0.1 N aqueous hydrochloric acid, dried over sodium sulfate, and concentrated under vacuum to provide a colorless gum (3.58 g, quantitative) which was used without further purification. $^1$H NMR (300 MHz, CDCl$_3$) δ7.37 (m, 5H), 5.11 (s, 2H), 3.75 (m, 2H), 3.18 (m, 1H), 3.05 (m, 2H), 2.83 (m, 1H), 1.9–1.6 (m, 4H), 1.46 (s, 9H), 1.27 (m, 1H).

Part B: Preparation of 3-(benzyloxycarbonylaminomethyl)-piperidine hydrochloride A solution of 3-(benzyloxycarbonylaminomethyl)-piperidine-1-carboxylic acid tert-butyl ester (594 mg, 1.7 mmol) in ethyl acetate (10 mL) was stirred on an ice bath and treated with a solution of hydrogen chloride in dioxane (4.0 N, 10 mL, 40 mmol). The mixture was stirred for 80 minutes, then was concentrated under vacuum. The gummy residue was triturated repeatedly in ether to provide a white powder (408 mg, 84%)which was extremely hygroscopic and was used without further purification. $^1$H NMR (300 MHz, CD$_3$OD) δ7.34 (m, 5H), 5.07 (s, 2H), 3.34 (m, 2H), 3.09 (m, 2H), 2.88 (m, 1H), 2.66 (m, 1H), 1.90 (m, 3H), 1.70 (m, 1H), 1.30 (m, 1H).

Part C: Preparation of toluene-4-sulfonic acid 2-(4-fluorophenyl)ethyl ester

A solution of 2-(4-fluorophenyl)ethanol(10.0 g, 71.3 mmol) in pyridine (100 mL) was stirred at −5° C. and treated with 4-toluenesulfonyl chloride (14.95 g, 78.4 mmol). After 3 hours, water (10 mL) was added slowly, followed by dilution with ice water and extraction with chloroform. The organic phase was washed with cold 0.5 M aqueous sulfuric acid, then with water, then with saturated aqueous sodium chloride, and was dried over sodium sulfate. Concentration under vacuum provided a pale orange oil containing residual pyridine. Further concentration under vacuum provided an oil (17.74 g) containing about 10% by weight of residual alcohol. A portion was purified by flash chromatography, eluting with 20% ethyl acetate in hexane, to provide a colorless oil. $^1$H NMR (300 MHz, CDCl$_3$) δ7.70 (d, J=8 Hz, 2H), 7.30 (d, J=8 Hz, 2H), 7.07 (m, 2H), 6.94 (t, J=9 Hz, 2H), 4.20 (t, J=7 Hz, 2H), 2.94 (t, J=7 Hz, 2H), 2.45 (s, 3H).

Part D: Preparation of {1-[2-(4-fluorophenyl)ethyl]-piperidin-3-ylmethyl}carbamic acid benzyl ester A solution of 3-(benzyloxycarbonylaminomethyl)-piperidine hydrochloride (199 mg, 690 μmol) was dissolved in aqueous sodium hydrogen carbonate and the solution was extracted with ethyl acetate. The organic phase was dried over sodium sulfate and concentrated. The residue was combined with toluene-4-sulfonic acid 2-(4-fluorophenyl) ethyl ester (97 mg, 690 μmol) and potassium carbonate (190 mg, 1.38 mmol) in acetone (15 mL) and the mixture was heated at reflux for 17 hours. The mixture was cooled, diluted with water, and extracted with ethyl acetate. The organic phase was dried over sodium sulfate and concentrated. The residue was purified by flash chromatography, eluting with ethyl acetate, to provide a white solid (140 mg, 66%). $^1$H NMR (300 MHz, CD$_3$OD) δ7.30 (m, 5H), 7.22 (m, 2H), 6.99 (t, J=9 Hz, 2H), 5.07 (s, 2H), 3.1–2.7 (m, 5H), 2.55 (m, 2H), 2.00 (m, 1H), 1.8–1.5 (m, 4H), 0.98 (m, 1H). Mass spec (ES+) m/z 371.4 (M+H$^+$, 100%).

Part E: Preparation of C-{1-[2-(4-fluorophenyl) ethyl]-piperidin-3-yl}methylamine A solution of {1-[2-(4-fluorophenyl)ethyl]-piperidin-3-ylmethyl}carbamic acid benzyl ester (140 mg, 370 μmol) was combined with Pearlman's catalyst (50 mg) and methanol (10 mL) and shaken under an atmosphere of hydrogen (40 psig) for 17 hours. The mixture was filtered, and the filtrate was concentrated to provide a gum (88 mg, quantitative) which was used without further purification. $^1$H NMR (300 MHz, CD$_3$OD) δ7.21 (m, 2H), 6.99 (t, J=9 Hz, 2H), 3.1–2.9 (m, 2H), 2.80 (m, 2H), 2.60 (m, 2H), 2.1–1.0 (m, 9H).

Part F: Preparation of (5-acetyl-4-methyl-thiazol-2-yl)-carbamic acid phenyl ester Sodium hydride (60% dispersion in mineral oil, 3.07 g, 77 mmol) was washed twice with hexane and suspended in N,N-dimethylformamide. 2-Amino-5-acetyl-4-methylthiazole (10.0 g, 64 mmol) was added with stirring and cooling on an ice bath. Stirring was continued until the sodium hydride was consumed. Diphenyl carbonate (34 g, 160 mmol) was added and the mixture was stirred for 30 minutes at room temperature. The solvent was removed under vacuum to yield a brown residue, which was dissolved in chloroform and washed successively with 0.5N aqueous hydrochloric acid, twice with water and finally with saturated aqueous sodium chloride. The aqueous phases were back extracted twice with chloroform. The combined organic fractions were dried over sodium sulfate and concentrated under vacuum to give a white solid. This was chromatographed on silica gel, eluting with 15%–70% ethyl acetate in hexane, to give a white solid (15.0 g, 85%). $^1$H NMR (300 MHz, CDCl$_3$) δ11.42 (bs, 1H), 7.47–7.40 (m, 2H), 7.33–7.27 (m, 1H), 7.22–7.18 (m, 2H), 2.72 (s, 3H), 2.50 (s, 3H). Mass spec (ES+) m/z 277.1 (M+H$^+$).

Part G: Preparation of 1-(5-acetyl-4-methylthiazol-2-yl)-3-{1-[2-(4-fluorophenyl)ethyl]-piperidin-3-ylmethyl}urea A solution of C-{1-[2-(4-fluorophenyl)ethyl]-piperidin-3-yl}methylamine (25 mg, 106 μmol), (5-Acetyl-4-methylthiazol-2-yl)-carbamic acid phenyl ester (24 mg, 106 μmol) and triethylamine (29 μL, 210 μmol) in acetonitrile (3 mL) was stirred for 18 hours and concentrated. The residue was purified by flash chromatography, eluting with 5% methanol in dichloromethane, to provide an off-white solid (30 mg, 68%). $^1$H NMR (300 MHz, CD$_3$OD) δ7.21 (m, 2H), 6.98 (t, J=9 Hz, 2H), 3.16 (m, 2H), 3.02 (m, 2H), 2.82 (m, 2H), 2.61 (m, 2H), 2.56 (s, 3H), 2.47 (s, 3H), 2.09 (m, 1H), 1.85 (m, 4H), 1.65 (m, 1H), 1.05 (m, 1H). Mass spec (ES+) m/z 419.2 (M+H$^+$, 100%).

Example 5

Part A: Preparation of trans 2-butenoic acid [2-(4-fluorophenyl)ethyl]amide

A solution of 2-(4-fluorophenyl)ethylamine (13.25 mL, 100 mmol) and triethylamine (14.6 mL, 105 mmol) in dichloromethane (375 mL) was stirred on an ice bath. A solution of crotonyl chloride (10.65 mL, 100 mmol) in dichloromethane (25 mL) was added dropwise over 15 minutes. The cooling bath was removed and the solution was stirred at room temperature for 2 hours. It was then washed twice with 1.0 N aqueous hydrochloric acid, then twice with saturated aqueous sodium hydrogen carbonate. The organic phase was dried over sodium sulfate and concentrated under vacuum to provide a yellowish solid (20.78 g, quantitative). Recrystallization from toluene provided white needles (15.5 g, 75%), mp 121–123° C. $^1$H NMR (300 MHz, CDCl$_3$) δ7.16 (m, 2H), 7.01 (t, J=9 Hz, 2H), 6.85 (dq, J=15, 7 Hz, 1H), 5.74 (dd, J=15, 1 Hz, 1H), 5.49 (bs, 1H), 3.56 (m, 2H), 2.83 (t, J=7 Hz, 2H), 1.85 (dd, J=7, 2 Hz, 3H). Mass spec (ES+) m/z 249.0 (M+H+acetonitrile$^+$, 100%).

Part B: Preparation of 1-[2-(4-fluorophenyl)ethyl]-4-methyl-2,6-dioxopiperidine-3-carboxylic acid ethyl ester Sodium (1.5 g, 65.1 mmol) was dissolved in ethanol (50 mL) and the solution was concentrated under vacuum. The residue was suspended in toluene (50 mL) and bis(2-methoxyethyl)ether (30 mL). Diethyl malonate (4.0 mL, 26.5 mmol) was added, followed by a suspension of trans-2-butenoic acid [2-(4-fluoro-phenyl)ethyl]amide (5.00 g, 24.1 mmol) in bis(2-methoxyethyl)ether (20 mL). The mixture was heated at reflux for 6 hours. The cooled mixture was washed with 1.0 N aqueous hydrochloric acid, then with water, and dried over sodium sulfate and concentrated under vacuum. The residue was purified by flash chromatography, eluting with 25% ethyl acetate in hexane, to provide a pale yellowish oil which slowly crystallized (5.81 g, 75%). This appeared to be a mixture of cis and trans isomers (approximately 15% cis). $^1$H NMR (300 MHz, CDCl$_3$) δ7.20 (m, 2H), 6.99 (t, J=9 Hz, 2H), 4.28 (m, 2H), 4.00 (m, 2H), 3.66 (d, J=5 Hz, 0.15H), 3.27 (d, J=10 Hz, 0.85H), 2.82 (m, 3H), 2.53 (m, 1H), 2.33 (dd, J=17, 10 Hz, 1H), 1.34 (m, 3H), 1.09 (d, J=7 Hz, 3H). Mass spec (AP+) m/z 322.0 (M+H$^+$, 100%).

Part C: Preparation of trans-{1-[2-(4-fluorophenyl)-ethyl]-4-methylpiperidin-3-yl}-methanol A solution of 1-[2-(4-Fluorophenyl)ethyl]-4-methyl-2,6-dioxopiperidine-3-carboxylic acid ethyl ester (2.0 g, 6.22 mmol) in tetrahydrofuran (10 mL) was added over 5 minutes to an ice-cold solution of lithium aluminum hydride (1.0 M in tetrahydrofuran, 28 mL, 28 mmol). The resulting solution was stirred at room temperature for 17 hours, then was quenched by the slow dropwise addition of water (1.06 mL), 15% aqueous sodium hydroxide (1.06 mL), and water (3.18 mL). The resulting suspension was stirred for 20 minutes, then filtered and the solid washed with ethyl acetate. The combined filtrates were concentrated under vacuum to provide an oil which slowly crystallized. This material was purified by flash chromatography, eluting with 4% methanol in dichloromethane containing 0.4% aqueous ammonium hydroxide, to provide a pale yellow solid (724 mg, 46%) as a mixture of cis- and trans isomers. Pure trans isomer was isolated by further chromatography. $^1$H NMR (300 MHz, CDCl$_3$) δ7.16 (m, 2H), 6.98 (t, J=9 Hz, 2H), 3.83 (dd, J=11, 3 Hz, 1H), 3.54 (dd, J=11, 7 Hz, 1H), 3.18 (dm, J=10 Hz, 1H), 2.95 (dm, J=12 Hz, 1H), 2.85 (m, 2H), 2.61 (m, 2H), 2.12 (dt, J=11, 3 Hz, 1H), 2.01 (t, J=11 Hz, 1H), 1.77 (m, 1H), 1.6–1.3 (m, 3H), 1.00 (d, J=6 Hz, 3H). Mass spec (ES+) m/z 252.1 (M+H$^+$, 100%).

Part D: Preparation of methanesulfonic acid trans-{1-[2-(4-fluorophenyl)ethyl]-4-methylpiperidin-3-ylmethyl} ester A solution of trans-{1-[2-(4-fluorophenyl)ethyl]-4-methylpiperidin-3-yl}-methanol (251 mg, 1.0 mmol) in dichloromethane (10 mL) was treated with triethylamine (280 µL, 2.0 mmol) and stirred on an ice-acetone bath. Methanesulfonyl chloride (85 µL, 1.1 mmol) was added dropwise, and the resulting solution was stirred at room temperature for 1.5 hours. The solution was concentrated under vacuum, and the residue was taken up in ethyl acetate and filtered. The filtrate was concentrated under vacuum to provide an orange gum (342 mg, quantitative) which was used without further purification. $^1$H NMR (300 MHz, CDCl$_3$) δ7.16 (m, 2H), 6.98 (t, J=9 Hz, 2H), 4.30 (dd, J=10, 3 Hz, 1H), 4.18 (dd, J=10, 7 Hz, 1H), 3.13 (dm, J=10 Hz, 1H), 3.02 (s+m, 4H), 2.83 (m, 2H), 2.66 (m, 2H), 2.07 (m, 2H), 1.76 (m, 2H), 1.43 (m, 2H), 1.02 (d, J=6, 3H).

Part E: Preparation of trans-3-azidomethyl-1-[2-(4-fluorophenyl)-ethyl]-4-methylpiperidine A mixture of methanesulfonic acid trans-{1-[2-(4-fluorophenyl)ethyl]-4-methylpiperidin-3-ylmethyl} ester (the crude material from Part D, about 1.0 mmol) and sodium azide (195 mg, 3 mmol) in N,N-dimethylformamide (4 mL) was stirred at 50° C. for 28 hours. The mixture was cooled to room temperature, filtered, and the solid was rinsed with ethyl acetate. The combined filtrates were diluted with ethyl acetate, and the resulting solution was washed twice with water, dried over sodium sulfate, and concentrated under vacuum. The residue was an orange oil (252 mg, 91%) which was used without further purification. $^1$H NMR (300 MHz, CDCl$_3$) δ7.17 (m, 2H), 6.98 (t, J=9 Hz, 2H), 3.50 (dd, J=12, 3 Hz, 1H), 3.25 (dd, J=12, 8 Hz, 1H), 3.08 (dm, J=10 Hz, 1H), 3.00 (dm, J=11 Hz, 1H), 2.83 (m, 2H), 2.60 (m, 2H), 2.04 (m, 1H), 1.88 (t, J=11 Hz, 1H), 1.71 (m, 1H), 1.60 (m, 1H), 1.5–1.3 (m, 2H), 1.00 (d, J=7 Hz, 3H).

Part F: Preparation of trans-1-[2-(4-fluorophenyl)ethyl]-4-methyl-piperidin-3-ylmethylamine A mixture of trans-3-azidomethyl-1-[2-(4-fluorophenyl)-ethyl]-4-methylpiperidine (252 mg, 911 µmol) and 10% palladium on charcoal (90 mg) in ethanol (25 mL) was shaken under a hydrogen atmosphere (60 psig) for 4 hours. The mixture was filtered and the filtrate was concentrated under vacuum to provide a sticky solid (226 mg, quantitative). $^1$H NMR (300 MHz, CDCl$_3$) δ7.16 (m, 2H), 6.97 (t, J=9 Hz, 2H), 3.12 (m, 1H), 2.98 (m, 1H), 2.93 (dd, J=13, 3 Hz, 1H), 2.80 (m, 2H), 2.58 (m, 3H), 1.99 (m, 1H), 1.80 (m, 1H), 1.8–1.6 (m, 3H), 1.5–1.1 (m, 3H), 0.97 (d, J=6 Hz, 3H). Mass spec (ES+) m/z 251.1 (M+H$^+$, 100%).

Part G: Preparation of 3-bromo-5-nitrobenzoic acid

A solution of 3-nitrobenzoic acid (16.7 g, 100 mmol) in trifluoroacetic acid (50 mL) and sulfuric acid (20 mL) at 50° C. N-Bromosuccinimide (26.7 g, 150 mmol) was added in three portions over 3 hours. The mixture was stirred for 16 hours and then cooled to room temperature. The mixture was poured into ice water (200 mL) and extracted three times with ethyl acetate. The combined organic layers were combined, dried over sodium sulfate and concentrated under vacuum. The residue was recrystallized from dichloromethane to provide a white solid (17.7 g, 72%). $^1$H NMR (300 MHz, DMSO-d$_6$) δ13.8 (bs, 1H), 8.60 (s, 1H), 8.55 (s, 1H), 8.37 (s, 1H).

Part H: Preparation of N-methyl-3-bromo-5-nitrobenzamide

A suspension of 3-bromo-5-nitrobenzoic acid (7.10 g, 28.9 mmol) in dichloromethane (50 mL) was treated with oxalyl chloride (5.04 mL, 57.7 mmol) and a few drops of N,N-dimethylformamide, producing gas evolution. After 2 hours, the mixture was concentrated to give an oil, which was dissolved in tetrahydrofuran and added dropwise to a stirred solution of methylamine in tetrahydrofuran (2.0 M, 28.9 mL, 57.7 mmol) at 0° C. After stirring overnight, the mixture was treated with water, ethyl acetate and 0.2 N aqueous hydrochloric acid. The layers were separated after mixing, and the organic phase was washed with 0.2 N aqueous hydrochloric acid, then with saturated aqueous sulfate and concentrated under vacuum to provide a yellow solid (7.0 g, 94%). $^1$H NMR (300 MHz, DMSO-d$_6$) δ9.92 (m, 1H), 8.64 (s, 1H), 8.53 (s, 1H), 8.43 (s, 1H), 2.81 (d, J=7 Hz, 3H).

Part I: Preparation of 5-(3-bromo-5-nitrophenyl)-1-methyl-1H-tetrazole

A suspension of N-methyl-3-bromo-5-nitrobenzamide (23.2 g, 90 mmol) in acetonitrile (200 mL) wad treated with sodium azide (5.82 g, 90 mmol) and cooled to 0° C. Trifluoromethanesulfonic anhydride (15.1 mL, 90 mmol) was added dropwise very slowly. After the mixture was stirred for 4 hours, saturated aqueous sodium hydrogen carbonate was added and the mixture was stirred for 10 minutes. The mixture was extracted with ethyl acetate and the organic phase was washed twice with saturated aqueous sodium hydrogen carbonate, once with saturated sodium chloride, and dried over magnesium sulfate. Concentration provided a dark amber oil which was stirred in ethyl acetate (25 mL) to provide a precipitate, which was isolated by filtration and dried to provide a tan solid (10.5 g). The filtrate was purified by silica gel chromatography, eluting with dichloromethane, to provide additional solid (9.0 g, 76% total). $^1$H NMR (300 MHz, CDCl$_3$) δ8.60 (s, 1H), 8.55 (s, 1H), 8.32 (s, 1H), 7.26 (s, 1H), 4.29 (s, 3H).

Part J: Preparation of 1-methyl-5-(3-nitro-5-vinylphenyl)-1H-tetrazole

A mixture of 5-(3-bromo-5-nitrophenyl)-1-methyl-1H-tetrazole (19.50 g, 68.6 mmol), tributylvinyl tin (20.06 mL, 68.6 mmol) and tetrakis(triphenylphosphine)palladium (1.59 g, 1.37 mmol) in toluene was heated at reflux for 2 hours. The mixture was cooled to room temperature and concentrated under vacuum. The residue was purified by silica gel chromatography, eluting with a step gradient from dichloromethane to 50% ethyl acetate in dichloromethane, to provide a solid (22.0 g) containing a tributyltin-containing impurity. $^1$H NMR (300 MHz, CDCl$_3$) δ8.49 (d, J=7 Hz, 2H), 8.19 (s, 1H), 6.86 (m, 1H), 6.05 (d, J=15 Hz, 1H), 5.60 (d, J=7 Hz, 1H), 4.28 (s, 3H).

Part K: Preparation of 3-ethyl-5-(1-methyl-1H-tetrazole-5-yl)aniline

A mixture of impure 1-methyl-5-(3-nitro-5-vinylphenyl)-1H-tetrazole (17.0 g) and palladium hydroxide on charcoal (3.0 g) in methanol (50 mL) was shaken under a hydrogen atmosphere (50 psig) for 4 hours. The mixture was filtered and the filtrate was concentrated under vacuum to provide an amber solid (14.3 g). $^1$H NMR (300 MHz, CDCl$_3$) δ6.90 (s, 1H), 6.87 (s, 1H), 6.73 (s, 1H), 4.16 (s, 3H), 3.95 (bs, 2H), 2.65 (q, J=7 Hz, 2H), 1.22 (t, J=7 Hz, 3H).

Part L: Preparation of [3-ethyl-5-(1-methyl-1H-tetrazol-5-yl)phenyl]-carbamic acid phenyl ester A solution of 3-ethyl-5-(1-methyl-1H-tetrazol-5-yl) aniline (3.83 g, 19 mmol) in tetrahydrofuran was treated with 2,6-lutidine (2.17 mL, 19 mmol) and cooled to 0° C. A solution of phenyl chloroformate (2.36 mL, 19 mmol) in tetrahydrofuran was added dropwise. The mixture was stirred for 1 hour, then was diluted with ethyl acetate and 0.1 N aqueous hydrochloric acid. The separated organic phase was washed twice with 0.1 N aqueous hydrochloric acid, then with saturated aqueous sodium chloride. The solution was dried over magnesium sulfate and concentrated under vacuum to provide a tan solid (6.00 g, quantitative). $^1$H NMR (300 MHz, CDCl$_3$) δ7.86 (s, 1H), 7.5–7.3 (m, 5H), 7.3–7.1 (m, 3H), 4.17 (s, 3H), 2.71 (q, J=7 Hz, 2H), 1.27 (t, J=7 Hz, 3H).

Part M: Preparation of 1-[3-ethyl-5-(1-methyl-1H-tetrazol-5-yl)phenyl]-3-{trans-1-[2-(4-fluorophenyl)-ethyl]-4-methylpiperidin-3-ylmethyl}-urea A solution of trans-1-[2-(4-fluorophenyl)ethyl]-4-methyl-piperidin-3-ylmethylamine (12 mg, 46 μmol) and [3-ethyl-5-(1-methyl-1H-tetrazol-5-yl)phenyl]-carbamic acid phenyl ester (15 mg, 46 μmol) in N,N-dimethylformamide (0.5 mL) was treated with triethylamine (13 μL, 93 μmol). After 23 hours, the mixture was concentrated under vacuum. The residue was purified by flash chromatography, eluting with 3% methanol in dichloromethane containing 0.3% aqueous ammonium hydroxide, provided an amorphous solid (19 mg, 86%). $^1$H NMR (300 MHz, CDCl$_3$) δ7.71 (s, 1H), 7.64 (s, 1H), 7.11 (m, 3H), 6.91 (t, J=9 Hz, 2H), 4.17 (s, 3H), 3.6–3.3 (m, 3H), 3.2–2.9 (m, 6H), 2.66 (q, J=7 Hz, 2H), 2.50 (m, 1H), 1.9–1.7 (m, 3H), 1.42 (m, 1H), 1.24 (t, J=7 Hz, 3H), 1.01 (d, J=7 Hz, 3H). Mass spec (ES+) m/z 480.4 (M+H$^+$, 100%).

Example 6

Part A: Preparation of trans-1-[2-(4-fluorophenyl) ethyl]-4-methyl-2,6-dioxopiperidine-3-carbonitrile A solution of ethyl cyanoacetate (4.26 mL, 40 mmol) and trans-2-butenoic acid [2-(4-fluoro-phenyl)ethyl]amide (4.15 g, 20 mmol) in tert-butanol (60 mL) was treated with a solution of potassium tert-butoxide in tetrahydrofuran (1.0 M, 40 mL, 40 mmol) and the mixture was heated at 80° C. The mixture was cooled to room temperature after 16.5 hours and diluted with 1.0 N aqueous hydrochloric acid. The mixture was concentrated under vacuum to remove the organic solvents, providing a suspension of solid in the aqueous residue. This was collected by filtration, dried, and purified by recrystallization from 95% ethanol to provide a white solid (5.13 g, 93%). $^1$H NMR (300 MHz, CDCl$_3$) δ7.19 (m, 2H), 7.00 (t, J=9 Hz, 2H), 4.02 (m, 2H), 3.41 (d, J=11 Hz, 1H), 2.91 (m, 1H), 2.83 (t, J=8 Hz, 2H), 2.5–2.3 (m, 2H), 1.31 (d, J=6 Hz, 3H). Mass spec (CI) m/z 275.0 (M+H$^+$, 100%).

Part B: Preparation of cis- and trans-1-[2-(4-fluorophenyl)ethyl]-4-methyl-piperidin-3-ylmethylamine A solution of trans-1-[2-(4-fluorophenyl)ethyl]-4-methyl-2,6-dioxopiperidine-3-carbonitrile (1.0 g, 3.64 mmol) in tetrahydrofuran (10 mL) was added over 5 minutes to an ice-cold solution of lithium aluminum hydride (1.0 M in tetrahydrofuran, 16 mL, 16 mmol). The solution was stirred at room temperature for 26 hours, then was quenched by the slow dropwise addition of water (610 μL), 15% aqueous sodium hydroxide (610 μL), and water (1.82 mL). The resulting suspension was stirred for 20 minutes, then filtered and the solid washed with ethyl acetate. The combined filtrates were concentrated under vacuum to provide an oil. This was purified by flash chromatography, eluting with 5% methanol in hydroxide, to provide the trans isomer as a pale yellow (55 mg, 6%). For the cis isomer: $^1$H NMR (300 MHz, CDCl$_3$) δ7.14 (m, 2H), 6.95 (t, J=9 Hz, 2H), 2.77 (t, J=8 Hz, 2H), 2.66 (m, 2H), 2.52 (m, 3H), 2.42 (m, 2H), 1.87 (m, 1H), 1.66 (m, 3H), 1.55 (m, 1H), 0.89 (d, J=7 Hz, 3H)

Part C: Preparation of 1-[3-(1-methyl-1H-tetrazol-5-yl)phenyl]-3-{cis-1-[2-(4-fluorophenyl)-ethyl]-4-methylpiperidin-3-ylmethyl}-urea A solution of cis-1-[2-(4-fluorophenyl)ethyl]-4-methyl-piperidin-3-ylmethylamine (54 mg, 215 μmol) and [3-(1-methyl-1H-tetrazol-5-yl)phenyl]-carbamic acid phenyl ester (64 mg, 215 μmol) in N,N-dimethylformamide (2 mL) was treated with triethylamine (60 μL, 431 μmol). After 18 hours, the mixture was concentrated under vacuum. The residue was purified by flash chromatography, eluting with 3% methanol in dichloromethane containing 0.3% aqueous ammonium hydroxide, to provide an amorphous solid (73 mg, 75%). $^1$H NMR (300 MHz, CDCl$_3$) δ7.95 (s, 1H), 7.64 (d, J=7 Hz, 1H), 7.41 (t, J=8 Hz, 1H), 7.29 (m, 1H), 7.11 (m, 2H), 6.97 (t, J=9 Hz, 2H), 4.17 (s, 3H), 3.42 (m, 1H), 3.26 (m, 1H), 3.1–2.5 (m, 8H), 2.1–1.6 (m, 4H), 0.99 (d, J=7 Hz, 3H). Mass spec (AP+) m/z 452.1 (M+H$^+$).

Example 7

Part A: Preparation of 4-oxopiperidine-1,3-dicarboxylic acid 1-tert-butyl ester 3-methyl ester A slurry of 4-oxopiperidine-3-carboxylic acid methyl ester (24.85 g, 128 mmol) in tetrahydrofuran (165 mL) was treated at room temperature with triethylamine (36.5 mL, di-tert-butyl dicarbonate (30.8 g, 141 mmol) over a period of about 3 minutes. The mixture was stirred for 23.5 hours, then was filtered and the filtrate was concentrated under vacuum. The solid and the solid residue from the filtrate were combined and dissolved in water and ethyl acetate. The layers were separated and the organic phase was washed again with water, followed by extraction of the combined aqueous phases with ethyl acetate. The combined organic phases were dried over sodium sulfate and concentrated to provide a viscous yellow oil (34.8 g, quantitative yield) which was enolic by NMR. $^1$H NMR (300 MHz, CDCl$_3$) δ11.99 (s, 1H), 4.07 (bs, 2H), 3.79 (s, 3H), 3.58 (t, J=6 Hz, 2H), 2.39 (bt, J=6 Hz, 2H), 1.49 (s, 9H).

Part B: Preparation of 4-benzylamino-5,6-dihydro-2H-pyridine-1,3-dicarboxylic acid 1-tert-butyl ester 3-methyl ester A solution of 4-oxopiperidine-1,3-dicarboxylic acid 1-tert-butyl ester 3-methyl ester (2.57 g, 10 mmol), benzylamine (1.20 mL, 11 mmol) and p-toluenesulfonic acid hydrate (19 mg, 0.1 mmol) in toluene (40 mL) was heated at reflux under a Dean-Stark trap for 22.75 hours. The mixture was cooled to room temperature and concentrated under vacuum to provide a yellow gummy solid (3.86 g), used without further purification. $^1$H NMR (300 MHz, CDCl$_3$) δ9.25 (bt, J=6 Hz, 1H), 7.4–7.1 (m, 5H), 4.42 (d, J=6 Hz, 2H), 4.11 (s, 2H), 3.71 (s, 3H), 3.49 (t, 2H), 2.38 (m, 2H), 1.48 (s, 9H).

Part C: Preparation of cis-4-benzylaminopiperidine-1,3-dicarboxylic acid 1-tert-butyl ester 3-methyl ester A solution of crude 4-benzylamino-5,6-dihydro-2H-pyridine-1,3-dicarboxylic acid 1-tert-butyl ester 3-methyl ester (3.86 g, approximately 10 mmol) in acetonitrile (30 mL) and acetic acid (20 mL) was stirred on an ice bath and treated with sodium triacetoxyborohydride (4.83 g, 22.5 mmol). After 1.75 hours, additional sodium triacetoxyborohydride (4.82 g, 22.5 mmol) was added. After 2.25 hours, the mixture was concentrated under vacuum, and the residue was diluted with 1.0 N aqueous sodium hydroxide (50 mL), and the mixture was stirred on ice and the pH was adjusted to 10 with 50% aqueous sodium hydroxide. The mixture was extracted with dichloromethane, and the organic phase was dried over sodium sulfate and concentrated to provide an orange gum. Purification by flash chromatography with 40% ethyl acetate in hexane provided a colorless viscous oil (2.86 g, 82% for two steps). $^1$H NMR (300 MHz, CDCl$_3$) δ7.4–7.3 (m, 5H), 4.03 (m, 1H), 3.88 (ab pattern, 2H), 3.73 (m, 1H), 3.71 (s, 3H), 3.38 (m, 1H), 3.20 (m, 1H), 3.12 (m, 1H), 2.90 (m, 1H), 1.91 (m, 1H), 1.78 (m, 1H), 1.46 (s, 9H).

Part D: Preparation of cis- and trans-4-benzylaminopiperidine-1,3-dicarboxylic acid 1-tert-butyl ester 3-ethyl ester A solution of cis-4-benzylaminopiperidine-1,3-dicarboxylic acid 1-tert-butyl ester 3-methyl ester (2.86 g, 8.2 mmol) in ethanol (100 mL) was treated with potassium carbonate (5.67 g, 41 mmol) and heated at reflux for 5 hours. The mixture was cooled and filtered, and the filtrate was concentrate under vacuum. Purification by flash chromatography, eluting with 25% and trans isomers as a colorless viscous oil (1.88 g, 62%) which was used directly in the next reaction.

Part E: Preparation of cis- and trans-4-(benzyl-methyl-amino)-piperidine-1,3-dicarboxylic acid 1-tert-butyl ester 3-ethyl ester A solution of the mixture from Part D (1.88 g, 5.18 mmol) in acetonitrile (20 mL) was treated with aqueous formaldehyde (37%, 5 mL) and then with sodium cyanoborohydride (978 mg, 15.6 mmol). After 15 minutes and again after 30 minutes, a few drops of acetic acid were added to reduce the pH of the mixture from 9–10 to 6–7. Additional sodium cyanoborohydride (approximately 250 mg) was added, and the mixture was stirred for 45 minutes more. The mixture was concentrated under vacuum. The residue was dissolved in 1.0 N aqueous sodium hydroxide and extracted with dichloromethane (three times). The combined organic phases were dried over sodium sulfate and concentrated under vacuum. The residue was purified by flash chromatography, eluting with 10% ethyl acetate in hexane, to provide the trans isomer as a colorless viscous oil (1.25 g, 64%). $^1$H NMR (300 MHz, CDCl$_3$) δ7.3–7.2 (m, 5H), 4.3–4.1 (m, 4H), 3.71 (d, J=13 Hz, 1H), 3.48 (d, J=13 Hz, 1H), 3.02 (m, 1H), 2.88 (m, 1H), 2.69 (m, 2H), 2.18 (s, 3H), 1.83 (m, 1H), 1.48 (m+s, 10H), 1.27 (t, J=7 Hz, 3H). Mass spec (ES+) m/z 377.3 (M+H$^+$). Further elution with 15% ethyl acetate in hexane provided the cis isomer as a colorless viscous oil (0.465 g, 24%). $^1$H NMR (300 MHz, CDCl$_3$) δ7.30 (m, 5H), 4.5–4.1 (m, 4H), 3.77 (d, J=13 Hz, 1H), 3.53 (d, J=13 Hz, 1H), 3.1–2.7 (m, 4H), 2.37 (m, 1H), 2.20 (s, 3H), 1.70 (m, 1H), 1.46 (s, 9H), 1.28 (m, 3H). Mass spec (ES+) m/z 377.3 (M+H$^+$).

Part F: Preparation of trans-4-(benzyl-methyl-amino)-piperidine-3-carboxylic acid ethyl ester dihydrochloride A solution of trans-4-(benzyl-methyl-amino)-piperidine-1,3-dicarboxylic acid 1-tert-butyl ester 3-ethyl ester (235 mg, 624 μmol) in ethyl acetate (2 mL) was stirred on an ice bath and treated with 4.0 N hydrogen chloride in dioxane (6 mL). The bath was removed, and the mixture was stirred at room temperature for 18 hours. The mixture was then concentrated under vacuum, and the residue was stirred in ether, and the ether was decanted. The ether treatment was repeated twice more, and the residue was dried under vacuum to provide a white powder (231 mg) which was used without purification. $^1$H NMR (300 MHz, methanol-d$_4$) δ7.60 (m, 2H), 7.54 (m, 3H), 4.6–3.8 (m, 6H), 3.68 (m, 2H), 3.4–3.0 (m, 2H), 2.90 (s, 3H), 2.52 (m, 1H), 2.28 (m, 1H), 1.35 (m, 3H).

Part G. Preparation of trans-4-(benzyl-methyl-amino)-1-[2-(4-fluorophenyl)-ethyl]-piperidine-3-carboxylic acid ethyl ester A solution of toluene-4-sulfonic acid 2-(4-fluorophenyl)-ethyl ester (containing 10% by weight of 2-(4-fluorophenyl) ethanol; 206 mg, 630 μmol), trans-4-(benzyl-methyl-amino)-piperidine-3-carboxylic acid ethyl ester dihydrochloride (220 mg, 630 μmol) and potassium carbonate (261 mg, 1.9 mmol) in acetonitrile (6 mL) was heated at reflux for 17 hours. The mixture was cooled and filtered, the solid was washed with acetonitrile, and the filtrate was concentrated under vacuum. The residue was purified by flash chromatography, eluting with 20%, then 30% ethyl acetate in hexane, to provide an oil (164 mg, 65%). $^1$H NMR (300 MHz, CDCl$_3$) δ7.28 (m, 5H), 7.16 (m, 2H), 6.98 (t, J=9 Hz, 2H), 4.20 (m, 2H), 3.75 (d, J=13 Hz, 1H), 3.48 (d, J=13 Hz, 1H), 3.14 (m, 2H), 2.88 (m, 2H), 2.80 (m, 2H), 2.62 (m, 2H), 2.29 (m, 1H), 2.20 (s, 3H), 1.87 (m, 1H), 1.70 (m, 2H), 1.28 (t, J=7 Hz, 3H).

Part H. Preparation of trans-{4-(benzyl-methyl-amino)-1-[2-(4-fluorophenyl)-ethyl]-piperidin-3-yl}-methanol A solution of trans-4-(benzyl-methyl-amino)-1-[2-(4-fluorophenyl)-ethyl]-piperidine-3-carboxylic acid ethyl ester (144 mg, 361 μmol) in tetrahydrofuran (1 mL) was treated with a solution of lithium aluminum hydride (1.0 M in tetrahydrofuran, 723 μL, 723 μmol). The mixture was stirred at room temperature for 2.5 hours, then was treated very slowly with 28 μL of water, followed by 28 μL of 15% aqueous sodium hydroxide, then by 84 μL of water. The mixture was filtered and the solid was washed with ether. The filtrate and washes were combined and concentrated under vacuum to provide a white solid (116 mg, 90%). $^1$H NMR (300 MHz, CDCl$_3$) δ7.34 (m, 5H), 7.15 (m, 2H), 6.98 (t, J=9 Hz, 2H), 6.26 (bs, 1H), 3.78 (d, J=13 Hz, 1H), 3.60 (m, 2H), 3.50 (m, 1H), 3.10 (m, 1H), 2.87 (m, 1H), 2.78 (m, 2H), 2.54 (m, 2H), 2.28 (s, 3H), 2.20 (m, 1H), 1.88 (m, 2H), 1.75 (m, 1H), 1.58 (m, 1H). Mass spec (ES+) m/z 357.3 (M+H$^+$).

Part I. Preparation of methanesulfonic acid trans-4-(benzyl-methyl-amino)-1-[2-(4-fluorophenyl)-ethyl]-piperidin-3-ylmethyl ester A solution of -{4-(benzyl-methyl-amino)-1-[2-(4-fluorophenyl)-ethyl]-piperidin-3-yl}-methanol (105 mg, 294

μmol) and triethylamine (62 μL, 442 μmol) in dichloromethane (1 mL) was stirred on an ice bath and treated with a solution of methanesulfonyl chloride (25 μL, 320 μmol) in dichloromethane (0.5 mL). After 1.75 hours, the mixture was concentrated and the residue was dissolved in ethyl acetate. The suspension was filtered, the solid was rinsed with ethyl acetate, and the filtrate was concentrated under vacuum to provide a yellowish gum (139 mg) which was used without purification. $^1$H NMR (300 MHz, CDCl$_3$) δ7.32 (m, 5H), 7.17 (m, 2H), 6.99 (t, J=9 Hz, 2H), 4.57 (dd, J=10, 3 Hz, 1H), 4.29 (m, 1H), 3.72 (d, J=13 Hz, 1H), 3.50 (d, J=13 Hz, 1H), 3.4–3.1 (m, 2H), 3.00 (s, 3H), 2.83 (m, 2H), 2.70 (m, 2H), 2.48 (m, 1H), 2.35 (m, 1H), 2.22 (s, 3H), 2.07 (m, 2H), 2.0–1.7 (m, 2H).

Part J. Preparation of trans-{3-azidomethyl-1-[2-(4-fluoro-phenyl)-ethyl]-piperidin-4-yl}-benzyl-methylamine A mixture of crude methanesulfonic acid trans-4-(benzyl-methyl-amino)-1-[2-(4-fluorophenyl)-ethyl]-piperidin-3-ylmethyl ester (139 mg, 294 μmol) and sodium azide (58 mg, 882 μmol) in N,N-dimethylformamide (2 mL) was heated at 60° C. for 20 hours, then cooled to room temperature. The mixture was diluted with ethyl acetate, washed three times with water, dried over sodium sulfate, and concentrated under vacuum to provide a gum (106 mg, 95%) which was used without purification. $^1$H NMR (300 MHz, CDCl$_3$) δ7.33 (m, 5H), 7.16 (m, 2H), 6.99 (t, J=9 Hz, 2H), 3.70 (m, 2H), 3.52 (d, J=13 Hz, 1H), 3.41 (m, 1H), 3.20 (m, 2H), 2.83 (m, 2H), 2.61 (m, 2H), 2.42 (m, 1H), 2.3–1.8 (m, 4H), 2.19 (s, 3H), 1.75 (m, 1H).

Part K. Preparation of trans-{3-aminomethyl-1-[2-(4-fluoro-phenyl)-ethyl]-piperidin-4-yl}-benzyl-methylamine A mixture of crude trans-{3-azidomethyl-1-[2-(4-fluorophenyl)-ethyl]-piperidin-4-yl}-benzyl-methylamine (106 mg, 278 μmol) and 10% palladium on charcoal (20 mg) in ethanol (5 mL) was stirred at room temperature under a hydrogen atmosphere. After 1.75 hours, the mixture was filtered through Celite and the solids were rinsed with ethanol. The filtrate was concentrated to provide a gum (98 mg, quantitative). $^1$H NMR (300 MHz, CDCl$_3$) δ7.33 (m, 5H), 7.15 (m, 2H), 6.98 (t, J=9 Hz, 2H), 3.72 (d, J=13 Hz, 1H), 3.55 (d, J=13 Hz, 1H), 3.07 (m, 2H), 2.9–2.7 (m, 4H), 2.55 (m, 2H), 2.37 (m, 1H), 2.23 (s, 3H), 2.19 (m, 2H), 2.0–1.6 (m, 5H). Mass spec (AP+) m/z 356.2 (M+H$^+$).

Part L. Preparation of trans-1-{4-(benzyl-methylamino)-1-[2-(4-fluorophenyl)-ethyl]-piperidin-3-ylmethyl}-3-[3-ethyl-5-(1-methyl-1H-tetrazol-5-yl)-phenyl]-urea A solution of trans-{3-aminomethyl-1-[2-(4-fluorophenyl)-ethyl]-piperidin-4-yl}-benzyl-methylamine (96 mg, 270 μmol), [3-ethyl-5-(1-methyl-1H-tetrazol-5-yl)phenyl]-carbamic acid phenyl ester (87 mg, 270 μmol) and triethylamine (75 μL, 540 μmol) in N,N-dimethylformamide (2 mL) was stirred at room temperature for 20 hours. The solvent was removed under vacuum and the residue was dissolved in dichloromethane. The solution was washed with 1.0 N aqueous sodium hydroxide, then with water, and dried over sodium sulfate and concentrated under vacuum. The residue was purified by flash chromatography, eluting with 4% methanol in dichloromethane containing 0.4% (112 mg, 71%). $^1$H NMR (300 MHz, CDCl$_3$) δ7.68 (s, 1H), 7.39 (m, 6H), 7.20 (s, 1H), 7.15 (m, 2H), 6.97 (t, J=9 Hz, 2H), 4.14 (s, 3H), 3.80 (m, 1H), 3.7–3.4 (m, 2H), 3.3–3.1 (m, 3H), 2.82 (m, 2H), 2.7–2.5 (m, 5H), 2.29 (s, 3H), 2.1–1.6 (m, 7H), 1.20 (t, J=7 Hz, 3H). Mass spec (ES+) m/z 585.6 (M+H$^+$).

Example 8

Preparation of trans-1-{4-methylamino-1-[2-(4-fluorophenyl)-ethyl]-piperidin-3-ylmethyl}-3-[3-ethyl-5-(1-methyl-1H-tetrazol-5-yl)-phenyl]-urea A solution of trans-1-{4-(benzyl-methylamino)-1-[2-(4-fluorophenyl)-ethyl]-piperidin-3-ylmethyl}-3-[3-ethyl-5-(1-methyl-1H-tetrazol-5-yl)-phenyl]-urea (95 mg, 162 μmol) in methanol (20 mL) was combined with Pearlman's catalyst (20% palladium hydroxide on charcoal, 100 mg) and shaken under a hydrogen atmosphere (60 psig) for 15 hours. The mixture was filtered through Celite and the solids were washed with methanol. The filtrate was concentrated under vacuum to provide a pale tan solid (78 mg, 97%). $^1$H NMR (300 MHz, CDCl$_3$) δ7.78 (s, 1H), 7.36 (s, 1H), 7.16 (m, 2H), 7.13 (s, 1H), 6.96 (t, J=9 Hz, 2H), 4.14 (s, 3H), 3.66 (m, 1H), 3.4–3.1 (m, 4H), 2.95 (s, 3H), 2.9–2.3 (m, 12H), 2.18 (m, 2H), 1.22 (t, J=8 Hz, 3H). Mass spec (ES+) m/z 495.2 (M+H$^+$).

Example 9

Preparation of trans-N-{3-{3-[3-ethyl-5-(1-methyl-1H-tetrazol-5-yl)-phenyl]-ureidomethyl}-1-[3-(4-fluoro-phenyl)-propyl]-piperidin-4-yl}-N-methyl-acetamide A solution of trans-1-{4-methylamino-1-[2-(4-fluorophenyl)-ehtyl]-piperidin-3-ylmethyl}-3-[-3ethyl-5-(1-methyl-1H-tetrazol-5-yl)-phenyl]-urea (34 mg, 69 μmol) in dichloromethane (1 mL) was treated with triethylamine (29 μL, 206 μmol) and stirred on an ice bath. Acetyl chloride (5.4 μL, 75 μmol) was added, and the mixture was stirred at room temperature. After 19 hours, additional acetyl chloride (2 μL) was added, and 5 hours later the mixture was concentrated under vacuum. The residue was purified by flash chromatography, eluting with 2.5% methanol in dichloromethane containing 0.25% aqueous ammonium hydroxide, to provide an amorphous solid (26 mg, 72%). $^1$H NMR (300 MHz, CDCl$_3$) δ7.72 (s, 1H), 7.46 (s, 1H), 7.41 (s, 1H), 7.20 (s, 1H), 7.13 (m, 2H), 6.95 (t, J=9 Hz, 2H), 6.12 (bm, 1H), 4.40 (bm, 1H), 4.18 (s, 3H), 3.63 (m, 1H), 3.2–3.0 (m, 2H), 2.92 (s, 3H), 2.8–2.3 (m, 7H), 2.16 (s, 3H), 2.1–1.8 (m, 4H), 1.65 (m, 1H), 1.24 (t, J=7 Hz, 3H). Mass spec (ES+) m/z 537.4 (M+H$^+$).

Example 10

Preparation of trans-N-{3-{3-[3-ethyl-5-(1-methyl-1H-tetrazol-5-yl)-phenyl]-ureidomethyl}-1-[3-(4-fluoro-phenyl)-propyl]-piperidin-4-yl}-N-methyl-methanesulfonamide A solution of trans-1-{4-methylamino-1-[2-(4-fluorophenyl)-ethyl]-piperidin-3-ylmethyl}-3-[3-ethyl-5-(1-methyl-1H-tetrazol-5-yl)-phenyl]-urea (34 mg, 69 μmol) in dichloromethane (1 mL) was treated with triethylamine (29 μL, 206 μmol) and stirred on an ice bath. Methanesulfonyl chloride (5.8 μL, 75 μmol) was added, and the mixture was stirred at room temperature. After 19 hours, additional methanesulfonyl chloride (2 μL) was added, followed 60 minutes later by additional triethylamine (20 μL). After 30 minutes more, the solution was concentrated under vacuum, and the residue was purified by flash chromatography, eluting with 2.5% methanol in dichloromethane containing 0.25% aqueous ammonium hydroxide, to provide an amorphous solid (24 mg, 61%). $^1$H NMR (300 MHz, CDCl$_3$) $\delta$7.67 (s, 1H), 7.47 (s, 1H), 7.36 (bs, 1H), 7.18 (s, 1H), 7.12 (m, 2H), 6.95 (t, J=9 Hz, 2H), 5.83 (bt, J=5 Hz, 1H), 4.17 (s, 3H), 3.60 (m, 2H), 3.2–3.0 (m, 2H), 2.89 (s, 3H), 2.83 (s, 3H), 2.8–2.6 (m, 4H), 2.55 (m, 2H), 2.2–1.8 (m, 4H), 1.70 (m, 1H), 1.24 (t, J=7 Hz, 3H). Mass spec (ES+) m/z 573.4 (M+H$^+$).

Example 11

Part A. Preparation of (S)-3-{3-[3-ethyl-5-(1-methyl-1H-tetrazol-5-yl)-phenyl]-ureidomethyl}-piperidine-1-carboxylic acid tert-butyl ester Racemic 3-hydroxymethylpiperidine-1-carboxylic acid tert-butyl ester was resolved using the procedure of B. Wirz and W. Walther, Tetrahedron Asymm. 1992, 3, 1049. The (R) isomer was converted into (S)-3-aminomethyl-piperidine-1-carboxylic acid tert-butyl ester by the method of K. Hilpert et al., J. Med. Chem. 1994, 37, 3889. A solution of this material (119 mg, 556 μmol) in N,N-dimethylformamide (4 mL) was treated with [3-ethyl-5-(1-methyl-1H-tetrazol-5-yl)-phenyl]-carbamic acid phenyl ester (180 mg, 556 μmol) and triethylamine (155 μL, 1.11 mmol) and the mixture was stirred at room temperature for 21 hours. The mixture was concentrated under vacuum, and the residue was dissolved in dichloromethane. The solution was washed with 1.0 N aqueous sodium hydroxide, dried over sodium sulfate and concentrated under vacuum. The residue was purified by flash chromatography, elution with 70% ethyl acetate in hexane, to provide a white glassy solid (193 mg, 78%). $^1$H NMR (300 MHz, CDCl$_3$) $\delta$7.64 (s, 1H), 7.55 (s, 1H), 7.18 (s, 1H), 4.20 (s, 3H), 3.9–3.6 (m, 3H), 3.28 (m, 1H), 3.05 (m, 2H), 1.83 (m, 1H), 2.66 (q, J=8 Hz, 2H), 1.9–1.5 (m, 5H), 1.46 (s, 9H), 1.24 (t, J=8 Hz, 3H).

Part B. Preparation of (S)-1-[3-ethyl-5-(1-methyl-1H-tetrazol-5-yl)-phenyl]-3-piperidin-3-ylmethyl-urea hydrochloride A solution of (S)-3-{3-[3-ethyl-5-(1-methyl-1H-tetrazol-5-yl)-phenyl]-ureidomethyl}-piperidine-1-carboxylic acid tert-butyl ester (200 mg, 450 μmol) in ethyl acetate (5 mL) was treated with a solution of hydrogen chloride in dioxane (4.0 N, 2 mL, 8 mmol) and stirred at room temperature for 6 hours. The mixture was concentrated, and the residue was triturated twice in diethyl ether and dried under vacuum to provide a white powder (165 mg, 97%). $^1$H NMR (300 MHz, DMSO-d$_6$) $\delta$9.24 (s, 1H), 8.89 (bm, 1H), 8.68 (bm, 1H), 7.81 (s, 1H), 7.43 (s, 1H), 7.22 (s, 1H), 6.79 (t, J=6 Hz, 1H), 4.16 (s, 3H), 3.40 (m, 2H), 3.20 (m, 2H), 3.05 (m, 2H), 2.9–2.5 (m, 4H), 2.0–1.6 (m, 4H), 1.21 (t, J=8 Hz, 3H).

Part C. Preparation of (S)-1-[3-ethyl-5-(1-methyl-1H-tetrazol-5-yl)-phenyl]-3-{1-[2-(4-fluorophenyl)-2-oxo-ethyl]-piperidin-3-ylmethyl}-urea A solution of (S)-1-[3-ethyl-5-(1-methyl-1H-tetrazol-5-yl)-phenyl]-3-piperidin-3-ylmethyl-ureahydrochloride (50 with 2-chloro-4'-fluoroacetophenone (27 mg, 158 μmol) and minutes. Additional triethylamine (73 μL, 526 μμmol) and 2-chloro-4'-fluoroacetophenone (ca. 5 mg) were added and stirring was continued for 60 minutes more. The mixture was concentrated under vacuum, and the residue was purified by flash chromatography, eluting with 3% methanol in dichloromethane, containing 0.3% aqueous ammonia, to provide a tan glassy solid (51 mg, 81%). $^1$H NMR (300 MHz, CDCl$_3$) $\delta$8.02 (m, 3H), 7.70 (s, 1H), 7.59 (s, 1H), 7.13 (m, 3H), 6.64 (bs, 1H), 4.20 (s, 3H), 3.85 (ab, J=18 Hz, 2H), 3.30 (m, 2H), 2.9–2.6 (m, 4H), 2.37 (m, 2H), 2.0–1.6 (m, 5H), 1.25 (t, J=8 Hz, 3H). Mass spec (ES+) m/z 480.4 (M+H$^+$).

Example 12

Preparation of (S)-1-[3-ethyl-5-(1-methyl-1H-tetrazol-5-yl)-phenyl]-3-{1-[2-(4-fluorophenyl)-2-hydroxyimino-ethyl]-piperidin-3-ylmethyl}-urea A solution of (S)-1-[3-ethyl-5-(1-methyl-1H-tetrazol-5-yl)-phenyl]-3-{1-[2-(4-fluorophenyl)-2-oxo-ethyl]-piperidin-3-ylmethyl}-urea (20 mg, 42 μmol) in pyridine (0.5 mL) was treated with hydroxylamine hydrochloride (6 mg, 82 μmol) and stirred at room temperature for 16 hours. The solution was concentrated under vacuum, and the residue was purified by flash chromatography, eluting with 2.5% methanol in dichloromethane, containing 0.25% aqueous ammonia, to provide a white glassy solid (10 mg, 50%). $^1$H NMR (300 MHz, CDCl$_3$) $\delta$8.14 (s, 1H), 7.59 (s, 1H), 7.54 (m, 2H), 7.48 (s, 1H), 7.28 (s, 1H), 7.00 (t, J=9 Hz, 2H), 6.15 (bt, 1H), 4.16 (s, 3H), 3.78 (ab, J=15 Hz, 2H), 3.19 (m, 2H), 3.06 (m, 1H), 2.95 (m, 1H), 2.60 (q, J=8 Hz, 2H), 2.26 (m, 1H), 2.09 (m, 1H), 1.78 (m, 3H), 1.60 (m, 1H), 1.19 (t, J=8 Hz, 3H), 1.10 (m, 1H). Mass spec (ES+) m/z 495.4 (M+H$^+$).

Example 13

Preparation of 1-[3-ethyl-5-(1-methyl-1H-tetrazol-5-yl)-phenyl]-3-{1-[2-(4-fluorophenyl)-2-(RS)-hydroxyethyl]-(S)-piperidin-3-ylmethyl}-urea A solution of (S)-1-[3-ethyl-5-(1-methyl-1H-tetrazol-5-yl)-phenyl]-3-{1-[2-(4-fluorophenyl)-2-oxo-ethyl]-piperidin-3-ylmethyl}-urea (23 mg, 48 μmol) in methanol (1.0 mL) was treated with sodium borohydride (4.5 mg, 120 μmol) and the mixture was stirred at room temperature. After 3 hours and again after 5 hours, additional sodium borohydride (ca. 2 mg) was added. After a total of 7 hours, water (0.5 mL) was added, and the mixture was concentrated under vacuum. The residue was purified by flash column chromatography, eluting with 3% methanol in dichloromethane containing 0.3% aqueous ammonia, to provide a white glassy solid (21 mg, 91%). This material was a 1:1 mixture of epimers at the hydroxyl group. $^1$H NMR (300 MHz, CDCl$_3$) $\delta$8.25+8.16 (2s, 1H), 7.75+7.70 (2s, 1H), 7.54 (s, 1H), 7.30 (m, 2H), 7.05 (s, 1H), 7.00 (t, J=9 Hz, 2H), 6.21+6.13 (2 bt, 1H), 4.71 (m, 1H), 4.15+4.14 (2 s, 3H), 3.3–3.1 (m, 3H), 3.0–2.7 (m, 3H), 2.60 (q, J=8 Hz, 2H), 2.5–2.3 (m, 3H), 2.3–2.1 (2m, 1H), 1.9–1.5 (m, 4H), 1.20+1.19 (2 t, J=8 Hz, 3H) Mass spec (ES+) m/z 482.4 (M+H$^+$).

Example 14

Preparation of (S)-1-[3-ethyl-5-(1-methyl-1H-tetrazol-5-yl)-phenyl]3-{1-[2-(fluorophenyl)-ethyl]-piperidin-3-ylmethyl}-urea A solution of (S)-1-[3-ethyl-5-(1-methyl-1H-tetrazol-5-yl)-phenyl]-3-piperidin-3-ylmethyl-urea hydrochloride (40 mg, 105 μmol) in acetonitrile (1 mL) was treated with phenethyl bromide (15 μL, 105 μmol) and potassium carbonate (22 mg, 158 μmol) and stirred at reflux for 17 hours. The mixture was concentrated under vacuum and the residue was purified by flash chromatography, eluting with 2.5% methanol in dichloromethane containing 0.25% aqueous ammonia, to provide a tan glassy solid (30 mg, 64%). $^1$H NMR (300 MHz, CDCl$_3$) δ8.19 (s, 1H), 7.69 (s, 1H), 7.57 (s, 1H), 7.26 (m, 2H), 7.18 (m, 3H), 7.06 (s, 1H), 6.07 (bm, 1H), 4.12 (s, 3H), 3.23 (m, 2H), 3.00 (m, 1H), 2.88 (m, 1H), 2.78 (m, 2H), 2.60 (m, 4H), 2.33 (m, 2H), 2.08 (m, 1H), 2.0–1.5 (m, 5H), 1.19 (t, J=8 Hz, 3H) Mass spec (ES+) m/z 448.4 (M+H$^+$). [α]D$^{25}$ =+17.5° (c=0.194, ethanol).

Example 15

Part A: Preparation of trans 2-pentenoic acid [2-(4-fluorophenyl)ethyl]amide

A solution of trans-2-pentenoic acid (7.62 g, 76.2 mmol) in tetrahydrofuran (350 mL) was stirred at –15° C. and treated with N-methylmorpholine (8.37 mL, 76.2 mmol). After 10 minutes, isobutyl chloroformate (9.87 mL, 76.2 mmol) was added. After 10 minutes, a precipitate had formed. A solution of 2-(4-fluorophenyl)ethylamine (10.6 g, 76.2 mmol) in tetrahydrofuran (50 mL) was added slowly, and the mixture was stirred at room temperature, and the residue was dissolved in ethyl acetate. The then with saturated aqueous sodium bicarbonate, then was dried over sodium sulfate and concentrated. The residue was recrystallized from ethyl acetate/hexane to provide white crystals (11.69 g, 69%). $^1$H NMR (300 MHz, CDCl$_3$) δ7.17 (m, 2H), 7.01 (t, J=9 Hz, 2H), 6.88 (dt, J=15, 7 Hz, 1H), 5.72 (dt, J=15, 2 Hz, 1H), 5.61 (bs, 1H), 3.56 (m, 2H), 2.83 (t, J=7 Hz, 2H), 2.20 (m, 2H), 1.05 (t, J=7 Hz, 3H). Mass spec (ES+) m/z 221.9 (M+H$^+$, 100%).

Part B: Preparation of 1-[2-(4-fluorophenyl)ethyl]-4-ethyl-2,6-dioxopiperidine-3-carbonitrile A solution of trans 2-pentenoic acid [2-(4-fluorophenyl)ethyl]amide (2.0 g, 9.05 mmol) and ethyl cyanoacetate (1.93 mL, 18.1 mmol) in tert-butanol (30 mL) was treated with a solution of potassium tert-butoxide in tetrahydrofuran (1.0 M, 18.1 mL, 18.1 mmol) and heated at 80° C. After 18 hours, the solution was cooled to room temperature and treated with 1.0 N aqueous hydrochloric acid. The mixture was concentrated under vacuum and the residue was recrystallized from ethanol to provide a pale pink solid (2.0 g, 77%). $^1$H NMR (300 MHz, CDCl$_3$) δ7.19 (m, 2H), 7.00 (t, J=9 Hz, 2H), 4.01 (m, 2H), 3.50 (d, J=11 Hz, 1H), 2.97 (dd, J=17, 3 Hz, 1H), 2.83 (t, J=8 Hz, 2H), 2.4–2.2 (m, 1H), 1.88 (m, 1H), 1.44 (m, 1H), 1.02 (t, J=7 Hz, 3H). Mass spec (ES–) m/z 287.2 (M+H$^+$, 100%).

Part C: Preparation of trans-1-[2-(4-fluorophenyl)-ethyl]-4-ethylpiperidin-3-ylmethylamine 1-[2-(4-Fluorophenyl)ethyl]-4-ethyl-2,6-dioxopiperidine-3-carbonitrile (1.0 g, 3.47 mmol) was treated with 1.0 M borane in tetrahydrofuran (69.4 mL, 69.4 mmol) and stirred at room temperature for 65 hours. The solution was cooled on an ice bath and treated very slowly with 2.0 N hydrochloric acid. The mixture was concentrated under vacuum to remove the tetrahydrofuran, and the aqueous residue was heated at reflux for 60 minutes. The mixture was cooled to room temperature and treated with 50% aqueous sodium hydroxide to adjust the pH to about 11. The mixture was extracted with ethyl acetate, and the organic extracts were dried over sodium sulfate and concentrated. The residue was purified by flash chromatography, eluting with 5% methanol in dichloromethane containing 0.5% aqueous ammonia, to provide an oil (340 mg, 37%). $^1$H NMR (300 MHz, CDCl$_3$) δ7.16 (m, 2H), 6.97 (t, J=9 Hz, 2H), 3.13 (m, 1H), 3.00 (m, 1H), 2.92 (dd, J=13, 3 Hz, 1H), 2.83 (m, 2H), 2.58 (m, 2H), 1.99 (td, J=12, 3 Hz, 1H), 1.9–1.0 (m, 8H), 0.90 (t, J=7 Hz, 3H). Mass spec (ES+) m/z 265.4 (M+H$^+$, 100%).

Part D. Preparation of 1-[3-ethyl-5-(1-methyl-1H-tetrazol-5-yl)phenyl]-3-{1-[2-(4-fluorophenyl)-ethyl]-4-ethylpiperidin-3-ylmethyl}-urea A solution of 1-[2-(4-fluorophenyl)ethyl]-4-ethyl-piperidin-3-ylmethylamine (52 mg, 199 μmol) and [3-ethyl-5-(1-methyl-1H-tetrazol-5-yl)phenyl]-carbamic acid phenyl ester (50 mg, 199 μmol) in N,N-dimethylformamide (1.0 mL) was treated with triethylamine (55 μL, 398 μmol). After 18 hours, the mixture was concentrated under vacuum. The residue was purified by flash chromatography, eluting with 5% methanol in dichloromethane containing 0.5% aqueous ammonium hydroxide, provided an amorphous solid (50 mg, 51%). $^1$H NMR (300 MHz, CDCl$_3$) δ8.37 (s, 1H), 7.74 (s, 1H), 7.56 (s, 1H), 7.11 (m, 2H), 7.03 (s, 1H), 6.92 (t, J=9 Hz, 2H), 6.11 (m, 1H), 4.12 (s, 3H), 3.53 (m, 1H), 3.18 (m, 2H), 3.00 (m, 1H), 2.80 (m, 2H), 2.63 (m, 4H), 2.2–2.0 (m, 2H), 1.82 (m, 1H), 1.66 (m, 2H), 1.40 (m, 1H), 1.3–1.1 (m, 2H), 1.20 (t, J=7 Hz, 3H), 0.88 (t, J=7 Hz, 3H). Mass spec (ES+) m/z 494.4 (M+H$^+$, 100%).

Example 16

Part A: Preparation of 2-cyano-N-[2-(4-fluorophenyl)-ethyl]-acetamide

A mixture of 4-fluorophenethylamine (10.6 g, 76.2 mmol) and ethyl cyanoacetate (8.09 mL, 76.2 mmol) was heated in an open flask at 100° C. for 18 hours. The mixture was cooled and the resulting solid was triturated with ethanol, filtered and dried. Recrystallization from ethanol provided off-white crystals (8.2 g, 52%). $^1$H NMR (300 MHz, CDCl$_3$) δ7.17 (m, 2H), 7.03 (t, J=9 Hz, 2H), 6.26 (bs, 1H), 3.54 (q, J=7 Hz, 2H), 3.35 (s, 2H), 2.84 (t, J=7 Hz, 2H). Mass spec (ES–) m/z 205.2 (M–H$^-$, 100%).

Part B: Preparation of 1-[2-(4-fluorophenyl)-ethyl]-4,4-dimethyl-2,6-dioxopiperidine-3-carbonitrile A mixture of 2-cyano-N-[2-(4-fluorophenyl)-ethyl]-acetamide (2.0 g, 19.4 mmol), ethyl 3-methylbut-2-enoate with a solution of potassium tert-butoxide in 80° C. After 16 hours, the mixture was cooled to room temperature and acidified with 1.0 N aqueous hydrochloric acid. The mixture was concentrated under vacuum to provide a brown solid. Recrystallization from 95% ethanol provided a tan solid (2.37 g, 85%). $^1$H NMR (300 MHz, dmso-d$_6$) δ7.24 (m, 2H), 7.11 (t, J=9 Hz, 2H), 4.70 (s, 2H), 3.88 (m, 2H), 2.8–2.6 (m, 4H), 1.16 (s, 3H), 0.98 (s, 3H). Mass spec (ES–) m/z 287.2 (M–H$^-$, 100%).

Part C: Preparation of 1-[2-(4-fluorophenyl)-ethyl]-4,4-dimethylpiperidin-3-ylmethylamine 1-[2-(4-Fluorophenyl)-ethyl]-4,4-dimethyl-2,6-dioxopiperidine-3-carbonitrile (1.0 g, 3.47 mmol) was treated with 1.0 M borane in tetrahydrofuran (69.4 mL, 69.4 mmol) and stirred at room temperature for 18 hours. The solution was cooled on an ice bath and treated very slowly with 2.0 N hydrochloric acid. The mixture was concentrated under vacuum to remove the tetrahydrofuran, and the aqueous residue was heated at reflux for 60 minutes. The mixture was cooled to room temperature and treated with 50% aqueous sodium hydroxide to adjust the pH to about 11. The mixture was extracted with ethyl acetate, and the organic extracts were dried over sodium sulfate and concentrated. The residue was purified by flash chromatography, eluting with 10% methanol in dichloromethane, to provide an oil (300 mg, 33%). $^1$H NMR (300 MHz, CDCl$_3$) δ7.15 (m, 2H), 6.96 (t, J=9 Hz, 2H), 3.66 (m, 1H), 3.11 (m, 2H), 2.97 (m, 1H), 2.9–2.7 (m, 3H), 2.60 (m, 2H), 2.39 (m, 1H), 2.24 (m, 1H), 2.00 (m, 1H), 1.7–1.3 (3H), 1.00 (s, 3H), 0.80 (s, 3H).

Part D. Preparation of 1-[3-ethyl-5-(1-methyl-1H-tetrazol-5-yl)phenyl]-3-{1-[2-(4-fluorophenyl)-ethyl]-4,4-dimethylpiperidin-3-ylmethyl}-urea A solution of 1-[2-(4-fluorophenyl)ethyl]-4,4-dimethyl-piperidin-3-ylmethylamine (53 mg, 199 µmol) and [3-ethyl-5-(1-methyl-1H-tetrazol-5-yl)phenyl]-carbamic acid phenyl ester (50 mg, 199 µmol) in N,N-dimethylformamide (1.0 mL) was treated with triethylamine (55 µL, 398 µmol). After 18 hours, the mixture was concentrated under vacuum. The residue was purified by flash chromatography, eluting with 5% methanol in dichloromethane containing 0.5% aqueous ammonium hydroxide, providing an amorphous solid (50 mg, 50%). $^1$H NMR (300 MHz, CDCl$_3$) δ8.45 (s, 1H), 7.66 (s, 1H), 7.62 (s, 1H), 7.09 (m, 2H), 7.07 (s, 1H), 6.91 (t, J=9 Hz, 2H), 6.23 (m, 1H), 4.13 (s, 3H), 3.38 (m, 1H), 3.10 (m, 2H), 2.85 (m, 3H), 2.74 (m, 2H), 2.62 (q, J=7 Hz, 2H), 2.45 (m, 1H), 2.32 (m, 1H), 1.8–1.6 (m, 2H), 1.46 (m, 1H), 1.21 (t, J=7 Hz, 3H), 1.02 (s, 3H), 0.88 (s, 3H). Mass spec (ES+) m/z 494.3 (M+H$^+$, 100%).

The following examples have been prepared using the process described above in the Examples.

TABLE 1

| Ex. | R$^5$ | R$^6$ | X | C$_3$ stereo-chemistry | R$^7$ | R$^3$ | mass spec (ES+) |
|---|---|---|---|---|---|---|---|
| 1 | 4-F—Ph—CH$_2$C(Me)$_2$CH$_2$— | H | CH$_2$ | RS | H | 3-(1-methyl-1H-tetrazol-5-yl)-phenyl | 480.5 |
| 2 | 4-F—Ph—CH$_2$CH$_2$CH$_2$— | H | CH$_2$ | RS | H | 3-(1-methyl-1H-tetrazol-5-yl)-phenyl | 452.4 |
| 3 | 4-CF$_3$Ph—CH$_2$CH$_2$— | H | CH$_2$ | RS | H | 3-(1-methyl-1H-tetrazol-5-yl)-phenyl | 488.5 |
| 4 | 4-F—Ph—CH$_2$CH$_2$— | H | CH$_2$ | RS | H | 5-acetyl-4-methyl-thiazol-2-yl | 419.2 |
| 5 | 4-F—Ph—CH$_2$CH$_2$— | H | CH(Me) (trans) | RS | H | 3-ethyl-5-(1-methyl-1H-tetrazol-5-yl)-phenyl | 480.4 |
| 6 | 4-F—Ph—CH$_2$CH$_2$— | H | CH(Me) (cis) | RS | H | 3-(1-methyl-1H-tetrazol-5-yl)-phenyl | 480.4 |
| 7 | 4-F—Ph—CH$_2$CH$_2$— | H | CH(N(Me)CH$_2$Ph) (trans) | RS | H | 3-ethyl-5-(1-methyl-1H—tetrazol-5-yl)-phenyl | 585.6 |
| 8 | 4-F—Ph—CH$_2$CH$_2$— | H | CH(NH(Me)) (trans) | RS | H | 3-ethyl-5-(1-methyl-1H—tetrazol-5-yl)-phenyl | 495.2 |
| 9 | 4-F—Ph—CH$_2$CH$_2$— | H | CH(N(Me)Ac) (trans) | RS | H | 3-ethyl-5-(1-methyl-1H—tetrazol-5-yl)-phenyl | 537.4 |
| 10 | 4-F—Ph—CH$_2$CH$_2$— | H | CH(N(Me)Ms) (trans) | RS | H | 3-ethyl-5-(1-methyl-1H—tetrazol-5-yl)-phenyl | 573.4 |
| 11 | 4-H—Ph—C(=O)CH$_2$— | H | CH$_2$ | S | H | 3-ethyl-5-(1-methyl-1H—tetrazol-5-yl)-phenyl | 480.4 |
| 12 | 4-H—Ph—C(=NOH)CH$_2$— | H | CH$_2$ | S | H | 3-ethyl-5-(1-methyl-1H—tetrazol-5-yl)-phenyl | 495.4 |
| 13 | 4-F—Ph—(OH)CH$_2$— | H | CH$_2$ | S | H | 3-ethyl-5-(1-methyl-1H—tetrazol-5-yl)-phenyl | 482.4 |
| 14 | 4-F—Ph—CH$_2$CH$_2$— | H | CH$_2$ | S | H | 3-ethyl-5-(1-methyl-1H—tetrazol-5-yl)-phenyl | 448.4 |
| 15 | 4-F—Ph—CH$_2$CH$_2$— | H | CH(Et) (trans) | S | H | 3-ethyl-5-(1-methyl-1H—tetrazol-5-yl)-phenyl | 494.4 |
| 16 | 4-F—Ph—CH$_2$CH$_2$— | H | C(Me)$_2$ | RS | H | 3-ethyl-5-(1-methyl-1H—tetrazol-5-yl)-phenyl | 494.3 |
| 17 | 4-F—Ph—CH$_2$CH$_2$— | H | CH$_2$ | RS | H | 3-(1-methyl-1H-tetrazol-5-yl-phenyl | 438.4 |
| 18 | 4-F—Ph—CH$_2$CH$_2$— | H | CH$_2$ | R | H | 3-(1-methyl-1H-tetrazol-5-yl-phenyl | 438.4 |
| 19 | 4-F—Ph—CH$_2$CH$_2$— | H | CH$_2$ | S | H | 3-(1-methyl-1H-tetrazol-5-yl-phenyl | 438.4 |
| 20 | 4-F—Ph—CH$_2$CH$_2$CH$_2$— | H | CH$_2$ | R | H | 3-(1-methyl-1H-tetrazol-5-yl-phenyl | 452.4 |
| 21 | 4-F—Ph—CH$_2$CH$_2$CH$_2$— | H | CH$_2$ | S | H | 3-(1-methyl-1H-tetrazol-5-yl-phenyl | 452.4 |
| 22 | 4-F—Ph—CH$_2$CH$_2$— | H | CH$_2$ | RS | H | 3-acetyl-5-(1-methyl-1H-tetrazol-5-yl)-phenyl | 480.4 |
| 23 | 4-F—Ph—CH$_2$CH$_2$— | H | CH$_2$ | RS | H | 4-methylthiazol-2-yl | 377.2 |
| 24 | 4-F—Ph—CH$_2$CH$_2$— | H | CH$_2$ | RS | H | indazol-5-yl | 396.3 |
| 25 | 4-F—Ph—CH$_2$CH$_2$— | H | CH$_2$ | RS | H | 3-ethyl-5-(1-methyl-1H-tetrazol-5-yl)-phenyl) | 466.4 |

TABLE 1-continued

[Structure: R5-N(piperidine/morpholine ring with position 3)-CH(R7)-NH-C(=O)-NH-R3, with R6 on ring and X in ring]

| Ex. | R⁵ | R⁶ | X | C₃ stereo-chemistry | R⁷ | R³ | mass spec (ES+) |
|---|---|---|---|---|---|---|---|
| 26 | 4-F—Ph—CH(OH)CH₂— | H | CH₂ | S | H | 3-(1-methyl-1H-tetrazol-5-yl)-phenyl | 454.3 |
| 27 | 3-Cl—Ph—CH₂CH₂— | H | CH₂ | RS | H | 3-(1-methyl-1H-tetrazol-5-yl)-phenyl | 454.4 |
| 28 | Ph—CH₂CH₂— | H | CH₂ | RS | H | 3-(1-methyl-1H-tetrazol-5-yl)-phenyl | 420.3 |
| 29 | 3-F—Ph—CH₂CH₂— | H | CH₂ | RS | H | 3-(1-methyl-1H-tetrazol-5-yl)-phenyl | 438.4 |
| 30 | 4-Cl—Ph—CH₂CH₂— | H | CH₂ | S | H | 3-(1-methyl-1H-tetrazol-5-yl)-phenyl | 454.3 |
| 31 | 4-F—Ph—CH₂CH(Me)— | H | CH₂ | S | H | 3-(1-methyl-1H-tetrazol-5-yl)-phenyl | 452.3 |
| 32 | 4-F—Ph—CH₂CH₂— | H | CH(Me) (trans) | RS | H | 3-(1-methyl-1H-tetrazol-5-yl)-phenyl | 452.1 |
| 33 | 4-F—Ph—CH₂CH₂— | H | CH(Me) (trans) | RS | H | 3-acetyl-5-(1-methyl-1H-tetrazol-5-yl)-phenyl | 494.4 |
| 34 | 3,4-F₂—Ph—CH₂CH₂— | H | CH₂ | RS | H | 3-(1-methyl-1H-tetrazol-5-yl)-phenyl | 456.4 |
| 35 | 4-F—Ph—CH(Me)CH₂— | H | CH₂ | RS | H | 3-(1-methyl-1H-tetrazol-5-yl)-phenyl | 452.3 |
| 36 | 4-F—Ph—CH₂CH₂CH₂CH₂— | H | CH₂ | RS | H | 3-(1-methyl-1H-tetrazol-5-yl)-phenyl | 466.5 |
| 37 | 4-F—Ph—CH₂CH₂— | H | CH(Ph) (trans) | RS | H | 3-ethyl-5-(1-methyl-1H-tetrazol-5-yl-phenyl | 542.2 |
| 38 | 4-F—Ph—CH₂CH₂— | H | CH(Me) (trans) | R | H | 3-ethyl-5-(1-methyl-1H-tetrazol-5-yl-phenyl | 480.4 |
| 39 | 4-F—Ph—CH₂CH₂— | H | CH(Me) (trans) | S | H | 3-ethyl-5-(1-methyl-1H-tetrazol-5-yl-phenyl | 480.4 |
| 40 | Ph—CH₂CH₂— | H | CH₂ | S | H | 3-ethyl-5-(1-methyl-1H-tetrazol-5-yl-phenyl | 448.4 |
| 41 | 4-F—Ph—CH₂CH₂— | H | CH(iPr) (trans) | RS | H | 3-ethyl-5-(1-methyl-1H-tetrazol-5-yl-phenyl | 508.5 |
| 42 | 4-F—Ph—CH₂CH₂— | H | CH(3-pyridyl) (cis/trans) | RS | H | 3-ethyl-5-(1-methyl-1H-tetrazol-5-yl-phenyl | 534.3 |
| 43 | 4-F—Ph—CH₂CH₂CH₂CH₂— | H | CH₂ | S | H | 3-ethyl-5-(1-methyl-1H-tetrazol-5-yl-phenyl | 494.3 |
| 44 | 4-CF₃—Ph—CH₂CH₂— | H | CH₂ | S | H | 3-ethyl-5-(1-methyl-1H-tetrazol-5-yl-phenyl | 519.4 |
| 45 | 4-Cl—Ph—CH₂CH₂— | H | CH₂ | S | H | 3-ethyl-5-(1-methyl-1H-tetrazol-5-yl)-phenyl | 482.4, 484.4 |
| 46 | 4-F—Ph—CH₂CH₂CH₂— | H | CH₂ | S | H | 3-ethyl-5-(1-methyl-1H-tetrazol-5-yl)-phenyl | 480.4 |
| 47 | 3-Cl—Ph—CH₂CH₂— | H | CH₂ | S | H | 3-ethyl-5-(1-methyl-1H-tetrazol-5-yl)-phenyl | 482.3, 484.3 |
| 48 | 2,4-Cl₂—Ph—CH₂CH₂— | H | CH₂ | S | H | 3-ethyl-5-(1-methyl-1H-tetrazol-5-yl)-phenyl | 516.3, 518.2 |
| 49 | 3-F—Ph—CH₂CH₂— | H | CH₂ | S | H | 3-ethyl-5-(1-methyl-1H-tetrazol-5-yl)-phenyl | 466.3 |
| 50 | 3-F—Ph—CH₂CH₂— | H | CH₂ | S | H | 3-ethyl-5-(1-methyl-1H-tetrazol-5-yl)-phenyl | 466.3 |
| 51 | 4-Me—Ph—CH₂CH₂— | H | CH₂ | S | H | 3-ethyl-5-(1-methyl-1H-tetrazol-5-yl)-phenyl | 462.4 |
| 52 | 4-Br—Ph—CH₂CH₂— | H | CH₂ | S | H | 3-ethyl-5-(1-methyl-1H-tetrazol-5-yl)-phenyl | 528.4 |
| 53 | 4-MeO—Ph—CH₂CH₂ | H | CH₂ | S | H | 3-ethyl-5-(1-methyl-1H—tetrazol-5-yl)-phenyl | 478.4 |
| 54 | 4-N(Me)₂—Ph—CH₂CH₂ | H | CH₂ | S | H | 3-ethyl-5-(1-methyl-1H—tetrazol-5-yl)-phenyl | 491.4 |
| 55 | 3,4-F₂—Ph—CH₂CH₂— | H | CH₂ | S | H | 3-ethyl-5-(1-methyl-1H—tetrazol-5-yl)-phenyl | 488.4 |
| 56 | 2,4-F₂—Ph—CH₂CH₂— | H | CH₂ | S | H | 3-ethyl-5-(1-methyl-1H—tetrazol-5-yl)-phenyl | 484.4 |
| 57 | 4-F—Ph—CH₂CH₂CH₂CH₂— | H | CH₂ | S | H | 3-(1-methyl-1H-tetrazol-5-yl)-phenyl | 494.4 |
| 58 | 4-F—Ph—CH₂CH₂CH₂— | H | CH₂ | S | H | 3-ethyl-5-(1-methyl-1H—tetrazol-5-yl)-phenyl | 480.3 |

TABLE 1-continued

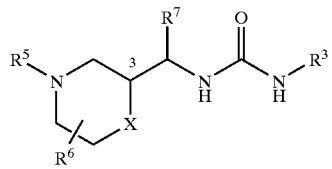

| Ex. | R⁵ | R⁶ | X | C₃ stereo-chemistry | R⁷ | R³ | mass spec (ES+) |
|---|---|---|---|---|---|---|---|
| 59 | 4-F—Ph—CH₂CH₂— | H | CH₂ | S | H | 3-ethyl-5-(1-methyl-1H—tetrazol-5-yl)-phenyl | 466.1 |
| 60 | 4-Cl—Ph—CH₂CH₂— | H | CH₂ | S | H | 3-ethyl-5-(1-methyl-1H—tetrazol-5-yl)-phenyl | 482.3, 484.3 |
| 61 | 3-Cl—Ph—CH₂CH₂— | H | CH₂ | R | H | 3-ethyl-5-(1-methyl-1H—tetrazol-5-yl)-phenyl | 482.3, 484.3 |
| 62 | 3-F—Ph—CH₂CH₂— | H | CH₂ | R | H | 3-ethyl-5-(1-methyl-1H—tetrazol-5-yl)-phenyl | 466.3 |

The following contains representative examples of the present invention, and may be prepared by procedures described above, or methods familiar to one skilled in the art. Each entry in each of the tables (X, R³ and R⁵) is intended to be paired together and with the core structure shown. For example, no. 100 of R³ may be paired with no. 10 of R⁵ and no. 10 of X in the core structure.

TABLE 2*

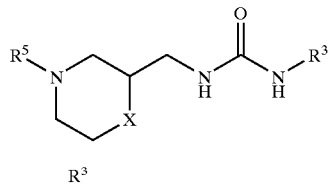

R³

| 1. | 3-CN—Ph |
| 2. | 3-COCH3—Ph |
| 3. | 3-CO2Me—Ph |
| 4. | 3-CO2Et—Ph |
| 5. | 3-CO2H—Ph |
| 6. | 3-CONH2—Ph |
| 7. | 3-CONHMe—Ph |
| 8. | 3-F—Ph |
| 9. | 3-Cl—Ph |
| 10. | 3-Br—Ph |
| 11. | 3-NO2—Ph |
| 12. | 3-NH2—Ph |
| 13. | 3-NHMe—Ph |
| 14. | 3-NMe2—Ph |
| 15. | 3-NHCOCH3—Ph |
| 16. | 3-SO2NH2—Ph |
| 17. | 3-SO2NHMe—Ph |
| 18. | 3-CF3—Ph |
| 19. | 3-OCH3—Ph |
| 20. | 3-OPh—Ph |
| 21. | 3-OCF3—Ph |
| 22. | 3-SCH3—Ph |
| 23. | 3-SOCH3—Ph |
| 24. | 3-SO2CH3—Ph |
| 25. | 3-OH—Ph |
| 26. | 3-CH2OH—Ph |
| 27. | 3-CHOHCH3—Ph |
| 28. | 3-COH(CH3)2—Ph |
| 29. | 3-CHOHPh—Ph |
| 30. | 3-CH3—Ph |
| 31. | 3-C2H5—Ph |
| 32. | 3-iPr—Ph |
| 33. | 3-tBu—Ph |

TABLE 2*-continued

| 34. | 3-Ph—Ph |
| 35. | 3-CH2Ph—Ph |
| 36. | 3-CH2CO2Me—Ph |
| 37. | 3-(1-piperidinyl)-Ph |
| 38. | 3-(1-pyrrolidinyl)-Ph |
| 39. | 3-(2-imidazolyl)-Ph |
| 40. | 3-(1-imidazolyl)-Ph |
| 41. | 3-(2-thiazolyl)-Ph |
| 42. | 3-(3-pyrazolyl)-Ph |
| 43. | 3-(1-pyrazolyl)-Ph |
| 44. | 3-(1-tetrazolyl)-Ph |
| 45. | 3-(5-tetrazolyl)-Ph |
| 46. | 3-(2-pyridyl)-Ph |
| 47. | 3-(2-thienyl)-Ph |
| 48. | 3-(2-furanyl)-Ph |
| 49. | 4-CN—Ph |
| 50. | 4-COCH3—Ph |
| 51. | 4-CO2Me—Ph |
| 52. | 4-CO2Et—Ph |
| 53. | 4-CO2H—Ph |
| 54. | 4-CONH2—Ph |
| 55. | 4-CONHMe—Ph |
| 56. | 4-CONHPh—Ph |
| 57. | 4-NHCONH2—Ph |
| 58. | 4-F—Ph |
| 59. | 4-Cl—Ph |
| 60. | 4-Br—Ph |
| 61. | 4-NO2—Ph |
| 62. | 4-NH2—Ph |
| 63. | 4-NHMe—Ph |
| 64. | 4-NMe2—Ph |
| 65. | 4-NHCOCH3—Ph |
| 66. | 4-SO2NH2—Ph |
| 67. | 4-SO2NHMe—Ph |
| 68. | 4-CF3—Ph |
| 69. | 4-OCH3—Ph |
| 70. | 4-OPh—Ph |
| 71. | 4-OCF3—Ph |
| 72. | 4-SCH3—Ph |
| 73. | 4-SOCH3—Ph |
| 74. | 4-SO2CH3—Ph |
| 75. | 4-OH—Ph |
| 76. | 4-CH2OH—Ph |
| 77. | 4-CHOHCH3—Ph |
| 78. | 4-COH(CH3)2—Ph |
| 79. | 4-CH3—Ph |
| 80. | 4-C2H5—Ph |
| 81. | 4-iPr—Ph |
| 82. | 4-tBu—Ph |
| 83. | 4-Ph—Ph |
| 84. | 4-CH2Ph—Ph |

TABLE 2*-continued

| | |
|---|---|
| 85. | 4-CH2CO2Me—Ph |
| 86. | 4-(1-piperidinyl)-Ph |
| 87. | 4-(1-pyrrolidinyl)-Ph |
| 88. | 4-(2-imidazolyl)-Ph |
| 89. | 4-(1-imidazolyl)-Ph |
| 90. | 4-(2-thiazolyl)-Ph |
| 91. | 4-(3-pyrazolyl)-Ph |
| 92. | 4-(1-pyrazolyl)-Ph |
| 93. | 4-(1-tetrazolyl)-Ph |
| 94. | 4-(5-tetrazolyl)-Ph |
| 95. | 4-(2-pyridyl)-Ph |
| 96. | 4-(2-thienyl)-Ph |
| 97. | 4-(2-furanyl)-Ph |
| 98. | 2-CN—Ph |
| 99. | 2-COCH3—Ph |
| 100. | 2-CO2Me—Ph |
| 101. | 2-CO2Et—Ph |
| 102. | 2-CO2H—Ph |
| 103. | 2-CONH2—Ph |
| 104. | 2-CONHMe—Ph |
| 105. | 2-F—Ph |
| 106. | 2-Cl—Ph |
| 107. | 2-Br—Ph |
| 108. | 2-NO2—Ph |
| 109. | 2-NH2—Ph |
| 110. | 2-NHMe—Ph |
| 111. | 2-NMe2—Ph |
| 112. | 2-NHCOCH3—Ph |
| 113. | 2-SO2NH2—Ph |
| 114. | 2-SO2NHMe—Ph |
| 115. | 2-CF3—Ph |
| 116. | 2-OCH3—Ph |
| 117. | 2-OPh—Ph |
| 118. | 2-OCF3—Ph |
| 119. | 2-SCH3—Ph |
| 120. | 2-SOCH3—Ph |
| 121. | 2-SO2CH3—Ph |
| 122. | 2-OH—Ph |
| 123. | 2-CH2OH—Ph |
| 124. | 2-CHOHCH3—Ph |
| 125. | 2-COH(CH3)2—Ph |
| 126. | 2-CHOHPh—Ph |
| 127. | 2-CH3—Ph |
| 128. | 2-C2H5—Ph |
| 129. | 2-iPr—Ph |
| 130. | 2-tBu—Ph |
| 131. | 2-Ph—Ph |
| 132. | 2-CH2Ph—Ph |
| 133. | 2-CH2CO2Me—Ph |
| 134. | 2-(1-piperidinyl)-Ph |
| 135. | 2-(1-pyrrolidinyl)-Ph |
| 136. | 2-(2-imidazolyl)-Ph |
| 137. | 2-(1-imidazolyl)-Ph |
| 138. | 2-(2-thiazolyl)-Ph |
| 139. | 2-(3-pyrazolyl)-Ph |
| 140. | 2-(1-pyrazolyl)-Ph |
| 141. | 2-(1-tetrazolyl)-Ph |
| 142. | 2-(5-tetrazolyl)-Ph |
| 143. | 2-(2-pyridyl)-Ph |
| 144. | 2-(2-thienyl)-Ph |
| 145. | 2-(2-furanyl)-Ph |
| 146. | 2,4-diF—Ph |
| 147. | 2,5-diF—Ph |
| 148. | 2,6-diF—Ph |
| 149. | 3,4-diF—Ph |
| 150. | 3,5-diF—Ph |
| 151. | 2,4-diCl—Ph |
| 152. | 2,5-diCl—Ph |
| 153. | 2,6-diCl—Ph |
| 154. | 3,4-diCl—Ph |
| 155. | 3,5-diCl—Ph |
| 156. | 3,4-diCF3—Ph |
| 157. | 3,5-diCF3—Ph |
| 158. | 5-Cl-2-MeO—Ph |
| 159. | 5-Cl-2-Me—Ph |
| 160. | 2-F-5-Me—Ph |
| 161. | 2-F-5-NO2—Ph |
| 162. | 3,4-OCH2O—Ph |
| 163. | 3,4-OCH2CH2O—Ph |
| 164. | 2-MeO-4-Me—Ph |
| 165. | 2-MeO-5-Me—Ph |
| 166. | 1-naphthyl |
| 167. | 2-naphthyl |
| 168. | 2-thienyl |
| 169. | 3-thienyl |
| 170. | 2-furanyl |
| 171. | 3-furanyl |
| 172. | 2-pyridyl |
| 173. | 3-pyridyl |
| 174. | 4-pyridyl |
| 175. | 2-indolyl |
| 176. | 3-indolyl |
| 177. | 5-indolyl |
| 178. | 6-indolyl |
| 179. | 3-indazolyl |
| 180. | 5-indazolyl |
| 181. | 6-indazolyl |
| 182. | 2-imidazolyl |
| 183. | 3-pyrazolyl |
| 184. | 2-thiazolyl |
| 185. | 5-tetrazolyl |
| 186. | 2-benzimidazolyl |
| 187. | 5-benzimidazolyl |
| 188. | 2-benzothiazolyl |
| 189. | 5-benzothiazolyl |
| 190. | 2-benzoxazolyl |
| 191. | 5-benzoxazolyl |
| 192. | 1-adamantyl |
| 193. | 2-adamantyl |
| 194. | 3-(1-methyltetrazol-5-yl)-Ph |
| 195. | 3-(5-methyltetrazol-1-yl)-Ph |
| 196. | 3-(1-ethyltetrazol-5-yl)-Ph |
| 197. | 3-(1-cyclopropylyltetrazol-5-yl)-Ph |
| 198. | 3-(1-(2-methoxyethyl)tetrazol-5-yl)-Ph |
| 199. | 3-(1-(2-cyanoethyl)tetrazol-5-yl)-Ph |
| 200. | 3-(1-methyltetrazol-5-yl)-5-[(CH3)2N—CO]—Ph |
| 201. | 3-(1-methyltetrazol-5-yl)-5-[(CH3)NH—CO]—Ph |
| 202. | 3-(1-methyltetrazol-5-yl)-5-[H2N—CO]—Ph |
| 203. | 3-(1-methyltetrazol-5-yl)-5-[COCH3]—Ph |
| 204. | 3-(1-methyltetrazol-5-yl)-5-[morpholin-1-yl-CO]—Ph |
| 205. | 3-(1-methyltetrazol-5-yl)-5-F—Ph |
| 206. | 3-(1-methyltetrazol-5-yl)-5-Cl—Ph |
| 207. | 3-(1-methyltetrazol-5-yl)-5-Br—Ph |
| 208. | 3-(1-methyltetrazol-5-yl)-4-F—Ph |
| 209. | 3-(1-methyltetrazol-5-yl)-4-Cl—Ph |
| 210. | 3-(1-methyltetrazol-5-yl)-4-Br—Ph |
| 211. | 3-(1-methyltetrazol-5-yl)-5-CF3—Ph |
| 212. | 3-(1-methyltetrazol-5-yl)-4-CF3—Ph |
| 213. | 3-(1-methyltetrazol-5-yl)-2-CH3O—Ph |
| 214. | 3-(1-methyltetrazol-5-yl)-4-CH3O—Ph |
| 215. | 3-(1-methyltetrazol-5-yl)-5-CH3O—Ph |
| 216. | 3-(1-methyltetrazol-5-yl)-6-CH3O—Ph |
| 217. | 3-(1-methyltetrazol-5-yl)-5-CH3—Ph |
| 218. | 3-(1-methyltetrazol-5-yl)-5-CH3CH2—Ph |
| 219. | 4-(1-methyltetrazol-5-yl)-5-[morpholin-1-yl-CO]—Ph |
| 220. | 4-(1-methyltetrazol-5-yl)-5-F—Ph |
| 221. | 4-(1-methyltetrazol-5-yl)-5-Cl—Ph |
| 222. | 4-(1-methyltetrazol-5-yl)-5-Br—Ph |
| 223. | 4-(1-methyltetrazol-5-yl)-3-CF3—Ph |
| 224. | 4-(1-methyltetrazol-5-yl)-2-CH3O—Ph |
| 225. | 4-(1-methyltetrazol-5-yl)-5-CH3O—Ph |
| 226. | 3,5-bis(morpholin-1-yl)-Ph |
| 227. | 3,5-bis(1,2,4-triazol-1-yl)-Ph |
| 228. | 3,5-bis(pyrazol-1-yl)-Ph |
| 229. | 3,5-bis(oxazol-2-yl)-Ph |
| 230. | 3,5-bis(isoxazol-3-yl)-Ph |

TABLE 2*-continued

| | |
|---|---|
| 231. | 3,5-bis(isoxazol-5-yl)-Ph |
| 232. | 3,5-bis(1,2,3-triazol-1-yl)-Ph |
| 233. | 3,5-bis(COCH3)—Ph |
| 234. | 3,5-bis(CH2OH)—Ph |
| 235. | 3-(thiazol-4-yl)-Ph |
| 236. | 3-(thiazol-5-yl)-Ph |
| 237. | 3-(pyrazol-4-yl)-Ph |
| 238. | 3-(1-methyl-3-pyrazolyl)-Ph |
| 239. | 3-(3-isoxazolyl)-Ph |
| 240. | 3-(4-isoxazolyl)-Ph |
| 241. | 3-(5-isoxazolyl)-Ph |
| 242. | 1-methyl-5-pyrazolyl |
| 243. | 1-ethyl-5-pyrazolyl |
| 244. | [1,3,4]-oxadiazol-2-yl |
| 245. | CO—NH-(2-ethylpyrazol-3-yl) |
| 246. | CO—NH-(thiazol-2-yl) |
| 247. | CO—NH-(isoxazol-3-yl) |
| 248. | 5-acetyl-4-methylthiazol-2-yl |
| 249. | 5-acetyl-4-methyloxazol-2-yl |
| 250. | 5-acetyl-4-methylimidazol-2-yl |
| 251. | 3-acetyl-5-[(CH3)2N—CO]—Ph |
| 252. | 3-acetyl-5-[(CH3)NH—CO]—Ph |
| 253. | 3-acetyl-5-[H2N—CO]—Ph |
| 254. | 3-acetyl-5-[morpholin-1-yl-CO]—Ph |
| 255. | 3-acetyl-5-F—Ph |
| 256. | 3-acetyl-5-Cl—Ph |
| 257. | 3-acetyl-5-Br—Ph |
| 258. | 3-acetyl-4-F—Ph |
| 259. | 3-acetyl-4-Cl—Ph |
| 260. | 3-acetyl-4-Br—Ph |
| 261. | 3-acetyl-5-CF3—Ph |
| 262. | 3-acetyl-4-CF3—Ph |
| 263. | 3-acetyl-2-CH3O—Ph |
| 264. | 3-acetyl-4-CH3O—Ph |
| 265. | 3-acetyl-5-CH3O—Ph |
| 266. | 3-acetyl-6-CH3O—Ph |
| 267. | 3-acetyl-5-CH3—Ph |
| 268. | 3-acetyl-5-CH3CH2—Ph |
| 269. | 4-acetyl-5-[morpholin-1-yl-CO]—Ph |
| 270. | 4-acetyl-5-F—Ph |
| 271. | 4-acetyl-5-Cl—Ph |
| 272. | 4-acetyl-5-Br—Ph |
| 273. | 4-acetyl-3-CF3—Ph |
| 274. | 4-acetyl-2-CH3O—Ph |
| 275. | 4-acetyl-5-CH3O—Ph |
| 276. | 3-acetyl-5-(1-methyltetrazol-5-yl)-Ph |
| 277. | 3-acetyl-5-(1-ethyltetrazol-5-yl)-Ph |
| 278. | 3-acetyl-5-(1-cyclopropyltetrazol-5-yl)-Ph |
| 279. | 3-acetyl-5-(oxazol-2-yl)-Ph |
| 280. | 3-acetyl-5-(isoxazol-3-yl)-Ph |
| 281. | 3-acetyl-5-(isoxazol-5-yl)-Ph |
| 282. | 3-acetyl-5-(pyrazol-1-yl)-Ph |
| 283. | 3-acetyl-5-(1,2,4-triazol-1-yl)-Ph |
| 284. | 3-acetyl-5-(CH2OH)—Ph |
| 285. | 3-acetyl-5-(furan-2-yl)-Ph |
| 286. | 3-acetyl-5-(furan-3-yl)-Ph |
| 287. | 3-acetyl-5-(thien-2-yl)-Ph |
| 288. | 3-acetyl-5-(thien-3-yl)-Ph |
| 289. | 3-acetyl-5-CN—Ph |
| 290. | 3-acetyl-5-(CC)—Ph |
| 291. | 3-acetyl-5-(isopropyl)-Ph |
| 292. | 3-acetyl-5-(SO2NH2)—Ph |
| 293. | 3-acetyl-5-(CO-4-morpholane)-Ph |
| 294. | 3-isopropyl-5-(1-methyltetrazol-5-yl)-Ph |
| 295. | 3-SO2NH2-5-(1-methyltetrazol-5-yl)-Ph |
| 296. | 3,5-di(OMe)-Ph |
|  | 3,4,5-tri(Ome)—Ph |

| R⁵ | |
|---|---|
| 1. | 4-F—Ph—CH2C(Me)2CH2— |
| 2. | 4-F—Ph—CH2CH2CH2— |
| 3. | 4-CF3Ph—CH2CH2— |
| 4. | 4-F—Ph—CH2CH2— |
| 5. | 4-F—Ph—CH2CH2— |
| 6. | 4-F—Ph—CH2CH2— |
| 7. | 4-F—Ph—CH2—CH2— |
| 8. | 4-F—Ph—CH2CH2— |
| 9. | 4-F—Ph—CH2CH2— |
| 10. | 4-F—Ph—CH2CH2— |
| 11. | 4-F—Ph—C(=O)CH2— |
| 12. | 4-F—Ph—C(=NOH)CH2— |
| 13. | 4-F—Ph—CH(OH)CH2— |
| 14. | 4-F—Ph—CH2CH2— |
| 15. | 4-F—Ph—CH2CH2— |
| 16. | 4-F—Ph—CH2CH2— |
| 17. | 4-F—Ph—CH2CH2— |
| 18. | 4-F—Ph—CH2CH2— |
| 19. | 4-F—Ph—CH2CH2— |
| 20. | 4-F—Ph—CH2CH2CH2— |
| 21. | 4-F—Ph—CH2CH2CH2— |
| 22. | 4-F—Ph—CH2CH2— |
| 23. | 4-F—Ph—CH2CH2— |
| 24. | 4-F—Ph—CH2CH2— |
| 25. | 4-F—Ph—CH2CH2— |
| 26. | 4-F—Ph—CH(OH)CH2— |
| 27. | 3-Cl—Ph—CH2CH2— |
| 28. | Ph—CH2CH2— |
| 29. | 3-F—Ph—CH2CH2— |
| 30. | 4-Cl—Ph—CH2CH2— |
| 31. | 4-F—Ph—CH2CH(Me)— |
| 32. | 4-F—Ph—CH2CH2— |
| 33. | 4-F—Ph—CH2CH2— |
| 34. | 3,4-F2—Ph—CH2CH2— |
| 35. | 4-F—Ph—CH(Me)CH2— |
| 36. | 4-F—Ph—CH2CH2CH2— |
| 37. | 4-F—Ph—CH2CH2— |
| 38. | 4-F—Ph—CH2CH2— |
| 39. | 4-F—Ph—CH2CH2— |
| 40. | Ph—CH2CH2— |
| 41. | 4-F—Ph—CH2CH2— |
| 42. | 4-F—Ph—CH2CH2— |
| 43. | 4-F—Ph—CH2CH2CH2CH2— |
| 44. | 4-CF3—Ph—CH2CH2— |
| 45. | 4-Cl—Ph—CH2CH2— |
| 46. | 4-F—Ph—CH2CH2CH2— |
| 47. | 3-Cl—Ph—CH2CH2— |
| 48. | 2,4-Cl2—Ph—CH2CH2— |
| 49. | 3-F—Ph—CH2CH2— |
| 50. | 2-F—Ph—CH2CH2— |
| 51. | 4-Me—Ph—CH2CH2— |
| 52. | 4-Br—Ph—CH2CH2— |
| 53. | 4-MeO—Ph—CH2CH2— |
| 54. | 4-N(Me)2—Ph—CH2CH2— |
| 55. | 3,4-F2—Ph—CH2CH2— |
| 56. | 2,4-F2—Ph—CH2CH2— |
| 57. | 4-F—Ph—CH2CH2CH2CH2— |
| 58. | 4-F—Ph—CH2CH2CH2— |
| 59. | 4-F—Ph—CH2CH2— |
| 60. | 4-Cl—Ph—CH2CH2— |
| 61. | 3-Cl—Ph—CH2CH2— |
| 62. | 3-F—Ph—CH2CH2— |
| 63. | |

| X | |
|---|---|
| 1. | CH2 |
| 2. | CH(Me) (trans) |
| 3. | CH(Me) (cis) |
| 4. | CH(N(Me)CH2Ph) (trans) |
| 5. | CH(NH(Me)) (trans) |
| 6. | CH(N(Me)Ac) (trans) |
| 7. | CH(N(Me)Ms) (trans) |
| 8. | CH(Et) (trans) |
| 9. | C(Me)2 |
| 10. | CH(Ph) (trans) |
| 11. | CH2 |
| 12. | CH(iPr) (trans) |
| 13. | CH(3-pyridyl) (cis/trans) |

All stereocenters are included either as a racemate or as R or S configuration.

Utility

The utility of the compounds in accordance with the present invention as modulators of chemokine receptor activity may be demonstrated by methodology known in the art, such as the assays for CCR-2 and CCR-3 ligand binding, as disclosed by Ponath et al., J. Exp. Med., 183, 2437–2448 (1996) and Uguccioni et al., J. Clin. Invest., 100, 1137–1143 (1997). Cell lines for expressing the receptor of interest include those naturally expressing the chemokine receptor, such as EOL-3 or THP-1, those induced to express the chemokine receptor by the addition of chemical or protein agents, such as HL-60 or AML14.3D10 cells treated with, for example, butyric acid with interleukin-5 present, or a cell engineered to express a recombinant chemokine receptor, such as CHO or HEK-293. Finally, blood or tissue cells, for example human peripheral blood eosinophils, isolated using methods as described by Hansel et al., J. Immunol. Methods, 145, 105–110 (1991), can be utilized in such assays.

The utility of the compounds in accordance with the present invention as inhibitors of the migration of eosinophils or cell lines expressing the chemokine receptors may be demonstrated by methodology known in the art, such as the intracellular calcium measurement (disclosed by Bacon et al., Brit. J. Pharmacol., 95, 966–974 (1988)). In particular, the compound of the present invention have activity in inhibition of the migration of eosinophils in the aforementioned assays. As used herein, "activity" is intended to mean a compound demonstrating an IC50 of 10 $\mu$M or lower in concentration when measured in the aforementioned assays. Such a result is indicative of the intrinsic activity of the compounds as modulators of chemokine receptor activity. An intracellular calcium measurement protocol is described below.

Intracellular $Ca^{2+}$ Measurement

Cells ($8 \times 10^5$/mL) were loaded with 4 $\mu$M Fluo-3 AM (Molecular Probes, Eugene. Oreg.) in calcium-free PBS containing 0.1% BSA, 1% FBS, 20 mM HEPES, 5 mM glucose and 2.5 mM probenecid) for 60 minutes at 37° C in the dark. After two washes in buffer (PBS with 0.1% BSA, 20 mM HEPES, 5 mM glucose and 2.5 mM probenecid), cells ($2 \times 10^6$/mL) were resuspended in RPMI containing 0.1% BSA, 20 mM HEPES and 2.5 mM probenecid and plated in 96-well black, clear-bottomed plates (#3603, Corning, Acton, Mass.), previously coated with poly-D-lysine, at $2 \times 10^5$/well. Individual plates were inserted in a FLIPR (Molecular Devices, Sunnyvale, Calif.). Compound or vehicle (50 $\mu$L) was added robotically and incubated for 5 minutes at room temperature, then eotaxin (50 $\mu$L) was added for a final concentration of 10 nM. The eotaxin-dependent increase in fluorescence over baseline was recorded in duplicate wells.

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966–974 (1988). In particular, the compound of the present invention have activity in inhibition of the migration of eosinophils in the aforementioned assays. As used herein, "activity" is intended to mean a compound demonstrating an IC50 of 10 $\mu$M or lower in concentration when measured in the aforementioned assays. Such a result is indicative of the intrinsic activity of the compounds as modulators of chemokine receptor activity. A human eosinophil chemotaxis assay protocol is described below.

Human Eosinophil Chemotaxis Assay

Neuroprobe MBA96 96-well chemotaxis chambers with Neuroprobe polyvinylpyrrolidone-free polycarbonate PFD5 5-micron filters in place are warmed in a 37° C. incubator prior to assay. Freshly isolated human eosinophils, isolated according to a method such as that described by Hansel et al. (1991), are suspended in RPMI 1640 with 0.1% bovine serum albumin at $1 \times 10^6$ cells/ml and warmed in a 37° C. incubator prior to assay. A 20 nM solution of human eotaxin in RPMI 1640 with 0.1% bovine serum albumin is warmed in a 37° C. incubator prior to assay. The eosinophil suspension and the 20 nM eotaxin solution are each mixed 1:1 with prewarmed RPMI 1640 with 0.1% bovine serum albumin with or without a dilution of a test compound that is at two fold the desired final concentration. These mixtures are warmed in a 37° C. incubator prior to assay. The filter is separated from the prewarmed Neuroprobe chemotaxis chamber and the eotaxin/compound mixture is placed into a Polyfiltronics MPC 96 well plate that has been placed in the bottom part of the Neuro Probe chemotaxis chamber. The approximate volume is 370 microliters and there should be a positive meniscus after dispensing. The filter is replaced above the 96 well plate, the rubber gasket is attached to the bottom of the upper chamber, and the chamber assembled. A 200 $\mu$l volume of the cell suspension/compound mixture is added to the appropriate wells of the upper chamber. The upper chamber is covered with a plate sealer, and the assembled unit placed in a 37° C. incubator for 45 minutes. After incubation, the plate sealer is removed and all remaining cell suspension is aspirated off. The chamber is disassembled and, while holding the filter by the sides at a 90-degree angle, unmigrated cells are washed away using a gentle stream of phosphate buffered saline dispensed from a squirt bottle and then the filter wiped with a rubber tipped squeegee. The filter is allowed to completely dry and immersed completely in Wright Giemsa stain for 30–45 seconds. The filter is rinsed with distilled water for 7 minutes, rinsed once with water briefly, and allowed to dry. Migrated cells are enumerated by microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays. As used herein, "activity" is intended to mean a compound demonstrating an IC50 of 10 $\mu$M or lower in concentration when measured in the aforementioned assays. Such a result is also indicative of the intrinsic activity of the compounds as modulators of chemokine receptor activity.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trinchuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., *Anisaki* sp., *Phocanema* sp.), cutaneous larva migraines (*Ancylostona braziliense, Ancylostona caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen , aspirin, codeine, fentaynl, ibuprofen, indomethacin, ketorolac, morphine, naproxen, phenacetin, piroxicam, a steroidal analgesic, sufentanyl, sunlidac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) integrin antagonists such as those for selectines, ICAMs and VLA-4; (b) steroids such as beclomethasone, methylprednisolone, betamethasone, immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102,203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention to the NSAID will generally range from about also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration;

the species, age, sex, health, medical condition, and weight of the recipient; the nature and extent of the symptoms; the kind of concurrent treatment; the renal and hepatic function of the patient,and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical pratices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such ploymers can include polyvinylpyrrolidone, pyran copolymer, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucoe), and related sugar solutins and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or in separate forms but at the same time by the same manner, will be readily apparent to those skilled in the art, once armed with the present disclosure.

As will be apparent to one skilled in the art, numerous modifications and variations of the present invention are possible in light of the above teachings. It is therefore to be understood that within the scope of the appended claims, the invention may be practiced otherwise than as specifically described herein.

What is claimed is:
1. A compound of formula (I):

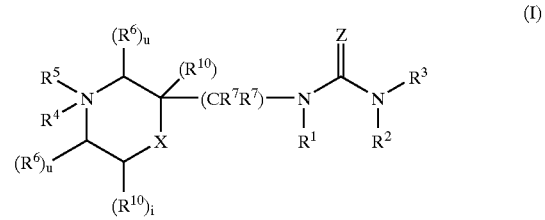

(I)

or stereoisomers or pharmaceutically acceptable salts thereof, wherein:

Z is selected from O, S, N($R^d$), C(CN)$_2$, CH(NO$_2$), and CH(CN);

X is C($R^8$)($R^9$);

$R^1$ and $R^2$ are independently selected from H, $C_{1-8}$ alkyl, $C_{2-8}$ alkenyl, and $C_{2-8}$ alkynyl;

$R^d$ is selected from H, $C_1$–$C_6$ alkyl, $C_3$–$C_6$ cycloalkyl, CON($R^f$)$R^f$, $OR^e$, CN, NO$_2$, and (CH$_2$)$_r$-phenyl substituted with 0–3 $R^{18}$;

$R^e$, at each occurrence, is independently selected from H, $C_{1-6}$ alkyl, $C_{3-6}$ cycloalkyl, and phenyl substituted with 0–3 $R^{18}$;

$R^f$, at each occurrence, is independently selected from H, $C_{1-6}$ alkyl, $C_{3-6}$ cycloaklyl, and phenyl substituted with 0–3 $R^{18}$, or optionally, two $R^f$ may be taken together with the nitrogen to which both are attached to form a pyrrolidine, piperidine, piperazine or morpholine ring;

$R^3$ is selected from a (C$R^{3'}R^{3'}$)$_r$—$C_{3-6}$ carbocyclic residue substituted with 0–5 $R^{15}$;

$R^{3'}$, at each occurrence, is independently selected from H, $C_{1-6}$ alkyl, (CH$_2$)$_r$C$_{3-6}$ cycloalkyl, and phenyl;

$R^4$ is absent, taken with the nitrogen to which it is attached to form an N-oxide, or selected from $C_{1-8}$ alkyl, $C_{2-8}$ alkenyl, $C_{2-8}$ alkynyl, (CH$_2$)$_r$C$_{3-6}$ cycloalkyl, (CH$_2$)$_q$C (O)$R^{4b}$, (CH$_2$)$_q$C(O)NR$^{4a}$R$^{4a}$, (CH$_2$)$_q$C(O)OR$^{4b}$, and a (CH$_2$)$_r$—$C_{3-6}$ carbocyclic residue substituted with 0–3 $R^{4c}$;

$R^{4a}$, at each occurrence, is independently selected from H, $C_{1-6}$ alkyl, (CH$_2$)$_r$C$_{3-6}$ cycloalkyl, and phenyl;

$R^{4b}$, at each occurrence, is independently selected from $C_{1-6}$ alkyl, $C_{2-8}$ alkenyl, (CH$_2$)$_r$C$_{3-6}$ cycloalkyl, $C_{2-8}$ alkynyl, and phenyl;

$R^{4c}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-5}$ alkyl, (CH$_2$)$_r$NR$^{4a}$R$^{4a}$, and (CH$_2$)$_r$phenyl;

$R^5$ is selected from

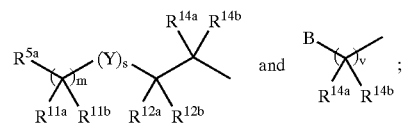

Y is selected from O, N($R^{25}$), S, S(O) and S(O)$_2$;

ring B is a 5–7 membered cycloalkyl ring optionally containing a C=O, and being substituted with 0–2 $R^{11a}$, wherein the cycloalkyl is fused with a benzo group substituted with 0–3 $R^{16}$ or is fused with a 5–6 membered aromatic heterocyclic ring having 0–3 N, 0–1 O, or 0–1 S, the heterocyclic ring being substituted with 0–3 $R^{16}$;

alternatively, ring B is a fused 5–7 membered saturated heterocyclic ring containing 0–1 O, $N(R^{16})$, S, S(O), and $S(O)_2$, substituted with 0–2 $R^{11a}$, the heterocyclic ring being fused with a benzo group substituted with 0–3 $R^{16}$ or is fused with a 5–6 membered heterocyclic ring having 0–3 N, 0–1 O, or 0–1 S, the heterocyclic ring being substituted with 0–3 $R^{16}$;

provided that if ring B is a heterocyclic ring, then the number of carbon atoms separating the heteroatom of ring B and the nitrogen atom of structure (I) bonded to $R^5$ is at least 2;

$R^{5a}$ is selected from a $C_{3-10}$ carbocyclic residue substituted with 0–5 $R^{16}$, and a 5–10 membered heterocyclic residue containing 1–4 heteroatoms selected from N, O, and S, substituted with 0–3 $R^{16}$;

$R^6$, at each occurrence, is independently selected from $C_{1-6}$ alkyl, $C_{2-8}$ alkenyl, $C_{2-8}$ alkynyl, $(CH_2)_rC_{3-6}$ cycloalkyl, $(CF_2)_rCF^3$, CN, $(CH_2)_rNR^{6a}R^{6a}$, $(CH_2)_q$ OH, $(CH_2)_qOR^{6b}$, $(CH_2)_qSH$, $(CH_2)_qSR^{6b}$, $(CH_2)_rC(O)$ OH, $(CH_2)_rC(O)R^{6b}$, $(CH_2)_rC(O)NR^{6a}R^{6a}$, $(CH_2)_q$ $NR^{6d}C(O)R^{6a}$, $(CH_2)_rC(O)OR^{6b}$, $(CH_2)_qOC(O)R^{6b}$, $(CH_2)_rS(O)_pR^{6b}$, $(CH_2)_rS(O)_2NR^{6a}R^{6a}$, $(CH_2)_rNR^{6d}S(O)_2R^{6b}$, and $(CH_2)_r$phenyl substituted with 0–3 $R^{6c}$;

$R^{6a}$, at each occurrence, is independently selected from H, $C_{1-6}$ alkyl, $C_{3-6}$ cycloalkyl, and phenyl substituted with 0–3 $R^{6c}$;

$R_{6b}$, at each occurrence, is independently selected from $C_{1-6}$ alkyl, $C_{3-6}$ cycloalkyl, and phenyl substituted with 0–3 $R^{6c}$;

$R^{6c}$, at each occurrence, is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_r$ $SC_{1-5}$ alkyl, and $(CH_2)_rNR^{6d}R^{6d}$;

$R_{6d}$, at each occurrence, is independently selected from H, $C_{16}$ alkyl, and $C_{3-6}$ cycloalkyl;

$R^7$, at each occurrence, is independently selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{7d}$, $(CH_2)_qSR^{7d}$, $(CH_2)_qNR^{7a}R^{7a}$, $(CH_2)_qC(O)OH$, $(CH_2)_rC(O)R^{7b}$, $(CH_2)_rC(O)$ $NR^{7a}R^{7a}$, $(CH_2)_qNR^{7a}C(O)R^{7a}$, $(CH_2)_qNR^{7a}C(O)H$, $(CH_2)_rC(O)OR^{7b}$, $(CH_2)_qOC(O)R^{7b}$, $(CH_2)_qS(O)_pR^{7b}$, $(CH_2)_qS(O)_2NR^{7a}R^{7a}$, $(CH_2)_qNR^{7a}S(O)_2R^{7b}$, $C_{1-6}$ haloalkyl, a $(CH_2)_r$—$C_{3-6}$ carbocyclic residue substituted with 0–3 $R^{7c}$, and a $(CH_2)_r$-5–10 membered heterocyclic system containing 1–4 heteroatoms selected from N, O, and S, substituted with 0–2 $R^{7c}$;

$R^{7a}$, at each occurrence, is independently selected from H, $C_{1-6}$ alkyl, $C_{2-8}$ alkenyl, $C_{2-8}$ alkynyl, a $(CH_2)_r$—$C_{3-6}$ carbocyclic residue substituted with 0–5 $R^{7e}$, and a $(CH_2)_r$-5–10 membered heterocyclic system containing 1–4 heteroatoms selected from N, O, and S, substituted with 0–3 $R^{7e}$;

$R^{7b}$, at each occurrence, is independently selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{7e}$, and a $(CH_2)_r$-5–6 membered heterocyclic system containing 1–4 heteroatoms selected from N, O, and S, substituted with 0–3 $R^{7e}$;

$R^{7c}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_r$ $NR^{7f}R^{7f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{7b}$, $(CH_2)_rC(O)$ $NR^{7f}R^{7f}$, $(CH_2)_rNR^{7f}C(O)R^{7a}$, $(CH_2)_rC(O)OC_{1-4}$ alkyl, $(CH_2)_rOC(O)R^{7b}$, $(CH_2)_rC(=NR^{7f})NR^{7f}R^{7f}$, $(CH_2)_rS(O)_pR^{7b}$, $(CH_2)_rNHC(=NR^{7f})NR^{7f}R^{7f}$, $(CH_2)_r$ $S(O)_2NR^{7f}R^{7f}$, $(CH_2)_rNR^{7f}S(O)_2R^{7b}$, and $(CH_2)_r$ phenyl substituted with 0–3 $R^{7e}$;

$R^{7d}$, at each occurrence, is independently selected from $C_{1-6}$ alkyl substituted with 0–3 $R^{7e}$, alkenyl, alkynyl, and a $C_{3-6}$ carbocyclic residue substituted with 0–3 $R^{7c}$;

$R^{7e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$ phenyl;

$R^{7f}$, at each occurrence, is independently selected from H, $C_{1-6}$ alkyl, and $C_{3-6}$ cycloalkyl;

$R^8$ is selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN$ $(R^{18a})R^{18b}$, $(CH_2)_rOH$, $(CH_2)_rOR^{19}$, $(CH_2)_rSH$, $(CH_2)_rSR^{19}$, $(CH_2)_rC(O)OH$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_rOC(O)R^{19}$, $(CH_2)_rS(O)R^{19}$, $(CH_2)_rS(O)_2R^{19}$, $(CH_2)_rS(O)_2N(R^{18a})R^{18b}$, $(CH_2)_rN(R^{18c})S(O)_2R^{19}$, a $(C(R^{8a})(R^{8b}))_r$—$C_{3-10}$ carbocyclic residue substituted with 0–5 $R^{17}$, and a $(C(R^{8a})(R^{8b}))_r$-5–10 membered heterocyclic system containing 1–4 heteroatoms selected from N, O, and S, substituted with 0–3 $R^{17}$;

$R^{8a}$ and $R^{8b}$, at each occurrence, are independently selected from H, $C_{1-6}$ alkyl, $(CH_2)_rC_{3-6}$ cycloalkyl, and $(CH_2)_r$phenyl substituted with 0–3 $R^{18}$;

$R^9$ is selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_qN$ $(R^{18a})R^{18b}$, $(CH_2)_qOH$, $(CH_2)_qOR^{19}$, $(CH_2)_qSH$, $(CH_2)_qSR^{19}$, $(CH_2)_qC(O)OH$, $(CH_2)_qC(O)R^{19}$, $(CH_2)_q$ $C(O)N(R^{18a})R^{18b}$, $(CH_2)_qN(R^{18c})C(O)R^{19}$, $(CH_2)_qC(O)OR^{19}$, $(CH_2)_qOC(O)R^{19}$, $(CH_2)_qS(O)R^{19}$, $(CH_2)_qS(O)_2R^{19}$, $(CH_2)_qS(O)_2N(R^{18a})R^{18b}$, $(CH_2)_qN(R^{18c})S(O)_2R^{19}$, a $(C(R^{8a})(R^{8b}))_r$—$C_{3-10}$ carbocyclic residue substituted with 0–5 $R^{17}$, and a $(C(R^{8a})(R^{8b}))_r$-5–10 membered heterocyclic system containing 1–4 heteroatoms selected from N, O, and S, substituted with 0–3 $R^{17}$;

alternatively, $R^8$ and $R^9$ taken together are selected from $=O$, $=S$, $=NR^{9a}$;

$R^{9a}$ is selected from H, $C_{1-6}$ alkyl, $C_{2-8}$ alkenyl, $C_{2-8}$ alkynyl, $(CH_2)_rC_{3-6}$ cycloalkyl, $(CH_2)_rOH$, $(CH_2)_r$ $OC_{1-6}$ alkyl, $(CH_2)_rC(O)R^{19}$, $(CH_2)_rC(O)N(R^{18a})R^{18b}$, $(CH_2)_rC(O)OR^{19}$, $(CH_2)_rS(O)_2R^{19}$, $(CH_2)_rS(O)_2$ $N(R^{18a})R^{18b}$, and $(CH_2)_r$phenyl substituted with 0–3 $R^{17}$;

$R^{9b}$, at each occurrence are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_rC(O)OH$, $(CH_2)_rC(O)R^{19}$, $(CH_2)_rC(O)N(R^{18a})R^{18b}$, $(CH_2)_rN$ $(R^{18c})C(O)R^{19}$, $(CH_2)_rC(O)OR^{19}$, $(CH_2)_rOC(O)R^{19}$, $(CH_2)_rS(O)R^{19}$, $(CH_2)_rS(O)_2R^{19}$, $(CH_2)_rS(O)_2N(R^{18a})R^{18b}$, $(CH_2)_rN(R^{18c})S(O)_2R^{19}$, and $(CH_2)_r$phenyl substituted with 0–3 $R^{17}$;

$R^{10}$, at each occurrence, is independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF^3$, CN, $(CH_2)_rNR^{10a}R^{10a}$, $(CH_2)_r$ OH, $(CH_2)_rOR^{10b}$, $(CH_2)_rSH$, $(CH_2)_rSR^{10b}$, $(CH_2)_rC(O)OH$, $(CH_2)_rC(O)R^{10b}$, $(CH_2)_rC(O)NR^{10a}R^{10a}$, (CH$_2$)$_r$NR$^{10d}$C(O)R$^{10a}$, (CH$_2$)$_r$C(O)OR$^{10b}$, (CH$_2$)$_r$OC(O)R$^{10b}$, (CH$_2$)$_r$S(O)$_p$R$^{10b}$, (CH$_2$)$_r$S(O)$_2$NR$^{10a}$R$^{10a}$, (CH$_2$)$_r$NR$^{10d}$S(O)$_2$R$^{10b}$, and (CH$_2$)$_r$phenyl substituted with 0–3 R$^{10c}$;

R$^{10a}$, at each occurrence, is independently selected from H, C$_{1-6}$ alkyl, C$_{3-6}$ cycloalkyl, and phenyl substituted with 0–3 R$^{10c}$;

R$^{10b}$, at each occurrence, is independently selected from C$_{1-6}$ alkyl, C$_{3-6}$ cycloalkyl, and phenyl substituted with 0–3 R$^{10c}$;

R$^{10c}$, at each occurrence, is independently selected from C$_{1-6}$ alkyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-5}$ alkyl, and (CH$_2$)$_r$NR$^{10d}$R$^{10d}$;

R$^{10d}$, at each occurrence, is independently selected from H, C$_{1-6}$ alkyl, and C$_{3-10}$ cycloalkyl;

R$^{11a}$ and R$^{12a}$, at each occurrence are independently selected from H, C$_{1-6}$ alkyl, C$_{2-8}$ alkenyl, C$_{2-8}$ alkynyl, (CH$_2$)$_r$C$_{3-6}$ cycloalkyl, (CF$_2$)$_r$CF$_3$, (CH$_2$)$_r$N(R$^{18a}$)R$^{18b}$, (CH$_2$)$_r$OH, (CH$_2$)$_r$OR$^{19}$, (CH$_2$)$_r$SH, (CH$_2$)$_r$SR$^{19}$, (CH$_2$)$_r$C(O)OH, (CH$_2$)$_r$C(O)R$^{19}$, (CH$_2$)$_r$C(O)N(R$^{18a}$)R$^{18b}$, (CH$_2$)$_r$N(R$^{18c}$)C(O)R$^{19}$, (CH$_2$)$_r$C(O)OR$^{19}$, (CH$_2$)$_r$OC(O)R$^{19}$, (CH$_2$)$_r$S(O)R$^{19}$, (CH$_2$)$_r$S(O)$_2$R$^{19}$, (CH$_2$)$_r$S(O)$_2$N(R$^{18a}$)R$^{18b}$, (CH$_2$)$_r$N(R$^{18c}$)S(O)$_2$R$^{19}$, and (CH$_2$)$_r$phenyl substituted with 0–3 R$^{18}$;

R$^{11b}$, R$^{12b}$, R$^{14a}$ and R$^{14b}$ at each occurrence are independently selected from H, C$_{1-6}$ alkyl, C$_{2-8}$ alkenyl, C$_{2-8}$ alkynyl, (CH$_2$)$_r$C$_{3-6}$ cycloalkyl, (CF$_2$)$_r$CF$_3$, (CH$_2$)$_q$N(R$^{18a}$)R$^{18b}$, (CH$_2$)$_q$OH, (CH$_2$)$_q$OR$^{19}$, (CH$_2$)$_q$SH, (CH$_2$)$_q$SR$^{19}$, (CH$_2$)$_q$C(O)OH, (CH$_2$)$_r$C(O)R$^{19}$, (CH$_2$)$_r$C(O)N(R$^{18a}$)R$^{18b}$, (CH$_2$)$_q$N(R$^{18c}$)C(O)R$^{19}$, (CH$_2$)$_r$C(O)OR$^{19}$, (CH$_2$)$_r$OC(O)R$^{19}$, (CH$_2$)$_q$S(O)R$^{19}$, (CH$_2$)$_q$S(O)$_2$R$^{19}$, (CH$_2$)$_q$S(O)$_2$N(R$^{18a}$)R$^{18b}$, (CH$_2$)$_q$N(R$^{18c}$)S(O)$_2$R$^{19}$, and (CH$_2$)$_r$phenyl substituted with 0–3 R$^{18}$;

alternatively, R$^{11a}$ and R$^{11b}$ taken together are selected from =O, or =NOH, or alternatively, R$^{12a}$ and R$^{12b}$ taken together are selected from =O, or =NOH;

R$^{15}$, at each occurrence, is independently selected from C$_{1-8}$ alkyl, (CH$_2$)$_r$C$_{3-6}$ cycloalkyl, Cl, Br, I, F, NO$_2$, CN, (CHR')$_r$NR$^{15a}$R$^{15a}$, (CHR')$_r$OH, (CHR')$_r$O(CHR')$_r$ R$^{15d}$, (CHR')$_r$SH, (CHR')$_r$C(O)H, (CHR')$_r$S(CHR')$_r$ R$^{15d}$, (CHR')$_r$C(O)OH, (CHR')$_r$C(O)(CHR')$_r$R$^{15b}$, (CHR')$_r$C(O)NR$^{15a}$R$^{15a}$, (CHR')$_r$NR$^{15f}$C(O)(CHR )$_r$ R$^{15b}$, (CHR')$_r$NR$^{15f}$C(O)NR$^{15f}$R$^{15f}$, (CHR')$_r$C(O)O(CHR')$_r$R$^{15d}$, (CHR')$_r$OC(O)(CHR')$_r$R$^{15b}$, (CHR')$_r$ C(=NR$^{15f}$)NR$^{15a}$R$^{15a}$, (CHR')$_r$NHC(=NR$^{15f}$)NR$^{15f}$R$^{15f}$, (CHR')$_r$S(O)$_p$(CHR')$_r$R$^{15b}$, (CHR')$_r$S(O)$_2$ NR$^{15a}$R$^{15a}$, (CHR')$_r$NR$^{15f}$S(O)$_2$(CHR')$_r$R$^{15b}$, C$_{1-6}$ haloalkyl, C$_{2-8}$ alkenyl substituted with 0–3 R', C$_{2-8}$ alkynyl substituted with 0–3 R', (CHR')$_r$phenyl substituted with 0–3 R$^{15e}$, and a (CH$_2$)$_r$-5–10 membered heterocyclic system containing 1–4 heteroatoms selected from N, O, and S, substituted with 0–2 R$^{15e}$;

R', at each occurrence, is independently selected from H, C$_{1-6}$ alkyl, C$_{2-8}$ alkenyl, C$_{2-8}$ alkynyl, (CH$_2$)$_r$C$_{3-6}$ cycloalkyl, and (CH$_2$)$_r$phenyl substituted with R$^{15e}$;

R$^{15a}$, at each occurrence, are selected from H, C$_{1-6}$ alkyl, C$_{2-8}$ alkenyl, C$_{2-8}$ alkynyl, a (CH$_2$)$_r$—C$_{3-6}$ carbocyclic residue substituted with 0–5 R$^{15e}$, and a (CH$_2$)$_r$-5–10 membered heterocyclic system containing 1–4 heteroatoms selected from N, O, and S, substituted with 0–2 R$^{15e}$;

R$^{15b}$, at each occurrence, is independently selected from C$_{1-6}$ alkyl, C$_{2-8}$ alkenyl, C$_{2-8}$ alkynyl, a (CH$_2$)$_r$—C$_{3-6}$ carbocyclic residue substituted with 0–3 R$^{15e}$, and (CH$_2$)$_r$-5–6 membered heterocyclic system containing 1–4 heteroatoms selected from N, O, and S, substituted with 0–2 R$^{15e}$;

R$^{15d}$, at each occurrence, is independently selected from C$_{2-8}$ alkenyl, C$_{2-8}$ alkynyl, C$_{1-6}$ alkyl substituted with 0–3 R$^{15e}$, a (CH$_2$)$_r$—C$_{3-6}$ carbocyclic residue substituted with 0–3 R$^{15e}$, and a (CH$_2$)$_r$5–6 membered heterocyclic system containing 1–4 heteroatoms selected from N, O, and S, substituted with 0–3 R$^{15e}$;

R$^{15e}$, at each occurrence, is independently selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{15f}$R$^{15f}$, and (CH$_2$)$_r$phenyl;

R$^{15f}$, at each occurrence, is independently selected from H, C$_{1-6}$ alkyl, C$_{3-6}$ cycloalkyl, and phenyl;

R$^{16}$, at each occurrence, is independently selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CHR')$_r$NR$^{16a}$R$^{16a}$, (CHR')$_r$OH, (CHR')$_r$O(CHR')$_r$R$^{16d}$, (CHR')$_r$SH, (CHR')$_r$C(O)H, (CHR')$_r$S(CHR')$_r$R$^{16d}$, (CHR')$_r$C(O)OH, (CHR')$_r$C(O)(CHR')$_r$R$^{16b}$, (CHR')$_r$C(O)NR$^{16a}$R$^{16a}$, (CHR')$_r$NR$^{16f}$C(O)(CHR')$_r$R$^{16b}$, (CHR')$_r$C(O)O(CHR')$_r$R$^{16d}$, (CHR')$_r$OC(O)(CHR')$_r$R$^{16b}$, (CHR')$_r$ C(=NR$^{16f}$)NR$^{16a}$R$^{16a}$, (CHR')$_r$NHC(=NR$^{16f}$)NR$^{16f}$R$^{16f}$, (CHR')$_r$S(O)$_p$(CHR')$_r$R$^{16b}$, (CHR')$_r$S(O)$_2$ NR$^{16a}$R$^{16a}$, (CHR')$_r$NR$^{16f}$S(O)$_2$(CHR')$_r$R$^{16b}$, C$_{1-6}$ haloalkyl, C$_{2-8}$ alkenyl substituted with 0–3 R', C$_{2-8}$ alkynyl substituted with 0–3 R', and (CHR')$_r$phenyl substituted with 0–3 R$^{16e}$;

R$^{16a}$, at each occurrence, is independently selected from H, C$_{1-6}$ alkyl, C$_{2-8}$ alkenyl, C$_{2-8}$ alkynyl, a (CH$_2$)$_r$—C$_{3-6}$ carbocyclic residue substituted with 0–5 R$^{16e}$, and a (CH$_2$)$_r$-5–10 membered heterocyclic system containing 1–4 heteroatoms selected from N, O, and S, substituted with 0–2 R$^{16e}$;

R$^{16b}$, at each occurrence, is independently selected from C$_{1-6}$ alkyl, C$_{2-8}$ alkenyl, C$_{2-8}$ alkynyl, a (CH$_2$)$_r$C$_{3-6}$ carbocyclic residue substituted with 0–3 R$^{16e}$, and a (CH$_2$)$_r$-5–6 membered heterocyclic system containing 1–4 heteroatoms selected from N, O, and S, substituted with 0–2 R$^{16e}$;

R$^{16d}$, at each ocurrence, is independently selected from C$_{2-8}$ alkenyl, C$_{2-8}$ alkynyl, C$_{1-6}$ alkyl substituted with 0–3 R$^{16e}$, a (CH$_2$)$_r$—C$_{3-6}$ carbocyclic residue substituted with 0–3 R$^{16e}$, and a (CH$_2$)$_r$-5–6 membered heterocyclic system containing 1–4 heteroatoms selected from N, O, and S, substituted with 0–3 R$^{16e}$;

R$^{16e}$, at each occurrence, is independently selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{16f}$R$^{16f}$, and (CH$_2$)$_r$phenyl;

R$^{16f}$, at each occurrence, is independently selected from H, C$_{1-5}$ alkyl, and C$_{3-6}$ cycloalkyl, and phenyl;

R$^{17}$ at each occurrence is independently selected from =O, C$_{1-6}$ alkyl, (CH$_2$)$_r$C$_{3-6}$ cycloalkyl, Cl, F, Br, I, CN, NO$_2$, (CH$_2$)$_r$OR$^{19}$, (CH$_2$)$_r$OH, (CH$_2$)$_r$SR$^{19}$, (CH$_2$)$_r$S(O)R$^{19}$, (CH$_2$)$_r$S(O)$_2$R$^{19}$, (CH$_2$)$_r$S(O)$_2$N(R$^{18a}$)R$^{18b}$, (CH$_2$)$_r$N(R$^{18c}$)C(O)R$^{19}$(CH$_2$)$_r$N(R$^{18c}$)S(O)$_2$R$^{19}$, (CH$_2$)$_r$C(O)OH, (CH$_2$)$_r$C(O)OR$^{19}$, (CH$_2$)$_r$C(O)N(R$^{18a}$)R$^{18b}$, (CH$_2$)$_r$N(R$^{18c}$)C(O)N(R$^{18a}$)R$^{18b}$, (CH$_2$)$_r$N(R$^{18c}$)C(O)OR$^{19}$, (CH$_2$)$_r$OC(O)N(R$^{18a}$)R$^{18b}$, (CH$_2$)$_r$N(R$^{18a}$)R$^{18b}$, C$_{1-6}$ haloalkyl, C$_{2-8}$ alkenyl substituted with 0–3 R$^{17a}$, C$_{2-8}$ alkynyl substituted with 0–3 R$^{17a}$, (CH($R^{17a}$))$_r$phenyl substituted with 1–3 $R^{18}$, and (CH($R^{17a}$))$_r$-5–10 membered heterocyclic system containing 1–4 heteroatoms selected from N, O, and S, substituted with 0–2 $R^{18}$;

$R^{17a}$ at each occurrence is independently selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with 0–3 $R^{18}$;

$R^{18}$ at each occurrence is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_r$$SC_{1-5}$ alkyl, $(CH_2)_rS(O)C_{1-5}$ alkyl, $(CH_2)_rS(O)_2C_{1-5}$ alkyl, $(CH_2)_rS(O)_2N(R^{18a})R^{18b}$, $(CH_2)_rN(R^{18c})C(O)$$C_{1-5}$ alkyl, $(CH_2)_rN(R^{18c})S(O)_2C_{1-5}$ alkyl, $(CH_2)_rC(O)$$N(R^{18a})R^{18b}$, $(CH_2)_rC(O)OC_{1-5}$ alkyl, $(CH_2)_rC(O)C_{1-5}$ alkyl, and $(CH_2)_rN(R^{18a})R^{18b}$;

$R^{18a}$, $R^{18b}$, and $R^{18c}$ at each occurrence are independently selected from H, $C_{1-6}$ alkyl, and $C_{3-6}$ cycloalkyl;

$R^{19}$ at each occurrence is independently selected from $C_{1-6}$ alkyl, $C_{3-6}$ cycloalkyl, and phenyl substituted with 0–3 $R^{18}$;

alternatively, $R^{18a}$ and $R^{18b}$ along with the nitrogen to which both are attached form a pyrrolidine, piperidine, piperazine or morpholine ring;

$R^{25}$ at each occurrence is independently selected from H, $C_{1-6}$ alkyl, $C_{2-8}$ alkenyl, $C_{2-8}$ alkynyl, $(CH_2)_rC_{3-6}$ cycloalkyl, $(CH_2)_rC(O)R^{19}$, $(CH_2)_rC(O)N(R^{18a})R^{18b}$, $(CH_2)_rC(O)OR^{19}$, $(CH_2)_rS(O)_2R^{19}$, $(CH_2)_rS(O)_2N$$(R^{18a})R^{18b}$, and $(CH_2)_r$phenyl substituted with 0–3 $R^{17}$;

i is selected from 0, 1, and 2;

m is selected from 0, 1, and 2;

s is selected from 0 and 1;

with the proviso: m+s is selected from 0, 1, and 2;

v is selected from 0, 1, 2, and 3;

with the proviso: that the total number of atoms between the nitrogen of which R' is attached and the fused ring B is less than or equal to 4;

r is selected from 0, 1, 2, 3, 4, and 5;

t is selected from 0, 1, 2, 3, 4, and 5;

q is selected from 1, 2, 3, 4, and 5;

p is selected from 1, 2, and 3;

u is selected from 0, 1 and, 2.

2. The compound of claim 1, wherein $R^{11a}$ and $R^{12a}$, at each occurrence are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_rC(O)OH$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_rOC(O)R^{19}$, $(CH_2)_rS(O)R^{19}$, $(CH_2)_rS(O)_2R^{19}$, $(CH_2)_rS(O)_2N(R^{18a})R^{18b}$, $(CH_2)_rN(R^{18c})S(O)_2R^{19}$, and $(CH_2)_r$phenyl substituted with 0–3 $R^{18}$; and $R^{11b}$, $R^{12b}$, $R^{14a}$ and $R^{14b}$ at each occurrence are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_q N(R^{18a})R^{18b}$, $(CH_2)_qOH$, $(CH_2)_qOR^{19}$, $(CH_2)_q$$SH$, $(CH_2)_qSR^{19}$, $(CH_2)_qC(O)OH$, $(CH_2)_qC(O)R^{19}$, $(CH_2)_r$ $C(O)N(R^{18a})R^{18b}$, $(CH_2)_qN(R^{18c})C(O)R^{19}$, $(CH_2)_rC(O)OR^{19}$, $(CH_2)_qOC(O)R^{19}$, $(CH_2)_qS(O)R^{19}$, $(CH_2)_qS(O)_2R^{19}$, $(CH_2)_qS(O)_2N(R^{18a})R^{18b}$, $(CH_2)_qN$$(R^{18c})S(O)_2R^{19}$, and $(CH_2)_r$phenyl substituted with 0–3 $R^{18}$.

3. The compound of claim 2, wherein $R^1$ and $R^2$ are independently selected from H, and $C_{1-8}$ alkyl;

$R^4$ is absent, taken with the nitrogen to which it is attached to form an N-oxide, or selected from $C_{1-8}$ alkyl, $(CH_2)_rC_{3-6}$ cycloalkyl, and a $(CH_2)_r$—$C_{3-6}$ carbocyclic residue substituted with 0–3 $R^{4c}$; and $R^{4c}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{4a}R^{4a}$, and $(CH_2)_r$phenyl.

4. The compound of claim 3, wherein

Z is selected from O and S;

$R^6$, at each occurrence, is independently selected from $C_{1-4}$ alkyl, $(CH_2)_rC_{3-6}$ cycloalkyl, $(CH_2)_qNR^{6a}R^{6a}$, $(CH_2)_qOH$, $(CH_2)_qOR^{6b}$, $(CH_2)_rC(O)OH$, $(CH_2)_rC(O)$$R^{6b}$, $(CH_2)_rC(O)$ $NR^{6a}R^{6a}$, $(CH_2)_qNR^{6d}C(O)R^{6a}$, $(CH_2)_rS(O)_2NR^{6a}R^{6a}$, $(CH_2)_rNR^{6d}S(O)_2R^{6b}$, and $(CH_2)_r$phenyl substituted with 0–3 $R^{6c}$;

$R^{6a}$ and $R^{6a}$, at each occurrence, are selected from H, methyl, ethyl, propyl, i-propyl, butyl, cyclopropyl, cyclopentyl, cyclohexyl, and phenyl;

$R^{6b}$, at each occurrence, is independently selected from methyl, ethyl, propyl, i-propyl, butyl, cyclopropyl, cyclopentyl, cyclohexyl, and phenyl;

$R^{6c}$, at each occurrence, is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_r$$SC_{1-5}$ alkyl, and $(CH_2)_rNR^{6d}R^{6d}$;

$R^{6d}$, at each occurrence, is independently selected from H, methyl, ethyl, propyl, i-propyl, butyl, cyclopropyl, cyclopentyl, and cyclohexyl;

$R^7$, is selected from H, $C_{1-6}$ alkyl, $C_{2-8}$ alkenyl, $C_{2-8}$ alkynyl, $(CH_2)_qOH$, $(CH_2)_qOR^{7d}$, $(CH_2)_qNR^{7a}R^{7a}$, $(CH_2)_rC(O)R^{7b}$, $(CH_2)_rC(O)NR^{7a}R^{7a}$, $(CH_2)_qNR^{7a}C$$(O)R^{7a}$, $(CH_2)_qNR^{7a}C(O)H$, $(CH_2)_rC(O)OR^{7b}$, $(CH_2)_q$$OC(O)R^{7b}$, $C_{1-6}$ haloalkyl, a $(CH_2)_r$—$C_{3-6}$ carbocyclic residue substituted with 0–3 $R^{7c}$, and a $(CH_2)_r$-5–10 membered heterocyclic system containing 1–4 heteroatoms selected from N, O, and S, substituted with 0–2 $R^{7c}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, indazolyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^{7a}$, at each occurrence, is independently selected from H, $C_{1-6}$ alkyl, and a $(CH_2)_r$—$C_{3-6}$ carbocyclic residue substituted with 0–5 $R^{7e}$;

$R^{7b}$, at each occurrence, is independently selected from $C_{1-6}$ alkyl, a $(CH_2)_r$—$C_{3-6}$ carbocyclic residue substituted with 0–2 $R^{7e}$;

$R^{7c}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF^3$, $NO_2$, CN, $(CH_2)_r$$NR^{7f}R^{7f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{7b}$, $(CH_2)_rC(O)$$NR^{7f}R^{7f}$, $(CH_2)_rNR^{7f}C(O)R^{7a}$, $(CH_2)_rC(O)OC_{1-4}$ alkyl, $(CH_2)_rOC(O)R^{7b}$, $(CH_2)_rC(=NR^{7f})NR^{7f}R^{7f}$, $(CH_2)_rS(O)_pR^{7b}$, $(CH_2)_rNHC(=NR^{7f})NR^{7f}R^{7f}$, $(CH_2)_r$$S(O)_2NR^{7f}R^{7f}$, $(CH_2)_rNR^{7f}S(O)_2R^{7b}$, and $(CH_2)_r$ phenyl substituted with 0–3 $R^{7e}$;

$R^{7d}$, at each occurrence, is independently selected from $C_{1-6}$ alkyl substituted with 0–3 $R^{7e}$, and a $C_{3-6}$ carbocyclic residue substituted with 0–3 $R^{7c}$;

$R^{7e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$ phenyl;

$R^{7f}$, at each occurrence, is independently selected from H, methyl, ethyl, propyl, i-propyl, butyl, cyclopropyl, cyclopentyl and cyclohexyl;

$R^{10}$, at each occurrence, is independently selected from H, $C_{1-4}$ alkyl, $(CH_2)_rC_{3-6}$ cycloalkyl, $(CH_2)_rNR^{10a}R^{10a}$, $(CH_2)_rC(O)NR^{10a}R^{10a}$, $(CH_2)_rNR^{10d}C(O)R^{10a}$, $(CH_2)_rS(O)_2NR^{10a}R^{10a}$, $(CH_2)_rNR^{10d}S(O)_2R^{10b}$, and $(CH_2)_t$ phenyl substituted with 0–3 $R^{10c}$;

$R^{10a}$ and $R^{10a}$, at each occurrence, are selected from H, methyl, ethyl, propyl, i-propyl, butyl, cyclopropyl, cyclopentyl, cyclohexyl, and phenyl;

$R^{10b}$, at each occurrence, is independently selected from methyl, ethyl, propyl, i-propyl, butyl, cyclopropyl, cyclopentyl, cyclohexyl, and phenyl;

$R^{10c}$, at each occurrence, is independently selected from $C_{1-10}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{10d}R^{10d}$; and $R^{10d}$, at each occurrence, is independently selected from H, methyl, ethyl, propyl, i-propyl, butyl, cyclopropyl, cyclopentyl, and cyclohexyl.

5. The compound of claim 4, wherein $R^3$ is selected from a $(CR^{3'}H)_r$—$C_{3-8}$ carbocyclic residue substituted with 0–5 $R^{15}$, wherein the carbocyclic residue is selected from phenyl, naphthyl, and adamantyl; and $R^{5a}$ is selected from phenyl substituted with 0–5 $R^{16}$; and a heterocyclic residue substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^8$ is selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_rC(O)OH$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_rOC(O)R^{19}$, $(CH_2)_rS(O)R^{19}$, $(CH_2)_rS(O)_2R^{19}$, $(CH_2)_rS(O)_2N(R^{18a})R^{18b}$, $(CH_2)_rN(R^{18c})S(O)_2R^{19}$, a $(C(R^{8a})(R^{8b}))_r$—$C_{3-10}$ carbocyclic residue substituted with 0–5 $R^{17}$, and a $(C(R^{8a})(R^{8b}))_r$-5–10 membered heterocyclic system containing 1–4 heteroatoms selected from N, O, and S, substituted with 0–3 $R^{17}$ wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^{8a}$ and $R^{8b}$, at each occurrence, are independently selected from H, methyl, ethyl, propyl, i-propyl, butyl, cyclopropyl, cyclopentyl, cyclohexyl, and $(CH_2)_r$ phenyl substituted with 0–3 $R^{18}$;

$R^9$ is selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_qN(R^{18a})R^{18b}$, $(CH_2)_qOH$, $(CH_2)_qOR^{19}$, $(CH_2)_qSH$, $(CH_2)_qSR^{19}$, $(CH_2)_qC(O)OH$, $(CH_2)_qC(O)R^{19}$, $(CH_2)_qC(O)N(R^{18a})R^{18b}$, $(CH_2)_qN(R^{18c})C(O)R^{19}$, $(CH_2)_qC(O)OR^{19}$, $(CH_2)_qOC(O)R^{19}$, $(CH_2)_qS(O)R^{19}$, $(CH_2)_qS(O)_2R^{19}$, $(CH_2)_qS(O)_2N(R^{18a})R^{18b}$, $(CH_2)_qN(R^{18c})S(O)_2R^{19}$, a $(C(R^{8a})(R^{8b}))_r$—$C_{3-10}$ carbocyclic residue substituted with 0–5 $R^{17}$, and a $(C(R^{8a})(R^{8b}))_r$-5–10 membered heterocyclic system containing 1–4 heteroatoms selected from N, O, and S, substituted with 0–3 $R^{17}$ wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

alternatively, $R^8$ and $R^9$ taken together are selected from =O, =S, =$NR^{9a}$;

$R^{9a}$ is selected from H, $C_{1-6}$ alkyl, $C_{2-8}$ alkenyl, $C_{2-8}$ alkynyl, $(CH_2)_rC_{3-6}$ cycloalkyl, $(CH_2)_rOH$, $(CH_2)_rOC_{1-6}$ alkyl, $(CH_2)_rC(O)R^{19}$, $(CH_2)_rC(O)N(R^{18a})R^{18b}$, $(CH_2)_rC(O)OR^{19}$, and $(CH_2)_r$phenyl substituted with 0–3 $R^{17}$; and $R^{9b}$, at each occurrence are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_rC(O)OH$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_rOC(O)R^{19}$, $(CH_2)_rS(O)R^{19}$, $(CH_2)_rS(O)_2R^{19}$, $(CH_2)_rS(O)_2N(R^{18a})R^{18b}$, $(CH_2)_rN(R^{18c})S(O)_2R^{19}$, and $(CH_2)_r$phenyl substituted with 0–3 $R^{17}$.

6. The compound of claim 5, wherein $R^1$ and $R^2$ are H;

$R^{5a}$ is phenyl substituted with 1–3 $R^{16}$;

$R^{16}$, at each occurrence, is independently selected from $C_{1-8}$ alkyl, $(CH_2)_rC_{3-6}$ cycloalkyl, $CF_3$, Cl, Br, I, F, $NR^{16a}R^{16a}$, $NO_2$, CN, OH, $OR^{16d}$, $C(O)R^{16b}$, $C(O)NR^{16a}R^{16a}$, and $NR^{16f}C(O)R^{16b}$;

$R^{16a}$, at each occurrence, is independently selected from H, methyl, ethyl, propyl, i-propyl, butyl, cyclopropyl, cyclopentyl, cyclohexyl, and $(CH_2)_r$phenyl substituted with 0–3 $R^{16e}$;

$R^{16b}$, at each occurrence, is independently selected from methyl, ethyl, propyl, i-propyl, butyl, cyclopropyl, cyclopentyl, cyclohexyl, and $(CH_2)_r$phenyl substituted with 0–3 $R^{16e}$;

$R^{16d}$, at each occurrence, is independently selected from methyl, ethyl, propyl, i-propyl, butyl, and phenyl;

$R^{16e}$, at each occurrence, is independently selected from methyl, ethyl, propyl, i-propyl, butyl, Cl, F, Br, I, CN, $NO_2$, $(CF_2)_rCF_3$, OH, and $(CH_2)_rOC_{1-5}$ alkyl; and $R^{16f}$, at each occurrence, is independently selected from H, methyl, ethyl, propyl, i-propyl, and butyl.

7. The compound of claim 6, wherein the compound is of formula (I-i)

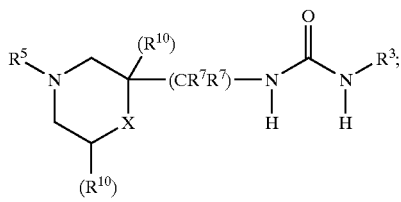

(I-i)

$R^{10}$ is selected from H, methyl, ethyl, propyl, i-propyl, butyl, OH, and $OR^{10b}$; and $R^{10b}$ is selected from methyl, ethyl, propyl, i-propyl, and butyl.

8. The compound of claim 7, wherein $R^5$ is

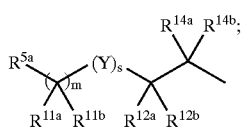

$R^{11a}$ and $R^{12a}$, at each occurrence are independently selected from H, methyl, ethyl, propyl, i-propyl, butyl, pentyl, hexyl, cyclopropyl, cyclopentyl, cylohexyl, $CF_3$, $(CH_2)_r N(R^{18a})R^{18b}$, $(CH_2)_r OH$;

$R^{11b}$, $R^{12b}$, $R^{14a}$ and $R^{14b}$ at each occurrence are independently selected from H, methyl, ethyl, propyl, i-propyl, butyl, pentyl, hexyl, cyclopropyl, cyclopentyl, cylohexyl, $CF_3$, $(CH_2)_{rq} N(R^{18a})R^{18b}$, $(CH_2)_{rq} OH$;

$R^{25}$ at each occurrence is independently selected from H, methyl, ethyl, propyl, i-propyl, butyl, cyclopropyl, cyclopentyl, cyclohexyl, $(CH_2)_r C(O)R^{19}$, $(CH_2)_r C(O)N(R^{18a})R^{18b}$, $(CH_2)_r C(O)OR^{19}$, and $(CH_2)_r$phenyl substituted with 0–3 $R^{17}$.

9. The compound of claim 8, wherein $R^5$ is

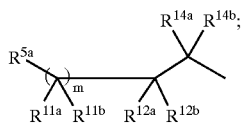

$R^7$, at each occurrence, is selected from H, methyl, ethyl, propyl, i-propyl, butyl, $(CH_2)_q OH$;

$R^{11a}$ and $R^{12a}$, at each occurrence, are independently selected from H, methyl, and ethyl;

$R^{11b}$, $R^{12b}$, $R^{14a}$, and $R^{14b}$, at each occurrence, are independently selected from H, methyl, ethyl and OH; and R16, at each occurrence, is independently selected from methyl, Cl, F, $CF_3$, and CN.

10. The compound of claim 7, wherein $R^5$ is

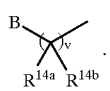

11. The compound of claim 9, wherein $R^8$ and $R^9$ do not both represent H.

12. The compound of claim 1, wherein the compound is selected from

1-{1-[3-(4-fluorophenyl)-2,2-dimethylpropyl]-piperidin-3-ylmethyl}-3-[3-(1-methyl-1H-tetrazol-5-yl)-phenyl]-urea;

1-{1-[3-(4-fluorophenyl)-propyl]-piperidin-3-ylmethyl}-3-[3-(1-methyl-1H-tetrazol-5-yl)-phenyl]-urea;

1-[3-(1-methyl-1H-tetrazol-5-yl)-phenyl]-3-{1-[2-(4-trifluoromethylphenyl)-ethyl]-piperidin-3-ylmethyl}-urea;

1-[3-ethyl-5-(1-methyl-1H-tetrazol-5-yl)phenyl]-3-{trans-1-[2-(4-fluorophenyl)-ethyl]-4-methylpiperidin-3-ylmethyl}-urea;

1-[3-(1-methyl-1H-tetrazol-5-yl)phenyl]-3-{cis-1-[2-(4-fluorophenyl)-ethyl]-4-methylpiperidin-3-ylmethyl}-urea;

trans-1-{4-(benzyl-methylamino)-1-[2-(4-fluorophenyl)-ethyl]-piperidin-3-ylmethyl}-3-[3-ethyl-5-(1-methyl-1H-tetrazol-5-yl)-phenyl]-urea;

trans-1-{4-methylamino-1-[2-(4-fluorophenyl)-ethyl]-piperidin-3-ylmethyl}-3-[3-ethyl-5-(1-methyl-1H-tetrazol-5-yl)-phenyl]-urea;

trans-N-{3-{3-[3-ethyl-5-(1-methyl-1H-tetrazol-5-yl)-phenyl]-ureidomethyl}-1-[3-(4-fluoro-phenyl)-propyl]-piperidin-4-yl}-N-methyl-acetamide;

trans-N-{3-{3-[3-ethyl-5-(1-methyl-1H-tetrazol-5-yl)-phenyl]-ureidomethyl}-1-[3-(4-fluoro-phenyl)-propyl]-piperidin-4-yl}-N-methyl-methanesulfonamide;

(S)-1-[3-ethyl-5-(1-methyl-1H-tetrazol-5-yl)-phenyl]-3-{1-[2-(4-fluorophenyl)-2-oxo-ethyl]-piperidin-3-ylmethyl}-urea;

(S)-1-[3-ethyl-5-(1-methyl-1H-tetrazol-5-yl)-phenyl]-3-{1-[2-(4-fluorophenyl)-2-hydroxyimino-ethyl]-piperidin-3-ylmethyl}-urea;

1-[3-ethyl-5-(1-methyl-1H-tetrazol-5-yl)-phenyl]-3-{1-[2-(4-fluorophenyl)-2-(RS)-hydroxyethyl]-(S)-piperidin-3-ylmethyl}-urea;

(S)-1-[3-ethyl-5-(1-methyl-1H-tetrazol-5-yl)-phenyl]-3-{1-[2-(4-fluorophenyl)-ethyl]-piperidin-3-ylmethyl}-urea;

1-[3-ethyl-5-(1-methyl-1H-tetrazol-5-yl)phenyl]-3-{1-[2-(4-fluorophenyl)-ethyl]-4-ethylpiperidin-3-ylmethyl}-urea; and 1-[3-ethyl-5-(1-methyl-1H-tetrazol-5-yl)phenyl]-3-{1-[2-(4-fluorophenyl)-ethyl]-4,4-dimethylpiperidin-3-ylmethyl}-urea.

13. A pharmaceutical composition, comprising a pharmaceutically acceptable carrier and a therapeutically effective amount of a compound according to claim 1.

14. A method for treating asthma, comprising administering to a patient in need thereof a therapeutically effective amount of a compound according to claim 1.

15. A pharmaceutical composition comprising a pharmaceutically acceptable carrier and a therapeutically effective amount of a compound according to claim 1, or a pharmaceutically acceptable salt thereof.

16. A pharmaceutical composition comprising a pharmaceutically acceptable carrier and a therapeutically effective amount of a compound according to claim 7, or a pharmaceutically acceptable salt thereof.

17. A method for treating a disorder selected from asthma, allergic rhinitis, atopic dermatitis, inflammatory bowel diseases, idiopathic pulmonary fibrosis, bullous pemphigoid, allergic colitis, eczema, conjunctivitis, familial eosinophilia, eosinophilic cellulitis, eosinophilic pneumonias, eosinophilic fasciitis, and eosinophilic gastroenteritis, comprising administering to a patient in need thereof a therapeutically effective amount of a compound according to claim 1, or a pharmaceutically acceptable salt thereof.

18. The method according to claim 17, wherein the disorder is selected from asthma, allergic rhinitis, atopic dermatitis, and inflammatory bowel diseases.

19. The method according to claim 18, wherein the disorder is asthma.

20. A pharmaceutical composition, comprising a pharmaceutically acceptable carrier and a therapeutically effective amount of a compound according to claim 7.

21. A method for treating asthma, comprising administering to a patient in need thereof a therapeutically effective amount of a compound according to claim 7.

* * * * *

UNITED STATES PATENT AND TRADEMARK OFFICE
CERTIFICATE OF CORRECTION

PATENT NO. : 6,919,356 B2 Page 1 of 1
DATED : July 19, 2005
INVENTOR(S) : Douglas G. Batt It is certified that error appears in the above-identified patent and that said Letters Patent is hereby corrected as shown below:

Column 89,
Line 31, replace "$R_{6b}$" with -- $R^{6b}$ --.
Line 38, replace "$R_{6d}$" with -- $R^{6d}$ --.
Line 39, replace "$C_{16}$" with -- $C_{1-6}$ --.

Column 90,
Line 65, replace "$CF^3$" with -- $CF_3$ --.

Column 91,
Line 46, replace "$(CHR)_rR^{15b}$" with -- $(CHR')_rR^{15b}$ --.

Column 92,
Line 62, "$C(O)R^{19}$" with -- $C(O)R^{19}$, --.

Column 94,
Line 57, replace "$(CF_2)_rCF^3$" with -- $(CF_2)_rCF_3$ --.

Column 95,
After line 10, insert -- $(CH_2)_rOH$, $(CH_2)_rOR^{10b}$, $(CH_2)_rC(O)OH$, $(CH_2)_rC(O)R^{10b}$, --.

Column 97,
Line 33, replace "$(CH_2)_{rq}N(R^{18a})R^{18b}$, $(CH_2)_{rq}OH;$" with -- $(CH_2)_rN(R^{18a})R^{18b}$, $(CH_2)_rOH;$ --.
Line 56, replace "R16" with -- $R^{16}$ --.

Signed and Sealed this

Twenty-first Day of March, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,919,356 B2 | Page 1 of 1 |
| APPLICATION NO. | : 10/670596 | |
| DATED | : July 19, 2005 | |
| INVENTOR(S) | : Batt | |

It is certified that error appears in the above-identified patent and that said Letters Patent is hereby corrected as shown below:

On the title page: Item [*] Notice: should read, Subject to any disclaimer, the term of this patent is extended or adjusted under 35 U.S.C. 154(b) by 60 days.

Signed and Sealed this

Twelfth Day of September, 2006

JON W. DUDAS
*Director of the United States Patent and Trademark Office*